US010000496B2

(12) United States Patent
Hodous et al.

(10) Patent No.: US 10,000,496 B2
(45) Date of Patent: Jun. 19, 2018

(54) COMPOSITIONS USEFUL FOR TREATING DISORDERS RELATED TO KIT AND PDGFR

(71) Applicant: BLUEPRINT MEDICINES CORPORATION, Cambridge, MA (US)

(72) Inventors: Brian L. Hodous, Cambridge, MA (US); Kevin J. Wilson, Boston, MA (US); Yulian Zhang, Acton, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days. days.

(21) Appl. No.: 15/217,503

(22) Filed: Jul. 22, 2016

(65) Prior Publication Data
US 2017/0022206 A1    Jan. 26, 2017

Related U.S. Application Data

(60) Provisional application No. 62/196,445, filed on Jul. 24, 2015.

(51) Int. Cl.
*C07D 487/04* (2006.01)
*A61K 31/53* (2006.01)
*A61K 45/06* (2006.01)

(52) U.S. Cl.
CPC ............ *C07D 487/04* (2013.01); *A61K 31/53* (2013.01); *A61K 45/06* (2013.01)

(58) Field of Classification Search
CPC .............................. C07D 487/04; A61K 31/53
USPC ........................................... 544/183; 514/243
See application file for complete search history.

(56) References Cited

U.S. PATENT DOCUMENTS

| | | |
|---|---|---|
| 6,982,265 B1 | 1/2006 | Hunt et al. |
| 8,609,672 B2 | 12/2013 | Russu et al. |
| 8,802,697 B2 | 8/2014 | Bifulco, Jr. et al. |
| 9,126,951 B2 | 9/2015 | Bifulco, Jr. et al. |
| 9,200,002 B2 | 12/2015 | Hodous et al. |
| 9,334,263 B2 | 5/2016 | Hodous et al. |
| 9,340,514 B2 | 5/2016 | Bifulco, Jr. et al. |
| 9,434,700 B2 | 9/2016 | Bifulco, Jr. et al. |
| 9,499,522 B2 | 11/2016 | DiPietro et al. |
| 9,688,680 B2 | 6/2017 | Hodous |
| 9,695,165 B2 | 7/2017 | Bifulco, Jr. et al. |
| 2014/0187559 A1 | 7/2014 | Miduturu |
| 2016/0102097 A1 | 4/2016 | Hodous et al. |
| 2017/0029409 A1 | 2/2017 | DiPietro et al. |
| 2017/0057953 A1 | 3/2017 | Hodous et al. |
| 2017/0066773 A1 | 3/2017 | Wenglowsky et al. |
| 2017/0066812 A1 | 3/2017 | Bifulco, Jr. et al. |
| 2017/0121312 A1 | 5/2017 | Brubaker et al. |
| 2017/0145018 A1 | 5/2017 | Wenglowsky et al. |
| 2017/0174652 A1 | 6/2017 | Bifulco, Jr. et al. |
| 2017/0204104 A1 | 7/2017 | Hodous et al. |
| 2017/0253593 A1 | 9/2017 | Bifulco, Jr. et al. |
| 2017/0267661 A1 | 9/2017 | Kim et al. |
| 2017/0298069 A1 | 10/2017 | Brooijmans et al. |

FOREIGN PATENT DOCUMENTS

| | | |
|---|---|---|
| WO | 0071129 A1 | 11/2000 |
| WO | 01/25220 A1 | 4/2001 |
| WO | 2005117909 A2 | 12/2005 |
| WO | 2007085188 A1 | 8/2007 |
| WO | 2008005956 A2 | 1/2008 |
| WO | 2009015254 A1 | 1/2009 |
| WO | 2009117157 A1 | 9/2009 |
| WO | 2010022055 A2 | 2/2010 |
| WO | 2010144345 A1 | 12/2010 |
| WO | 2011005119 A1 | 1/2011 |
| WO | 2011103196 A1 | 8/2011 |
| WO | 2012027495 A1 | 3/2012 |
| WO | 2014160521 A1 | 10/2014 |
| WO | 2015057873 A1 | 4/2015 |
| WO | 2015058129 A1 | 4/2015 |
| WO | 2016022569 A1 | 2/2016 |
| WO | WO 2017/019442 A1 | 2/2017 |

OTHER PUBLICATIONS

International Search Report and Written Opinion for International Application No. PCT/US2014/060746 dated Dec. 17, 2014.
International Search Report and Written Opinion for International Application No. PCT/US2014/061211 dated Dec. 10, 2014.
International Search Report and Written Opinion for International Application No. PCT/US2014/027008 dated Jul. 17, 2014.
Quintela et al, "A Ready One-pot Preparation for Pyrrolo[2,1-f]-[1,2,4]triazine and Pyrazolo[5,1-c]pyrimido[4,5-e]-[1,2,4]triazine Derivatives" Tetrahedron (1996) vol. 52, No. 8, pp. 3037-3048.
Antonescu, "What lessons can be learned from the GIST paradigm that can be applied to other kinase-driven cancers" J. Pathol. (2011) vol. 223, No. 2, pp. 251-261.
Lee et al. "Correlation of Imatinib Resistance with the Mutational Status of KIT and ODGFRA Genes in Gastrointestinal Stromal Tumors: a Meta-analysis" J. Gastrointestin Liver Dis. (2013) vol. 22, No. 4, pp. 413-418.
Cecil Textbook of Medicine, Edited by Bennet and Plum (1996) 20th edition, vol. 1, pp. 1004-1010.
Cohen et al., "The development and therapeutic potential of protein kinase inhibitors" Current Opinion in Chemical Biology (1999) vol. 3, pp. 459-465.
Fresheny et al., "Culture of Animal Cells, A Manual of Basic Technique" Alan R. Liss, Inc. (1983) pp. 1-6.
Schnittger et al. "KIT-D816 mutations in AML1-ETO-positive AML are associated with impaired event-free and overal survival" Blood (2006) vol. 107, pp. 1791-1799.
Paschka et al. "Adverse Prognostic Significance of KIT Mutations in Adult Acute Myeloid Leukemia with inv(16) and t(8;21):A Cancer and Leukemia Group Study" Journal of Clinical Oncology (2006) vol. 24, No. 24, pp. 3904-3911.

(Continued)

*Primary Examiner* — Venkataraman Balasubramanian
(74) *Attorney, Agent, or Firm* — Finnegan, Henderson, Farabow, Garrett & Dunner, LLP

(57) ABSTRACT

Compounds and compositions useful for treating disorders related to KIT and PDGFR are described herein.

54 Claims, No Drawings

(56) References Cited

OTHER PUBLICATIONS

Cairoli et al. "Prognostic impact of c-KIT mutations in core binding factor leukemias: an Italian retrospective study" Blood (2006) vol. 107, pp. 3463-3468.
International Search Report for International Application No. PCT/US2015/043624 dated Oct. 6, 2015.
Dermer "Another Anniversary for the War on Cancer" Bio/Technology (1994) vol. 12, pp. 320.
International Search Report and Written Opinion for International Application No. PCT/US2016/043301, dated Oct. 17, 2016 (11 pages).
U.S. Appl. No. 15/462,255, filed Mar. 17, 2017, by Kim et al.
U.S. Appl. No. 15/488,257, filed Apr. 14, 2017, by Brooijmans et al.
U.S. Appl. No. 15/548,925, filed Aug. 4, 2017, by Brooijmans et al.
U.S. Appl. No. 15/657,057, filed Jul. 21, 2017, by Brubaker et al.
U.S. Appl. No. 15/599,006, filed May 18, 2017, by Bifuco et al.
Notice of Allowance dated Sep. 26, 2017, in U.S. Appl. No. 15/093,354, filed Apr. 7, 2016, by Blueprint Medicines Corp.
Notice of Allowance dated Oct. 25, 2017, in U.S. Appl. No. 15/340,428, filed Nov. 1, 2016, by Blueprint Medicines Corp.
Notice of Allowance dated Dec. 15, 2017, in U.S. Appl. No. 15/462,255, filed Mar. 17, 2017, by Blueprint Medicines Corp.
Notice of Allowance dated Nov. 30, 2017, in U.S. Appl. No. 15/479,145, filed Apr. 4, 2017, by Blueprint Medicines Corp.
U.S. Appl. No. 15/660,840, filed Jul. 26, 2017, by Brubaker et el.

COMPOSITIONS USEFUL FOR TREATING DISORDERS RELATED TO KIT AND PDGFR

CLAIM OF PRIORITY

This application claims priority to U.S. Ser. No. 62/196,445, filed on Jul. 24, 2015, the contents of which are incorporated herein by reference.

BACKGROUND

The invention relates to compounds and compositions useful for treating disorders related to KIT and PDGFR.

The enzyme KIT (also called CD117) is a receptor tyrosine kinase expressed on a wide variety of cell types. The KIT molecule contains a long extracellular domain, a transmembrane segment, and an intracellular portion. The ligand for KIT is stem cell factor (SCF), whose binding to the extracellular domain of KIT induces receptor dimerization and activation of downstream signaling pathways. KIT mutations generally occur in the DNA encoding the juxtumembrane domain (exon 11). They also occur, with less frequency, in exons 7, 8, 9, 13, 14, 17, and 18. Mutations make KIT function independent of activation by SCF, leading to a high cell division rate and possibly genomic instability. Mutant KIT has been implicated in the pathogenesis of several disorders and conditions including systemic mastocytosis, GIST (gastrointestinal stromal tumors), AML (acute myeloid leukemia), melanoma, and seminoma. As such, there is a need for therapeutic agents that inhibit KIT, and especially agents that inhibit mutant KIT.

Platelet-derived growth factor receptors (PDGFR) are cell surface tyrosine kinase receptors for members of the platelet-derived growth factor (PDGF) family. PDGF subunits -A and -B are important factors regulating cell proliferation, cellular differentiation, cell growth, development and many diseases including cancer. A PDGFRA D842V mutation has been found in a distinct subset of GIST, typically from the stomach. The D842V mutation is known to be associated with tyrosine kinase inhibitor resistance. As such, there is a need for agents that target this mutation.

SUMMARY OF THE INVENTION

The invention features compounds and compositions for treating conditions such as mastocytosis, GIST, and AML, such as compounds of Formula I:

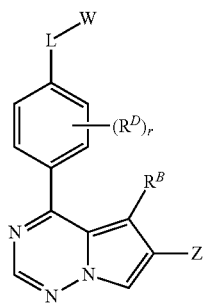

I or a pharmaceutically acceptable salt thereof, wherein:

W is selected from hydrogen and

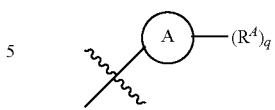

wherein Ring A is selected from monocyclic or bicyclic aryl, monocyclic or bicyclic heteroaryl, cycloalkyl and heterocyclyl;

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic and bicyclic heterocyclylalkyl is independently substituted with 0-5 occurrences of $R^C$;

L is selected from —N($R^1$)—C(O)—, —N($R^1$)C(O)N($R^1$)—, —N($R^1$)C(O)N($R^1$)—($C_1$-$C_6$ alkylene)-, N($R^1$)—($C_1$-$C_6$ alkylene)-, —N($R^1$)—C(O)—($C_1$-$C_6$ alkylene)-, —N($R^1$)—S(O)$_2$, and —N($R^1$)—S(O)$_2$—($C_1$-$C_6$ alkylene)-; wherein each alkylene is independently substituted with 0-5 occurrences of $R^2$;

each $R^A$ is independently selected from $C_1$-$C_6$ alkyl, $C_1$-$C_6$ alkoxy, halo, $C_1$-$C_6$ haloalkyl, $C_1$-$C_6$ hydroxyalkyl, $C_1$-$C_6$ heteroalkyl, —N($R^1$)($R^1$), cyano, and —$OR^1$;

each $R^B$ is independently selected from hydrogen, $C_1$-$C_6$ alkyl, $C_1$-$C_6$ cycloalkyl, hydroxyl, halo, $C_1$-$C_6$ alkoxy, $C_1$-$C_6$ haloalkyl, —N($R^1$)($R^1$), and cyano;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —C(O)$R^1$, —OC(O)$R^1$, —C(O)O$R^1$, —S$R^1$, —S(O)$_2$ $R^1$, —S(O)$_2$—N($R^1$)($R^1$), —($C_1$-$C_6$ alkylene)-S(O)$_2$—N($R^1$)($R^1$), —N($R^1$)($R^1$), —C(O)—N($R^1$)($R^1$), —N($R^1$)($R^1$)—C(O)$R^1$, —($C_1$-$C_6$ alkylene)-N($R^1$)—C(O)$R^1$, —N$R^1$S(O)$_2R^1$, —P(O)($R^1$)($R^1$), and —O$R^1$; wherein each of heteroalkyl, haloalkyl, haloalkoxy, alkyl, alkynyl, cycloalkyl, aryl, aryloxy, aralkyl, heterocyclyl, heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^D$ is independently selected from halo, $C_1$-$C_6$ alkyl, $C_1$-$C_6$ cycloalkyl, hydroxyl, halo, $C_1$-$C_6$ alkoxy, $C_1$-$C_6$ haloalkyl, —N($R^2$)($R^2$), and cyano;

each $R^1$ is independently selected from hydrogen, hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, $C_1$-$C_6$ thioalkyl, —NR"R", cycloalkyl, cycloalkylalkyl, heterocyclyl, and heterocyclylalkyl, wherein each of $C_1$-$C_6$ alkyl, cycloalkyl and heterocyclyl is independently substituted with 0-5 occurrences of $R^b$; or 2 $R^1$ together with the atom(s) to which they are attached form a cycloalkyl or heterocyclyl ring;

each $R^2$ is independently selected from hydroxyl, $C_1$-$C_6$ alkyl, $C_1$-$C_6$ alkoxyl, —NR'R'; or 2 $R^2$ together with the atom(s) to which they are attached form a cycloalkyl or heterocyclyl ring;

each $R^a$ and $R^b$ is independently selected from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein cycloalkyl is substituted with 0-5 occurrences of R';

each R' is independently selected from hydrogen, $C_1$-$C_6$ alkyl, $C_1$-$C_6$ alkoxyl, $C_1$-$C_6$ heteroalkyl, halo, hydroxyl, $C_1$-$C_6$ haloalkyl, $C_1$-$C_6$ hydroxyalkyl, cycloalkyl and cyano; or 2R' together with the atom(s) to which they are attached form a cycloalkyl or heterocyclyl ring;

each R" is hydrogen, $C_1$-$C_6$ alkyl, —C(O)—$C_1$-$C_6$ alkyl, —C(O)—NR'R'; or —C(S)—NR'R'; and each q and r is independently 0, 1, 2, 3, or 4.

Any of the compounds disclosed herein may be used, alone or in combination with another therapeutic agent, to treat any of the diseases disclosed herein.

DETAILED DESCRIPTION OF THE INVENTION

Definitions

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —$CH_2$—, —$CH_2CH_2$—, and $CH_2CH_2CH_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like.

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Haloalkyl" and "haloalkoxy" refers to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —$CH_2OCH_2CH_3$ radical is referred to as a "$C_3$" heteroalkyl. Connection to the rest of the molecule may be through either a heteroatom or a carbon in the heteroalkyl chain.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a -(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, isoxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1, 4-oxazin-3-(4H)-one, 5,6,7,8-tetrahydroquinolinyl and 5,6, 7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, oxetanyl, azetidinyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In some embodiments, heterocyclyl can include:

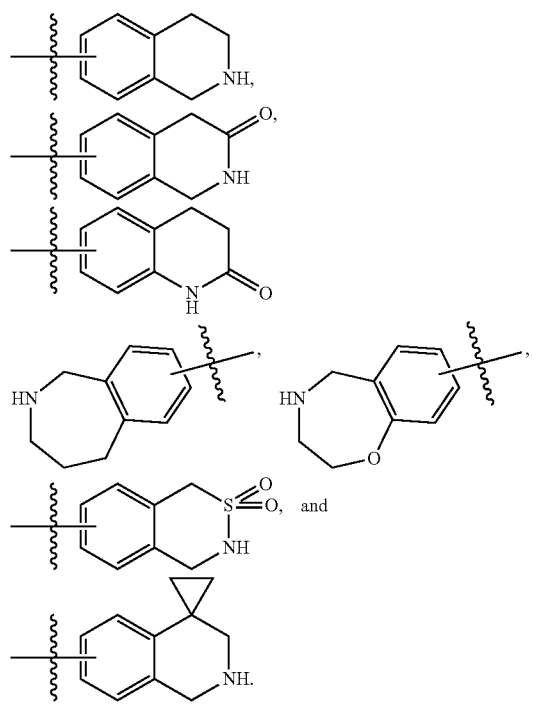

"Heterocyclylalkyl" refers to an alkyl group substituted with a heterocycle group.

"Cyano" refers to a —CN radical.

"Nitro" refers to —NO$_2$.

"Hydroxy" or "hydroxyl" refers to —OH.

"Hydroxyalkylene" refers to a divalent alkyl, e.g., —CH$_2$—, —CH$_2$CH$_2$—, and —CH$_2$CH$_2$CH$_2$—, in which one or more hydrogen atoms are replaced by a hydroxy, and includes alkyl moieties in which all hydrogens have been replaced by hydroxy.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$ee=(90-10)/100=80\%.$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Certain compounds disclosed herein can exist in unsolvated forms as well as solvated forms, including hydrated forms. The term "hydrate" or "hydrated" as used herein, refers to a compound formed by the union of water with the parent compound.

In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As used herein, the terms a "patient," "subject," "individual," and "host" refer to either a human or a non-human animal suffering from or suspected of suffering from a disease or disorder associated with aberrant KIT expression (i.e., increased KIT activity caused by signaling through KIT) or biological activity. Such organisms preferably include, but are not limited to, mammals (e.g., murines, simians, equines, bovines, porcines, canines, felines, and the like), and most preferably includes humans.

"Treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "preventing" when used in relation to a condition or disease such as cancer, refers to a reduction in the frequency of, or delay in the onset of, symptoms of the condition or disease. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The term "therapeutic effect" refers to a beneficial local or systemic effect in animals, particularly mammals, and more particularly humans, caused by administration of a compound or composition of the invention. The phrase "therapeutically effective amount" means that amount of a compound or composition of the invention that is effective to treat a disease or condition caused by over expression of KIT or aberrant KIT biological activity at a reasonable benefit/risk ratio. The therapeutically effective amount of such substance will vary depending upon the subject and disease condition being treated, the weight and age of the subject, the severity of the disease condition, the manner of administration and the like, which can readily be determined by one of skill in the art.

As used herein, "developing resistance" means that when a drug is first administered to the patient, the patient's symptoms improve, whether measured by decrease in tumor volume, a decrease in the number of new lesions, or some other means that a physician uses to judge disease progression; however, those symptoms stop improving, or even worsen at some point. At that time, the patient is said to have developed resistance to the drug.

Compounds

The invention features compounds of Formula I:

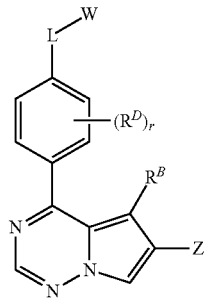

I or a pharmaceutically acceptable salts thereof, wherein:
W is selected from hydrogen and

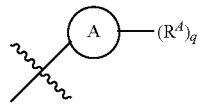

wherein Ring A is selected from monocyclic or bicyclic aryl, monocyclic or bicyclic heteroaryl, cycloalkyl and heterocyclyl;

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl; wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, monocyclic and bicyclic heterocyclylalkyl is independently substituted with 0-5 occurrences of $R^C$;

L is selected from —N($R^1$)—C(O)—*, —N($R^1$)C(O)N($R^1$)—*, —N($R^1$)C(O)N($R^1$)—($C_1$-$C_6$ alkylene)-*, —N($R^1$)—($C_1$-$C_6$ alkylene)-*, —N($R^1$)—C(O)—($C_1$-$C_6$ alkylene)-*, —N($R^1$)—S(O)$_2$—*, and —N($R^1$)—S(O)$_2$—($C_1$-$C_6$ alkylene)-*; wherein each alkylene is independently substituted with 0-5 occurrences of $R^2$, and "*" represents a portion of L bound to W;

each $R^A$ is independently selected from $C_1$-$C_6$ alkyl, $C_1$-$C_6$ alkoxy, halo, $C_1$-$C_6$ haloalkyl, $C_1$-$C_6$ hydroxyalkyl, $C_1$-$C_6$ heteroalkyl, —N($R^1$)($R^1$), cyano, and —O$R^1$;

each $R^B$ is independently selected from hydrogen, $C_1$-$C_6$ alkyl, $C_1$-$C_6$ cycloalkyl, hydroxyl, halo, $C_1$-$C_6$ alkoxy, $C_1$-$C_6$ haloalkyl, —N($R^1$)($R^1$), and cyano;

each $R^C$ is independently selected from $C_1$-$C_6$ alkyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —C(O)$R^1$, —OC(O)$R^1$, —C(O)O$R^1$, —S$R^1$, —S(O)$_2$ $R^1$, —S(O)$_2$—N($R^1$)($R^1$), —($C_1$-$C_6$ alkylene)-S(O)$_2$—N($R^1$)($R^1$), —N($R^1$)($R^1$), —C(O)—N($R^1$)($R^1$), —N($R^1$)($R^1$)—C(O)$R^1$, —($C_1$-$C_6$ alkylene)-N($R^1$)—C(O) $R^1$, —N$R^1$S(O)$_2R^1$, —P(O)($R^1$)($R^1$), and —O$R^1$; wherein each of heteroalkyl, haloalkyl, haloalkoxy, alkyl, alkynyl, cycloalkyl, aryl, aryloxy, aralkyl, heterocyclyl, heterocyclylalkyl is independently substituted with 0-5 occurrences of $R^a$; or 2$R^C$ together with the carbon atom(s) to which they are attached form a cycloalkyl or heterocyclyl ring substituted with 0-5 occurrences of $R^a$;

each $R^D$ is independently selected from halo, $C_1$-$C_6$ alkyl, $C_1$-$C_6$ cycloalkyl, hydroxyl, halo, $C_1$-$C_6$ alkoxy, $C_1$-$C_6$ haloalkyl, —N($R^2$)($R^2$), and cyano;

each $R^1$ is independently selected from hydrogen, hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, $C_1$-$C_6$ thioalkyl, —NR"R", cycloalkyl, cycloalkylalkyl, heterocyclyl, and heterocyclylalkyl, wherein each of $C_1$-$C_6$ alkyl, cycloalkyl and heterocyclyl is independently substituted with 0-5 occurrences of $R^b$; or 2 $R^1$ together with the atom(s) to which they are attached form a cycloalkyl or heterocyclyl ring;

each $R^2$ is independently selected from hydroxyl, $C_1$-$C_6$ alkyl, $C_1$-$C_6$ alkoxyl, —NR'R'; or 2 $R^2$ together with the atom(s) to which they are attached form a cycloalkyl or heterocyclyl ring;

each $R^a$ and $R^b$ is independently selected from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein cycloalkyl is substituted with 0-5 occurrences of R';

each R' is independently selected from hydrogen, $C_1$-$C_6$ alkyl, $C_1$-$C_6$ alkoxyl, $C_1$-$C_6$ heteroalkyl, halo, hydroxyl, $C_1$-$C_6$ haloalkyl, $C_1$-$C_6$ hydroxyalkyl, cycloalkyl and cyano; or 2R' together with the atom(s) to which they are attached form a cycloalkyl or heterocyclyl ring;

each R" is hydrogen, $C_1$-$C_6$ alkyl, —C(O)—$C_1$-$C_6$ alkyl, —C(O)—NR'R'; or —C(S)—NR'R'; and each q and r is independently 0, 1, 2, 3, or 4.

In some embodiments, the the invention features compounds of Formula II or Formula III, or pharmaceutically acceptable salts thereof.

Formula II

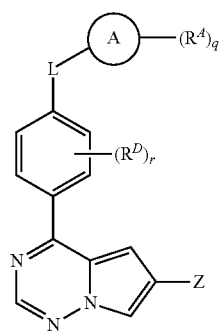

Formula III

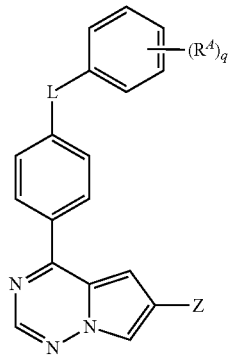

In some embodiments, L is additionally selected from —NH—C(O)—($C_3$-$C_6$ cycloalkdiyl)-.

In some embodiments, L is a bond. In other embodiments, L is —N($R^1$)—C(O)—($C_1$-$C_6$ alkylene)-, wherein the alkylene portion of L is substituted with 0-5 occurrences of $R^2$. In still other embodiments, L is selected from —NHS(O)$_2$CH$_2$—*, —NHS(O)$_2$CH(CH$_3$)CH$_2$—*, —NHC(O)CH$_2$—*, —NHC(O)NHCH$_2$—*, —NHC(O)CH(OH)—*, —NHC(O)—*, —NHS(O)$_2$—*, —NHC(O)CH(OCH$_3$)—*, —NHC(O)NH—*, —NHC(O)CH(CH$_3$)—*, —NHC(O)—CH(NH$_2$)—*, —NHC(O)C(CH$_3$)$_2$—*, —NHC(O)CH(CH$_2$CH$_3$)—*, —NHC(O)C(CH$_3$)(NH$_2$)—*, —NHC(O)C(OH)(CH$_3$)—*, —NHC(O)CH(CH(CH$_3$)$_2$)—*, —NHC(O)CH(N(CH$_3$)$_2$)—*, and

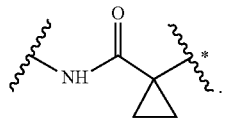 [SMILES: *NC(=O)C1(*)CC1]

In a more specific embodiment, L is selected from —NHS(O)$_2$CH$_2$—*, —NHC(O)CH(OH)—*, —NHS(O)$_2$—*, —NHC(O)CH(OCH$_3$)—*, —NHC(O)CH(CH$_3$)—*, —NHC(O)—CH(NH$_2$)—*, —NHC(O)C(CH$_3$)$_2$—*, —NHC(O)CH(CH$_2$CH$_3$)—*, —NHC(O)C(CH$_3$)(NH$_2$)—*, and —NHC(O)C(OH)(CH$_3$)—*, In some embodiments, W is hydrogen. In other embodiments, W is ring A. In some embodiments, ring A is a monocyclic or bicyclic aryl or heteroaryl. In some embodiments, ring A is monocyclic or bicyclic aryl. In some embodiments, ring A is monocyclic or bicyclic heteroaryl. In some embodiments, ring A is selected from phenyl, pyridinyl and 1H-pyrazolyl. In some embodiments, ring A is selected from phenyl, pyridin-3-yl, pyridin-2-yl and 1H-pyrazol-4-yl. In a more specific embodiment, ring A is phenyl.

In some embodiments, Z is monocyclic or bicyclic aryl, each independently substituted with 0-5 occurrences of $R^C$. In others, Z is monocyclic or bicyclic heteroaryl, each independently substituted with 0-5 occurrences of $R^C$. In some embodiments, Z is selected from pyrazolyl, phenyl, indolyl, dioxanyl, tetrahydropyridinyl, each independently substituted with 0-5 occurrences of $R^C$. For example, in some embodiments, Z is pyrazolyl substituted with 0-5 occurrences of $R^C$. In some embodiments, Z is selected from 4-fluorophenyl, 4-t-butoxyphenyl, 4-isopropoxyphenyl, 4-(dimethylaminoacarbonyl)phenyl, 4-methylsufonylphenyl, 4-(azetidin-1-ylcarbonyl)phenyl 1-methyl-1H-pyrazol- 4-yl, 1-(2-hydroxy-2-methylpropyl)-1H-pyrazol-4-yl, 1H-indol-3-yl, 1,4-dioxan-2-yl, 1-propionyl-1,2,3,6-tetrahydropyridin-4-yl, and 1-ethylcarboxy-1,2,3,6-tetrahydropyridin-4-yl. In a more specific embodiment, Z is selected from 1-methyl-1H-pyrazol-4-yl and 1-ethylcarboxy-1,2,3,6-tetrahydropyridin-4-yl. In an even more specific embodiment, Z is 1-methyl-1H-pyrazol-4-yl.

In some embodiments, each $R^A$ is independently selected from $C_1$-$C_6$ alkyl, $C_1$-$C_6$ alkoxy, halo, —N($R^1$)($R^1$), and cyano. In some embodiments, each $R^A$ is independently selected from cyano, fluoro, chloro, and —OCH$_3$. In an even more specific embodiment, each $R^A$ is chloro or cyano.

In some embodiments, q is 0, 1 or 2. In a more specific embodiment q is 1 or 2. In an even more specific embodiment, ring A and $(R^A)_q$ taken together is selected from 4-chlorophenyl, 4-cyanophenyl and 2,4-dichlorophenyl.

In some embodiments, $R^D$ is halo. In some embodiments, $R^D$ is fluoro.

In some embodiments, r is 0. In some embodiments, r is 1.

In some embodiments, each $R^C$ is independently selected from $C_1$-$C_6$ alkyl, halo, $C_1$-$C_6$ hydroxyalkyl, —C(O)$R^1$, —OC(O)$R^1$, —C(O)O$R^1$, —S$R^1$, —S(O)$_2R^1$, —S(O)$_2$—N($R^1$)($R^1$), —N($R^1$)($R^1$), —C(O)—N($R^1$)($R^1$), —N$R^1$S(O)$_2R^1$, and —O$R^1$, wherein each of $C_1$-$C_6$ alkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$.

In some embodiments, each $R^1$ is independently selected from hydrogen, hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, —NR"R wherein each of $C_1$-$C_6$ alkyl is independently substituted with 0-5 occurrences of $R^b$; or 2 $R^1$ together with the atom(s) to which they are attached form a cycloalkyl or heterocyclyl ring.

The invention also features pharmaceutical compositions containing a pharmaceutically acceptable carrier and any compound of Formulas I-III.

The table below shows the structures of compounds described herein.

| Compound Number | Structure |
|---|---|
| 1 | 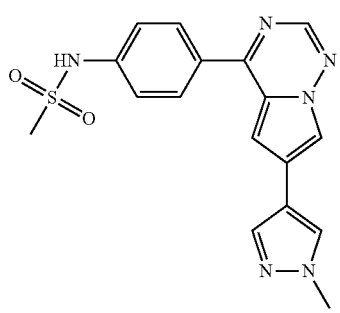 [SMILES: Cn1cc(-c2cc3c(-c4ccc(NS(C)(=O)=O)cc4)ncnn3c2)cn1] |
| 2 | 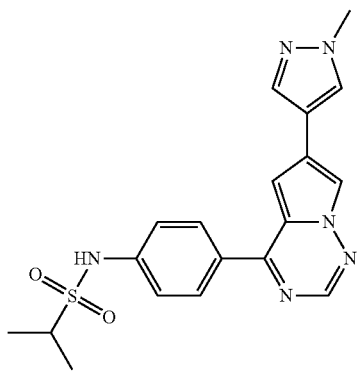 [SMILES: CC(C)S(=O)(=O)Nc1ccc(-c2ncnn3cc(-c4cnn(C)c4)cc23)cc1] |
| 3 | 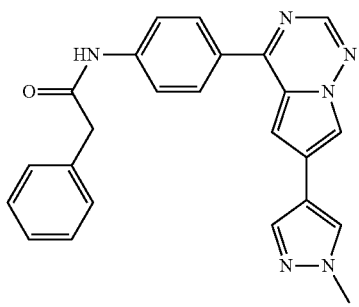 [SMILES: Cn1cc(-c2cc3c(-c4ccc(NC(=O)Cc5ccccc5)cc4)ncnn3c2)cn1] |
| 4 | 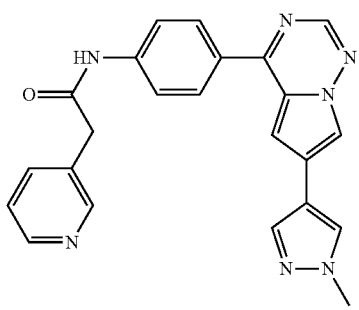 [SMILES: Cn1cc(-c2cc3c(-c4ccc(NC(=O)Cc5cccnc5)cc4)ncnn3c2)cn1] |
| 5 | 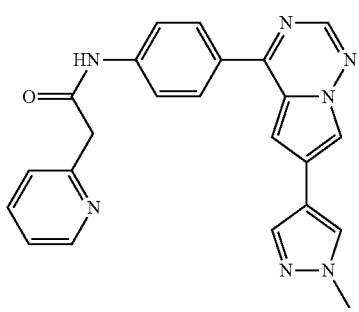 [SMILES: Cn1cc(-c2cc3c(-c4ccc(NC(=O)Cc5ccccn5)cc4)ncnn3c2)cn1] |

-continued
| Compound Number | Structure |
|---|---|
| 6 | 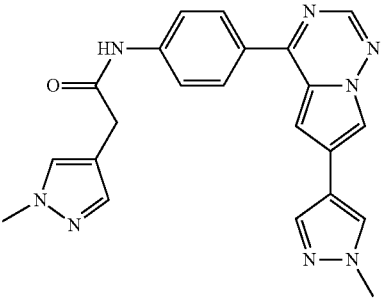 |
| 7 | 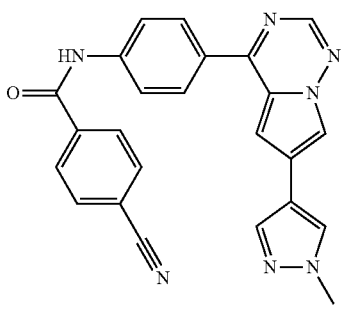 [SMILES: Cn1cc(-c2cc3c(-c4ccc(NC(=O)c5ccc(C#N)cc5)cc4)ncnn3c2)cn1] |
| 8 | 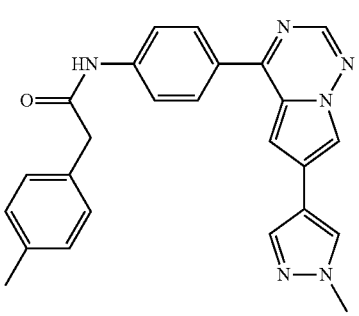 [SMILES: Cc1ccc(CC(=O)Nc2ccc(-c3ncnn4cc(-c5cnn(C)c5)cc34)cc2)cc1] |
| 9 | 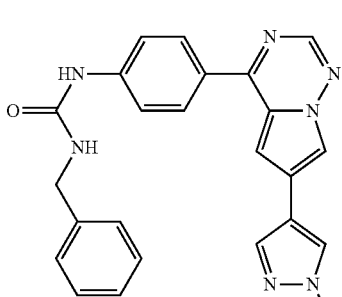 |
| 10 | 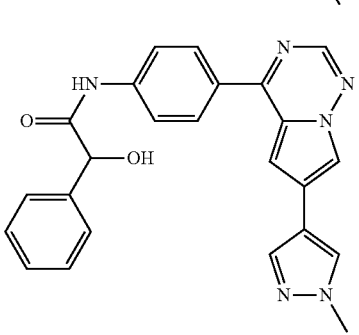 |
-continued
| Compound Number | Structure |
|---|---|
| 11 | 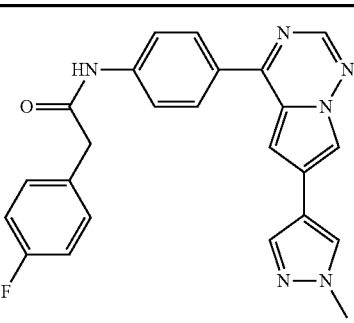 |
| 12 | 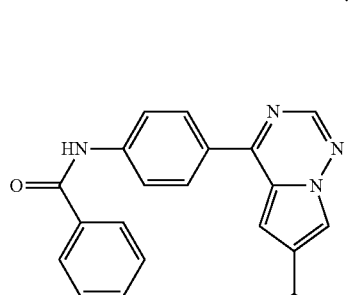 |
| 13 | 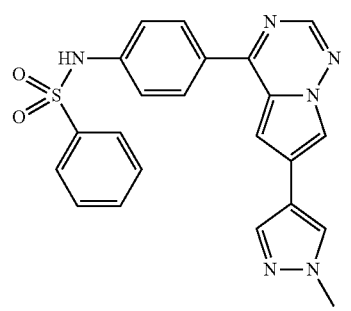 [SMILES: Cn1cc(-c2cc3c(-c4ccc(NS(=O)(=O)c5ccccc5)cc4)ncnn3c2)cn1] |
| 14 | 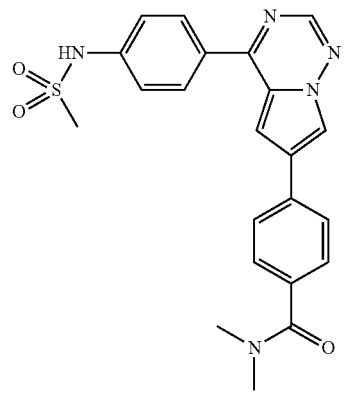 [SMILES: CN(C)C(=O)c1ccc(-c2cc3c(-c4ccc(NS(C)(=O)=O)cc4)ncnn3c2)cc1] |

| Compound Number | Structure |
|---|---|
| 15 | 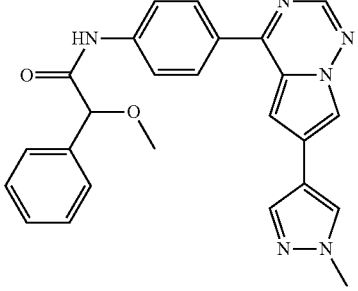 |
| 16 | 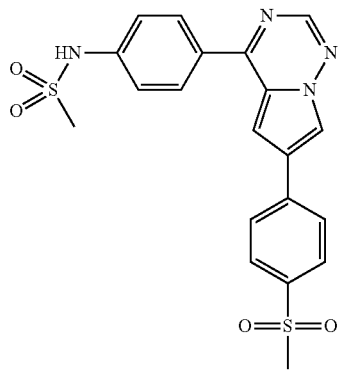 [SMILES: CS(=O)(=O)Nc1ccc(-c2ncnn3cc(-c4ccc(S(C)(=O)=O)cc4)cc23)cc1] |
| 17 | 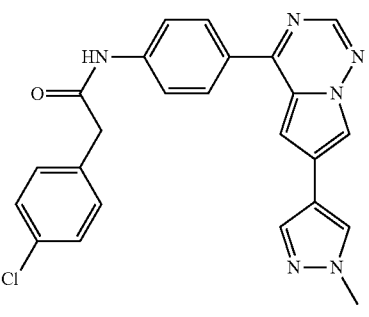 [SMILES: Cn1cc(-c2cc3c(-c4ccc(NC(=O)Cc5ccc(Cl)cc5)cc4)ncnn3c2)cn1] |
| 18 | 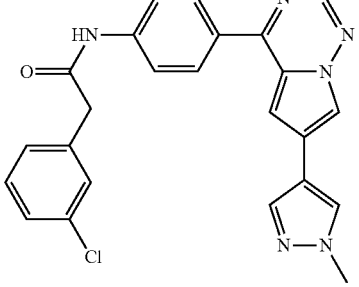 |
| 19 | 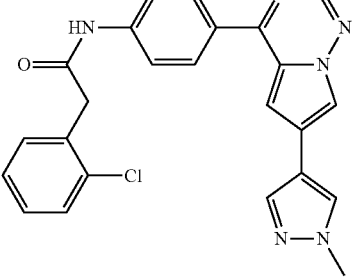 |
| 20 | 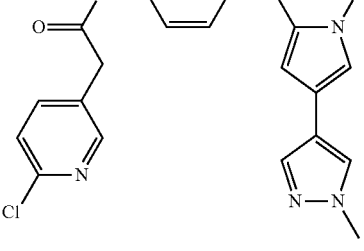 |
| 21 | 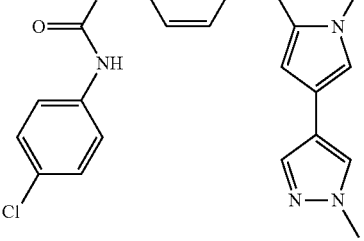 |
| 22 | 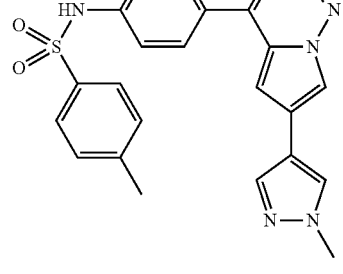 |
| 23 | 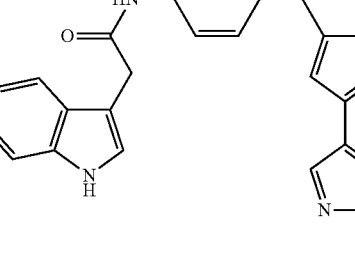 |

-continued
| Compound Number | Structure |
|---|---|
| 24 | 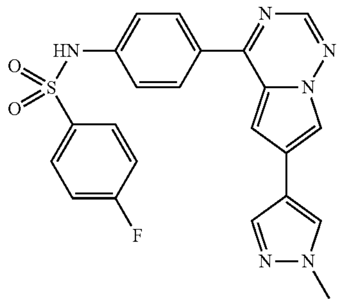 [SMILES: Cc1ccc(S(=O)(=O)Nc2ccc(-c3ncnn4cc(-c5cnn(C)c5)cc34)cc2)cc1] |
| 25 | 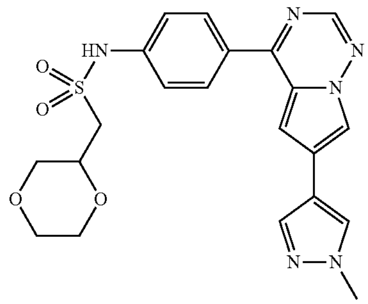 [SMILES: Cn1cc(-c2cc3c(-c4ccc(NS(=O)(=O)CC5COCCO5)cc4)ncnn3c2)cn1] |
| 26 | 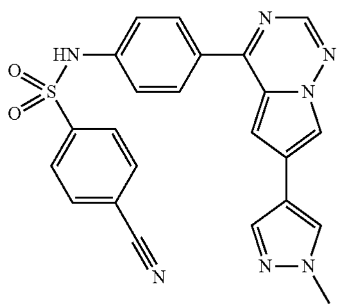 [SMILES: Cn1cc(-c2cc3c(-c4ccc(NS(=O)(=O)c5ccc(C#N)cc5)cc4)ncnn3c2)cn1] |
| 27 | 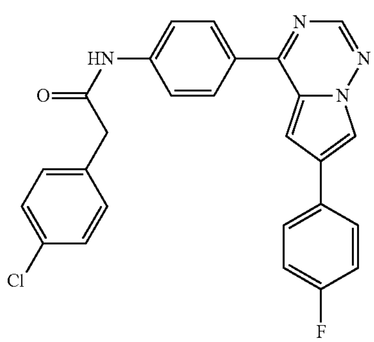 [SMILES: O=C(Cc1ccc(Cl)cc1)Nc1ccc(-c2ncnn3cc(-c4ccc(F)cc4)cc23)cc1] |
| 28 | 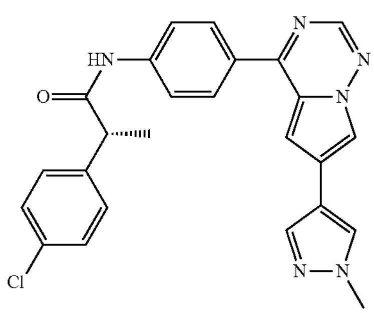 [SMILES: C[C@@H](C(=O)Nc1ccc(-c2ncnn3cc(-c4cnn(C)c4)cc23)cc1)c1ccc(Cl)cc1] |
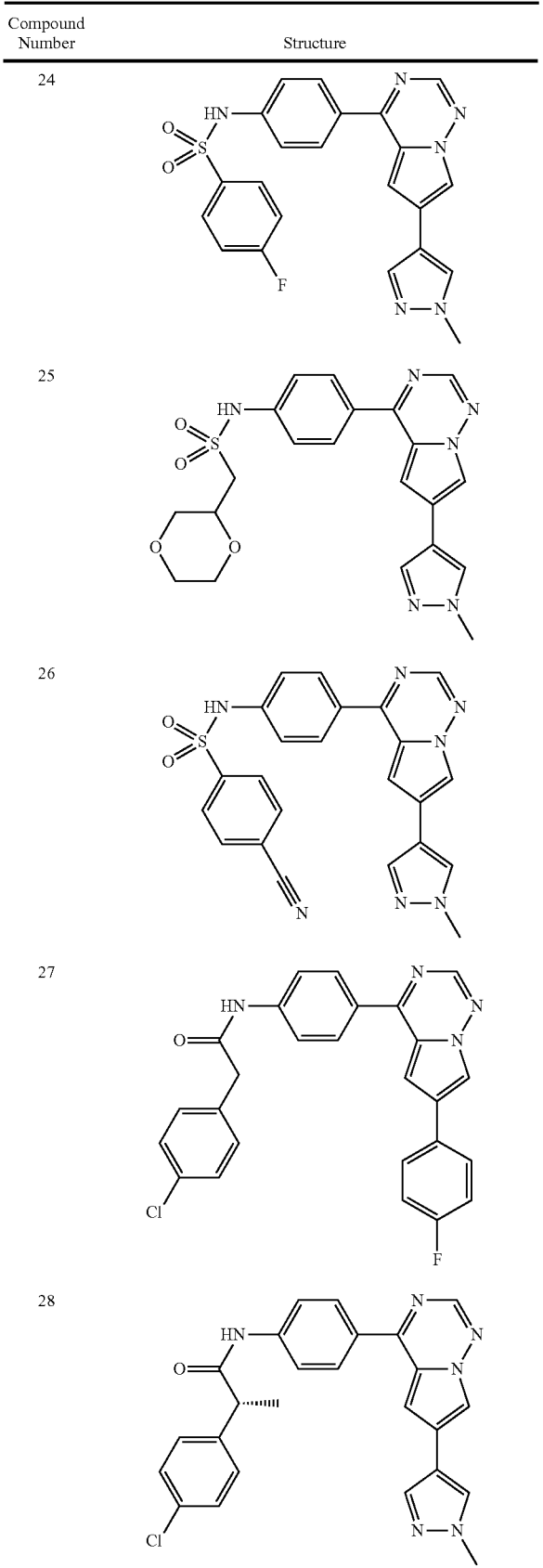
-continued
| Compound Number | Structure |
|---|---|
| 29 | 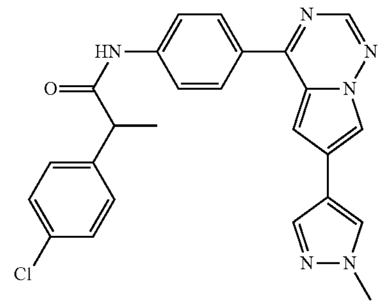 [SMILES: CC(C(=O)Nc1ccc(-c2ncnn3cc(-c4cnn(C)c4)cc23)cc1)c1ccc(Cl)cc1] |
| 30 | 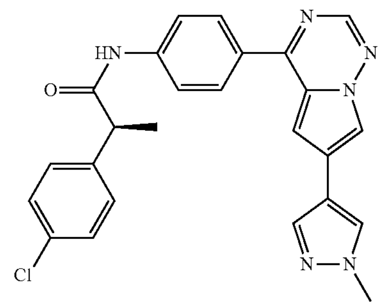 [SMILES: C[C@H](C(=O)Nc1ccc(-c2ncnn3cc(-c4cnn(C)c4)cc23)cc1)c1ccc(Cl)cc1] |
| 31 | 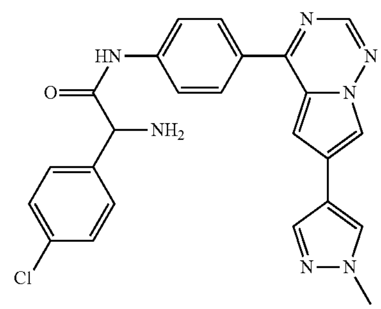 |
| 32 | 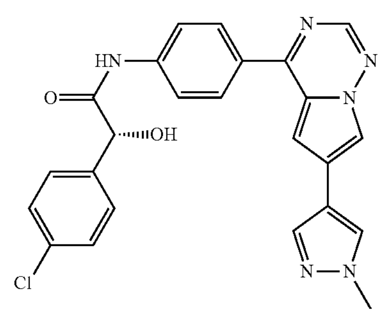 [SMILES: Cn1cc(-c2cc3c(-c4ccc(NC(=O)[C@H](O)c5ccc(Cl)cc5)cc4)ncnn3c2)cn1] |
| 33 | 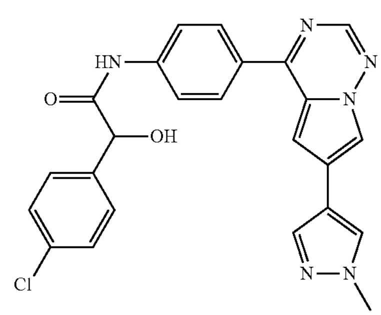 [SMILES: Cn1cc(-c2cc3c(-c4ccc(NC(=O)C(O)c5ccc(Cl)cc5)cc4)ncnn3c2)cn1] |
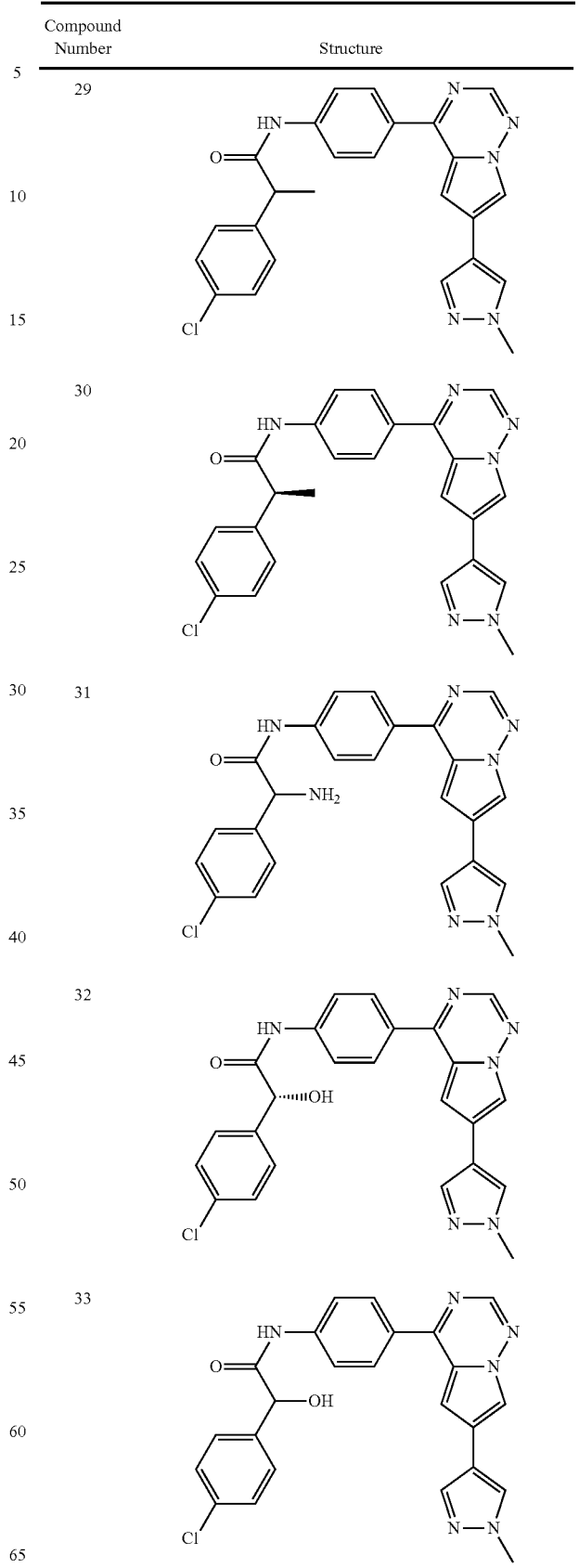

-continued

| Compound Number | Structure |
|---|---|
| 34 | 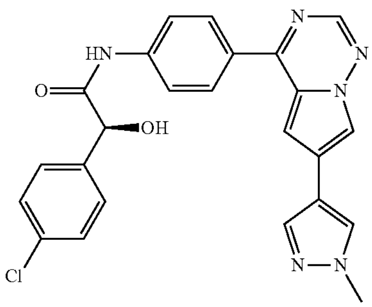 [SMILES: Cn1cc(-c2cc3c(-c4ccc(NC(=O)[C@@H](O)c5ccc(Cl)cc5)cc4)ncnn3c2)cn1] |
| 35 | 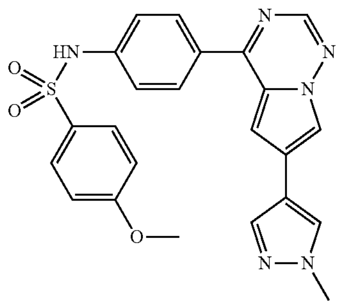 [SMILES: COc1ccc(S(=O)(=O)Nc2ccc(-c3ncnn4cc(-c5cnn(C)c5)cc34)cc2)cc1] |
| 36 | 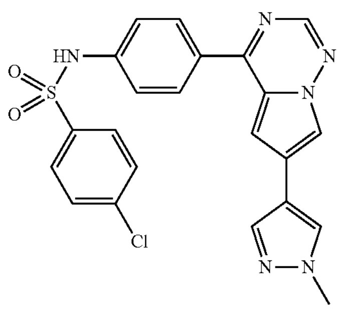 [SMILES: Cn1cc(-c2cc3c(-c4ccc(NS(=O)(=O)c5ccc(Cl)cc5)cc4)ncnn3c2)cn1] |
| 37 | 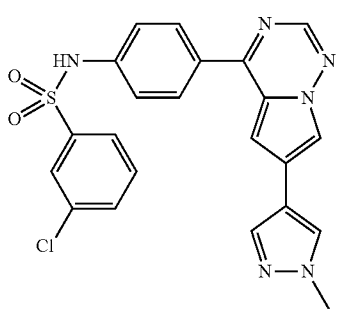 [SMILES: Cn1cc(-c2cc3c(-c4ccc(NS(=O)(=O)c5cccc(Cl)c5)cc4)ncnn3c2)cn1] |
| 38 | 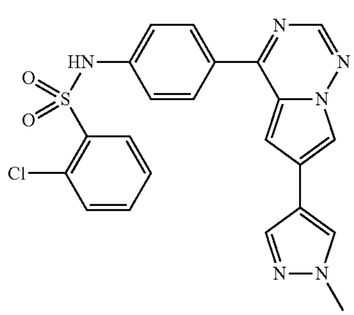 [SMILES: Cn1cc(-c2cc3c(-c4ccc(NS(=O)(=O)c5ccccc5Cl)cc4)ncnn3c2)cn1] |

-continued

| Compound Number | Structure |
|---|---|
| 39 | 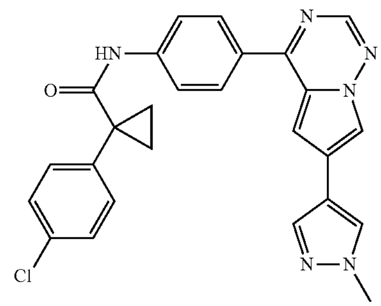 [SMILES: Cn1cc(-c2cc3c(-c4ccc(NC(=O)C5(c6ccc(Cl)cc6)CC5)cc4)ncnn3c2)cn1] |
| 40 | 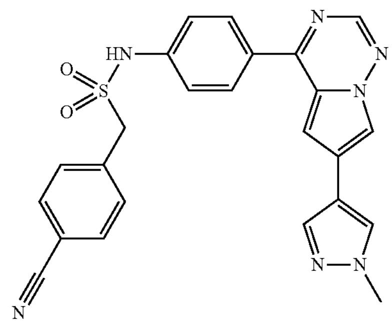 [SMILES: Cn1cc(-c2cc3c(-c4ccc(NS(=O)(=O)Cc5ccc(C#N)cc5)cc4)ncnn3c2)cn1] |
| 41 | 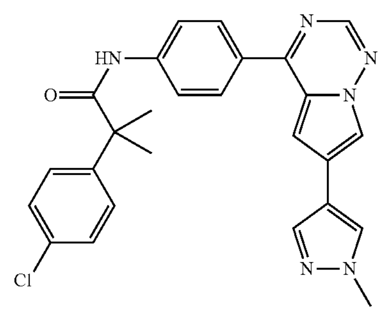 [SMILES: Cn1cc(-c2cc3c(-c4ccc(NC(=O)C(C)(C)c5ccc(Cl)cc5)cc4)ncnn3c2)cn1] |
| 42 | 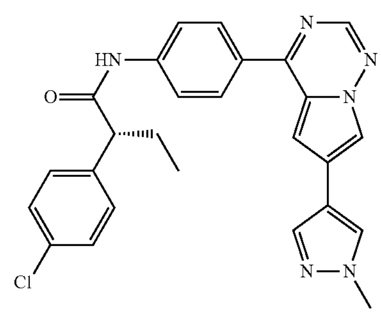 [SMILES: CC[C@@H](C(=O)Nc1ccc(-c2ncnn3cc(-c4cnn(C)c4)cc23)cc1)c1ccc(Cl)cc1] |
| 43 | 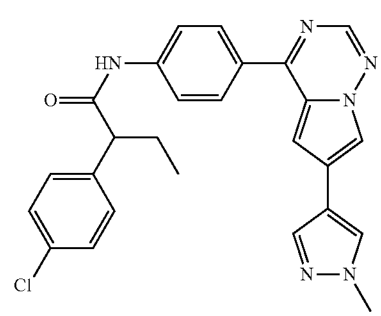 [SMILES: CCC(C(=O)Nc1ccc(-c2ncnn3cc(-c4cnn(C)c4)cc23)cc1)c1ccc(Cl)cc1] |

-continued
| Compound Number | Structure |
|---|---|
| 44 | 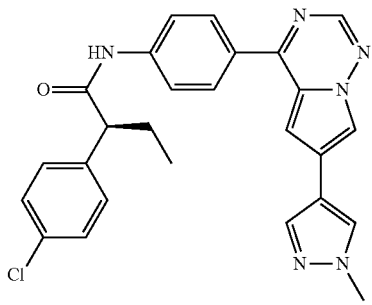 [SMILES: CC[C@H](C(=O)Nc1ccc(-c2ncnn3cc(-c4cnn(C)c4)cc23)cc1)c1ccc(Cl)cc1] |
| 45 | 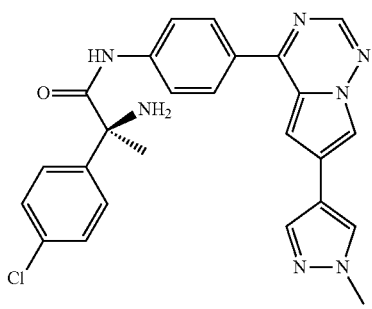 [SMILES: Cn1cc(-c2cc3c(-c4ccc(NC(=O)[C@@](C)(N)c5ccc(Cl)cc5)cc4)ncnn3c2)cn1] |
| 46 | 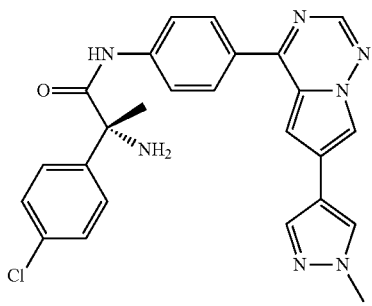 [SMILES: Cn1cc(-c2cc3c(-c4ccc(NC(=O)[C@](C)(N)c5ccc(Cl)cc5)cc4)ncnn3c2)cn1] |
| 47 | 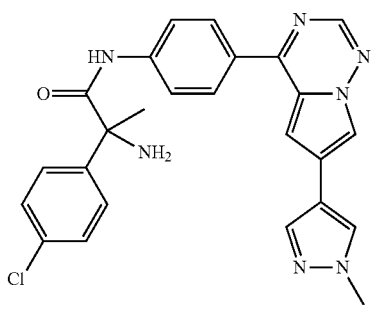 [SMILES: Cn1cc(-c2cc3c(-c4ccc(NC(=O)C(C)(N)c5ccc(Cl)cc5)cc4)ncnn3c2)cn1] |
| 48 | 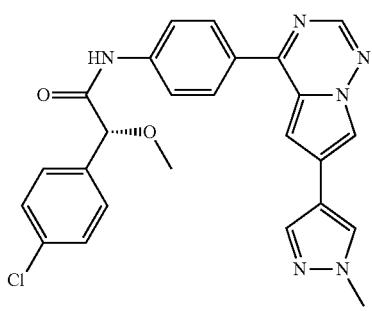 [SMILES: CO[C@@H](C(=O)Nc1ccc(-c2ncnn3cc(-c4cnn(C)c4)cc23)cc1)c1ccc(Cl)cc1] |
-continued
| Compound Number | Structure |
|---|---|
| 49 | 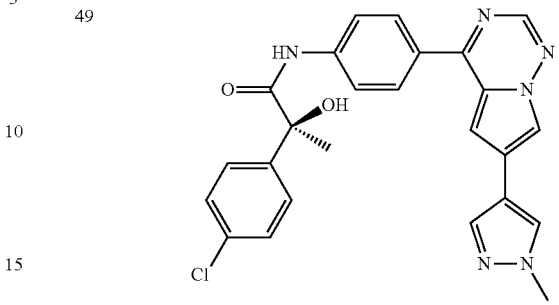 |
| 50 | 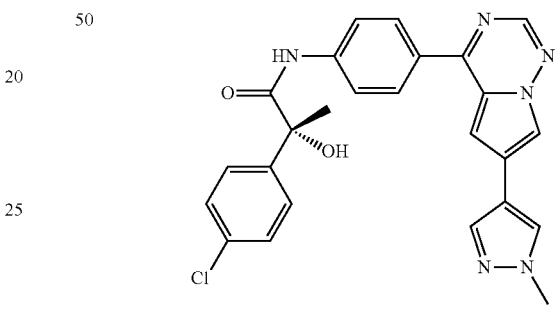 |
| 51 | 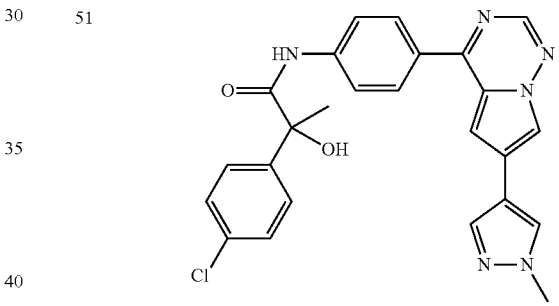 |
| 52 | 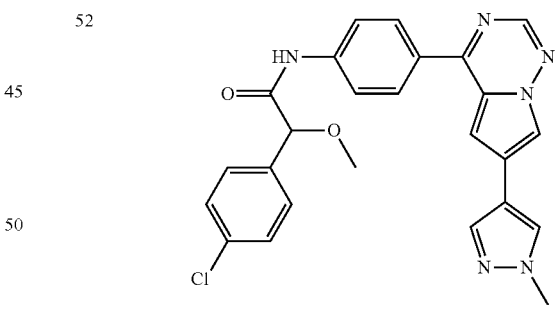 |
| 53 | 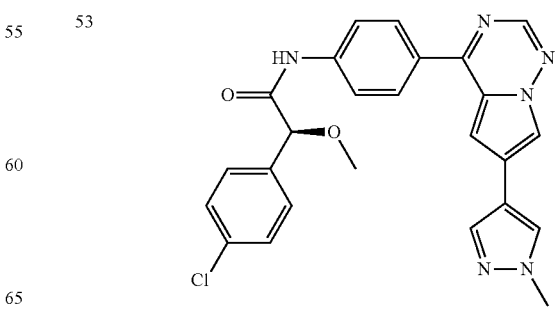 |

-continued
| Compound Number | Structure |
|---|---|
| 54 | 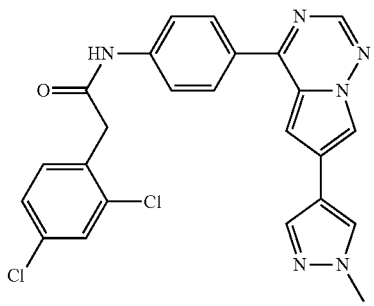 [SMILES: Cn1cc(-c2cc3c(-c4ccc(NC(=O)Cc5ccc(Cl)cc5Cl)cc4)ncnn3c2)cn1] |
| 55 | 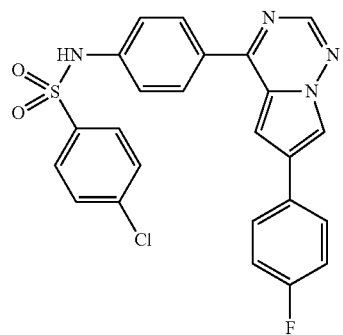 [SMILES: O=S(=O)(Nc1ccc(-c2ncnn3cc(-c4ccc(F)cc4)cc23)cc1)c1ccc(Cl)cc1] |
| 56 | 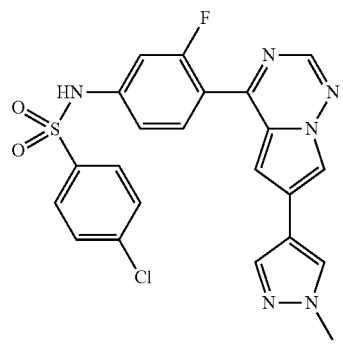 [SMILES: Cn1cc(-c2cc3c(-c4ccc(NS(=O)(=O)c5ccc(Cl)cc5)cc4F)ncnn3c2)cn1] |
| 57 | 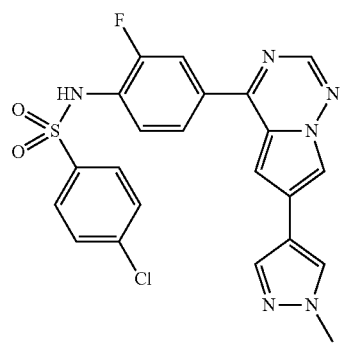 [SMILES: Cn1cc(-c2cc3c(-c4ccc(NS(=O)(=O)c5ccc(Cl)cc5)c(F)c4)ncnn3c2)cn1] |
-continued
| Compound Number | Structure |
|---|---|
| 58 | 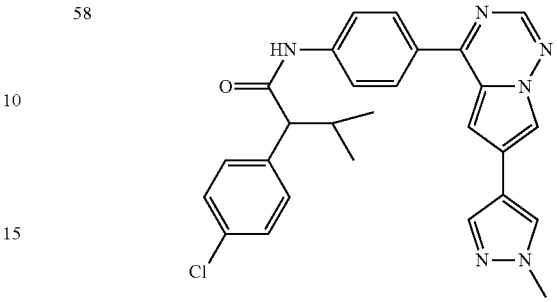 |
| 59 | 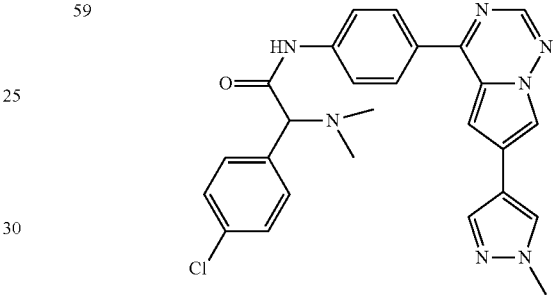 |
| 60 | 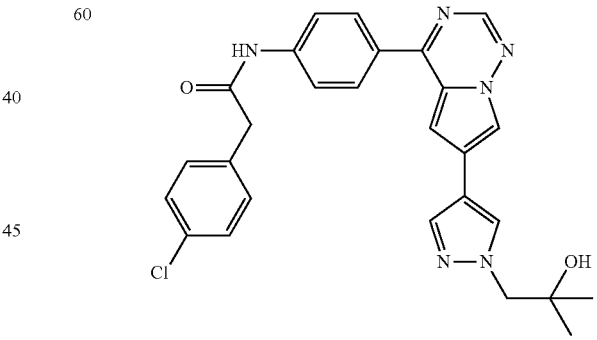 |
| 61 | 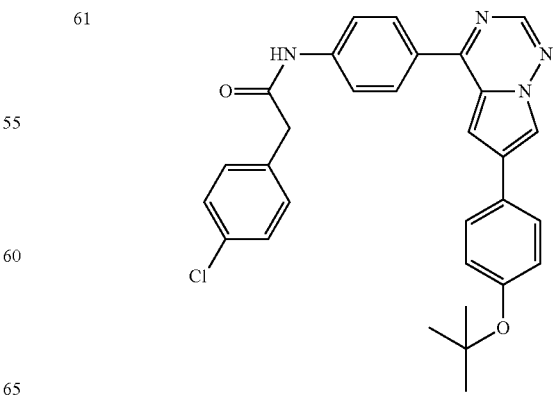 |

| Compound Number | Structure |
|---|---|
| 62 | (structure) |
| 63 | (structure) |
| 64 | (structure) |
| 65 | (structure) |
| 66 | (structure) |

Pharmaceutically acceptable salts of these compounds are also contemplated for the uses described herein.

"Pharmaceutically acceptable salt" refers to any salt of a compound of the invention which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Indications

The compounds described herein can be useful for treating conditions associated with aberrant KIT activity, in humans or non-humans. Activating mutations in KIT are found in multiple indications, including systemic mastocytosis, GIST (gastrointestinal stromal tumors), AML (acute myeloid leukemia), melanoma, seminoma, intercranial germ cell tumors, and mediastinal B-cell lymphoma.

Mastocytosis refers to a group of disorders characterized by excessive mast cell accumulation in one tissue, or in multiple tissues. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. SM is further subdivided into five forms: indolent (ISM), smoldering (SSM), aggressive (ASM), SM with associated hemotologic non-mast cell lineage disease (SM-AHNMD), and mast cell leukemia (MCL).

Diagnosis of systemic mastocytosis is based in part on histological and cytological studies of bone marrow showing infiltration by mast cells of frequently atypical morphology, which frequently abnormally express non-mast cell markers (CD25 and/or CD2). Diagnosis of SM is confirmed when bone marrow mast cell infiltration occurs in the context of one of the following: (1) abnormal mast cell morphology (spindle-shaped cells); (2) elevated level of serum tryptase above 20 ng/mL; or (3) the presence of the activating KIT D816V mutation.

Activating mutations at the D816 position are found in the vast majority of mastocytosis cases (90-98%), with the most common mutations being D816V and D816H, and D816Y. The D816V mutation is found in the activation loop of the kinase domain, and leads to constitutive activation of KIT kinase.

The compounds described herein may also be useful to treat GIST. Complete surgical resection remains the principal treatment of choice for patients with a primary GIST. Surgery is effective in approximately 50% of patients with GIST; of the remaining patients, tumor recurrence is frequent. Primary treatment with a KIT inhibitor such as imatinib has also been shown to be sufficient for initial treatment. However, resistance to imatinib occurs within months through somatic mutation. These secondary imatinib resistant mutations are most frequently located on Exon 11, 13, 14, 17 or 18. Sunitinib is the standard of care second line treatment for most imatinib resistant tumors and is effective for those containing mutations in exons 11, 13 and 14. However, secondary KIT mutations in exons 17 and 18 are resistant to sunitinib treatment and furthermore, tumors containing tertiary resistance mutations in exon 17 and 18 emerge several months after sunitinib treatment. Regorafenib has shown promising results in a phase 3 clinical trial of imatinib, sunitinib resistant GISTs with activity against several but not all exon 17 and 18 mutations, of which D816 is one. Thus, there is a need for therapeutic agents to treat GIST patients with exon 17 mutations not addressed by regorafenib.

In addition to the use of the compounds described herein as single agents in the refractory GIST setting, the use of combinations of imatinib, sunitinib and/or regorafenib with the compounds disclosed herein may allow for the prevention of emergence of resistance to exon 17 mutations.

There is a subset of GIST patients with a D842V mutation in PDGFRα; this subgroup of GIST patients can be stratified by identifying this mutation. This subset of patients is refractory to all tyrosine kinase inhibitors currently available. The compounds described herein, due to their activity against PDGFRα D842V, can be useful in treating these patients.

The compounds described herein may also be useful in treating AML. AML patients harbor KIT mutations as well, with the majority of these mutations at the D816 position.

In addition, mutations in KIT have been linked to Ewing's sarcoma, DLBCL (diffuse large B cell lymphoma), dysgerminoma, MDS (myelodysplastic syndrome), NKTCL (nasal NK/T-cell lymphoma), CMML (chronic myelomonocytic leukemia), and brain cancers.

The compounds disclosed herein may be used to treat conditions associated with the KIT mutations in Exon 9, Exon 11, Exon 13, Exon 14, Exon 17 and/or Exon 18. They may also be used to treat conditions associated with wild-type KIT. The compounds described herein may be used as single agents to treat the conditions described herein, or they may be used in combination with other therapeutic agents, including, without limitation, imatinib, sunitinib and regorafenib. Other agents include the compounds described in WO 2014/039714 and WO 2014/100620.

Compounds described herein can be active against one or more KIT mutations in Exon 17 (e.g., D816V, D816Y, D816F, D816K, D816H, D816A, D816G, D820A, D820E, D820G, N822K, N822H, Y823D, and A829P), and much less active against wild-type KIT. These compounds can be administered in combination with an agent that is (a) active against other activating mutations of KIT, such as Exon 9 and 11 mutations, but (b) not active against the Exon 17 mutations. Such agents include imatinib, sunitinib, and regorafenib. The combination of the compound and the agent will thus inhibit Exon 17 mutant KIT, as well as inhibiting Exon 9/11 mutant KIT. The compound and agent can be co-administered, or administered in an alternating regimen. That is, the Exon 17 mutant KIT inhibitor can be administered alone for a period of time; then the Exon 9/11 mutant KIT inhibitor can be administered alone for a period of time following. This cycle may then be repeated. It is believed that such a regimen could slow the development of resistance to the Exon 17 mutant KIT inhibitor and/or the Exon 9/11 mutant KIT inhibitor.

In addition, compounds described herein that can be selective for Exon 17 KIT mutations can be administered with agents that are active against Exon 9/11 mutations, in combination with a third agent that covers mutations that are missed with the two-way combo. The combination of the three agents could inhibit a spectrum of KIT mutations, as well as wild-type KIT in some instances. The agents could be administered simultaneously, or in an alternating regimen. They can be administered one at a time, or two agents can be administered together for a period of time; then the third agent can be administered alone for a following period of time. It is believed that such a regimen could slow the development of resistance to the mutant KIT inhibitors.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level and treatment regimen will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, the judgment of the treating physician, the severity of the particular disease being treating and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC).

LC-MS:

Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS:

Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Chiral HPLC:

Preparative HPLC to resolve chiral mixtures was performed on a Thar SFC Pre-80 instrument fitted with a Chiralpak AS-H column (5 mm, 3.0 cm id×25 cm L). The mobile phases consisted of SFC $CO_2$ (A) and MeOH/0.1% $NH_4OH$ (B). A constant gradient from 67% to 33% (B) was maintained at a flow rate of 65 g/min, with a system back pressure of 100 bar. The separation progress was monitored by UV detection at a wavelength of 220 nm.

Silica Gel Chromatography:

Silica gel chromatography was performed on either a Teledyne Isco CombiFlash® Rf unit or a Biotage® Isolera Four unit.

Proton NMR:

Unless otherwise indicated, all $^1H$ NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-$d_6$ solvent as parts-per million (ppm) with respect to residual DMSO (2.50 ppm).

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Protocol 1

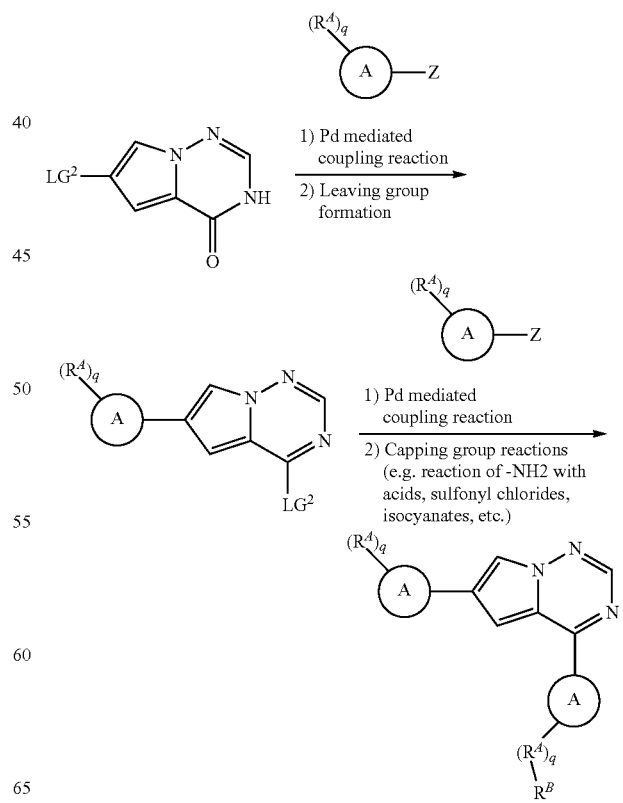

The pyrrolotriazinone can be coupled ($LG^2$ can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide an intermediate with a new carbon-carbon bond formed after subsequent leaving group formation (via $POCl_3$ or other similar reagents). The resulting pyrrolotriazine can be coupled in a similar fashion ($LG^2$ can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide an intermediate with a new carbon-carbon bond. This resulting di-substituted pyrrolotriazine may contain a reactive group (e.g. an amine/aniline) that can be further reacted with groups such as carboxylic acids/acid chlorides, sulfonyl chlorides and isocyanates to form amides, sulfonamides and ureas, respectively, via well-established reaction protocols. As shown below, Compounds 9 and 41 were prepared using Synthetic Protocol 1.

Example 1: Synthesis of 2-(4-chlorophenyl)-2-methyl-N-(4-(6-(1-methyl-1H-pyrazol-4-yl)pyrrolo[1,2-f][1,2,4]triazin-4-yl)phenyl)propanamide (Compound 41)

Step 1: Synthesis of 2-(4-chlorophenyl)-2-methylpropanoyl chloride

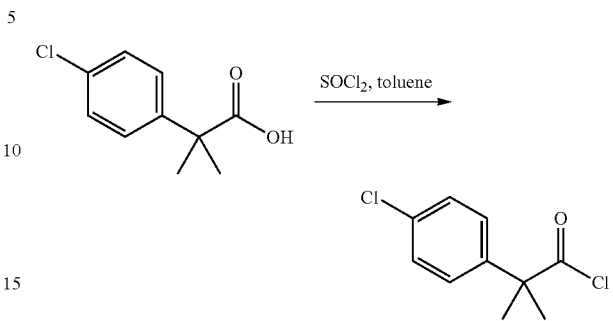

To a solution of 2-(4-chlorophenyl)-2-methylpropanoic acid (200 mg, 0.94 mmol) in toluene (2 mL) was added $SOCl_2$ (0.15 mL, 2.1 mmol) slowly. The solution was then stirred at 80° C. for 2 h, and then concentrated to give 2-(4-chlorophenyl)-2-methylpropanoyl chloride (260 mg, crude) as a pale yellow solid which was used in next step without further purification.

Step 2: Synthesis of 2-(4-chlorophenyl)-2-methyl-N-(4-(6-(1-methyl-1H-pyrazol-4-yl)pyrrolo[1,2-f][1,2,4]triazin-4-yl)phenyl)propanamide

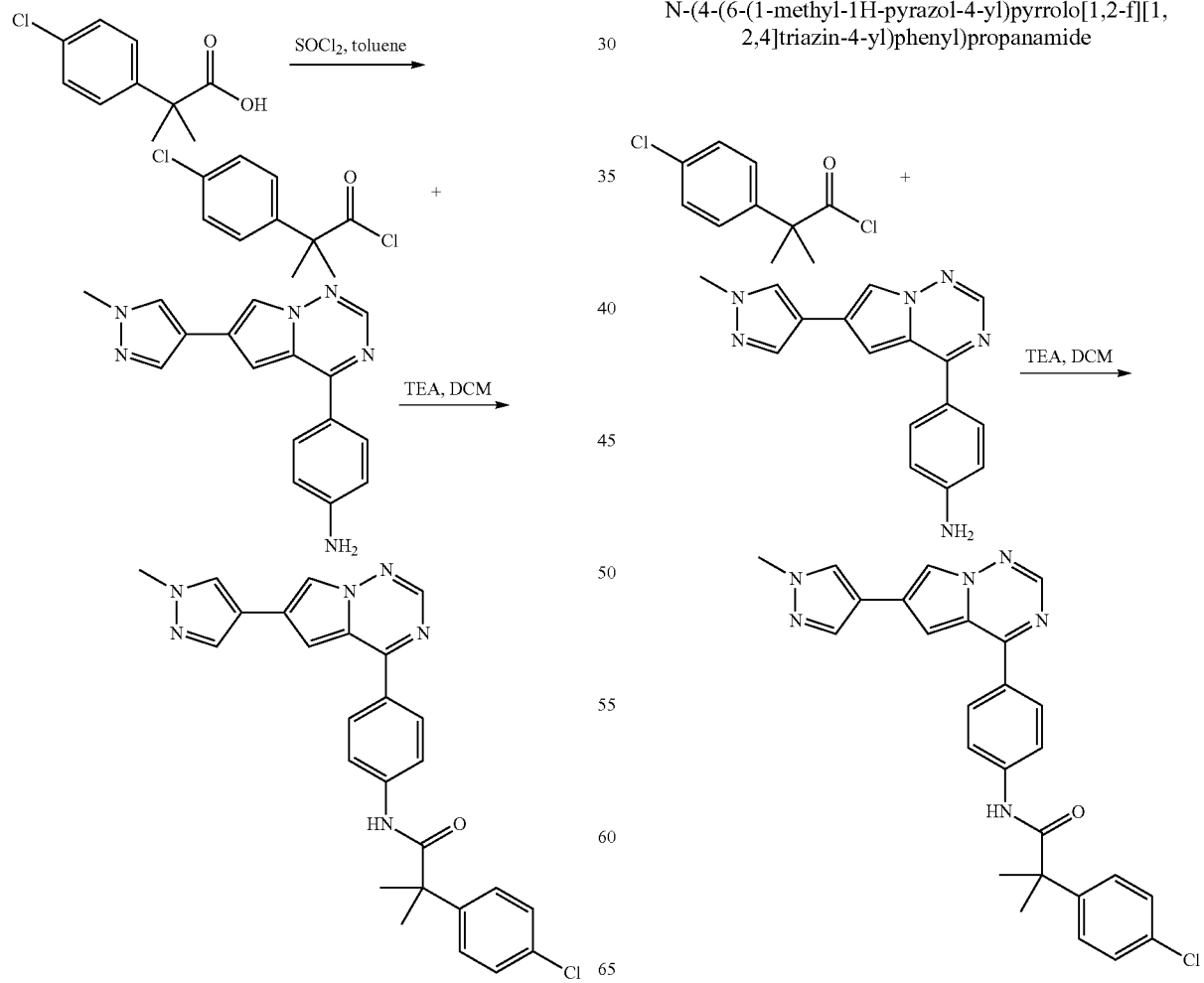

A solution of 2-(4-chlorophenyl)-2-methylpropanoyl chloride (128 mg, 0.55 mmol), TEA (84 mg, 0.83 mmol) and 4-(6-(1-methyl-1H-pyrazol-4-yl)pyrrolo[1,2-f][1,2,4]triazin-4-yl)aniline (80 mg, 0.28 mmol) in DCM (5 mL) was stirred at 25° C. for 12 h. After the reaction was complete, the solution was concentrated and purified by preparative HPLC to afford 2-(4-chlorophenyl)-2-methyl-N-(4-(6-(1-methyl-1H-pyrazol-4-yl)pyrrolo[1,2-f][1,2,4]triazin-4-yl)phenyl)propanamide (42 mg, 31%) as a yellow solid. (MS (ES+) $C_{26}H_{23}ClN_6O$ requires: 470. found: 471[M+H]$^+$.

Example 2: Synthesis of 1-benzyl-3-(4-(6-(1-methyl-1H-pyrazol-4-yl)pyrrolo[1,2-f][1,2,4]triazin-4-yl)phenyl)urea (Compound 9)

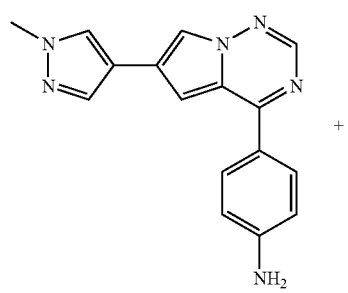

To a solution of 4-(6-(1-methyl-1H-pyrazol-4-yl)pyrrolo[1,2-f][1,2,4]triazin-4-yl)aniline (100 mg, 0.14 mmol), and TEA (103 mg, 1.02 mmol) in THF (10 mL) was added (isocyanatomethyl)benzene (90 mg, 0.68 mmol) at room temperature. The resultant mixture was stirred at 50° C. for 12 h, after which LCMS showed the reaction was complete. The mixture was purified by preparative HPLC to give afford 1-benzyl-3-(4-(6-(1-methyl-1H-pyrazol-4-yl)pyrrolo[1,2-f][1,2,4]triazin-4-yl)phenyl)urea (39.6 mg, 28%) as a yellow solid. MS (ES+) $C_{24}H_{21}N_7O$ requires: 423. found: 424 [M+H]$^+$.

Synthetic Protocol 2

The pyrrolotriazinone can be coupled (LG² can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide an intermediate featuring a new carbon-carbon bond formed after subsequent installation of a leaving group (via POCl₃ or other similar reagents). The resulting pyrrolotriazine can be coupled through a similar process (LG² can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide the product with a new carbon-carbon bond. The second boron, tin or zinc reagent can be formed by elaboration of a simpler reagent via reaction with groups such as carboxylic acids/ acid chlorides, sulfonyl chlorides and isocyanates to form amides, sulfonamides and ureas, respectively, via well-established reaction protocols; and finally Pd mediated ke coupling to modify a leaving group to a boron, tin or zinc group. As shown below, Compound 62 was prepared using Synthetic Protocol 2.

Example 3: Synthesis of 4-chloro-N-(4-(6-(4-isopropoxyphenyl)pyrrolo[2,1-f][1,2,4]triazin-4-yl)phenyl)benzenesulfonamide (Compound 62)

Step 1: Synthesis of 6-(4-isopropoxyphenyl)pyrrolo[2,1-f][1,2,4]triazin-4-ol

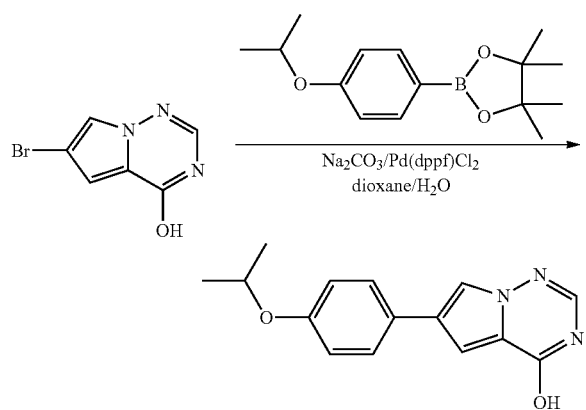

To a solution of 6-bromopyrrolo[2,1-f][1,2,4]triazin-4-ol (1.0 g, 4.69 mmol) in 1,4-dioxane/H₂O (40 mL/8 mL) was added Na₂CO₃ (994 mg, 9.39 mmol), 2-(4-isopropoxyphenyl)-4,4,5,5-tetramethyl-1,3,2-dioxaborolane (970 mg, 5.63 mmol), and Pd(dppf)Cl₂ (100 mg). The reaction was stirred at 110° C. overnight under N₂, after which LCMS showed that the reaction was complete. The reaction mixture was filtered and the solvents were evaporated to give the crude product, which was purified by preparative TLC (PE/EtOAc=1/1) to give 6-(4-isopropoxyphenyl)pyrrolo[2,1-f][1,2,4]triazin-4-ol (250 mg, yield: 19.8%) as a yellow solid. ¹H-NMR (400 MHz, CDCl₃) δ ppm 7.60 (d, 1H, J=2.0 Hz), 7.43 (d, 2H, J=8.4 Hz), 7.38 (d, 1H, J=2.0 Hz), 7.22 (d, 1H, J=1.6 Hz), 7.02 (s, 1H), 6.87 (d, 2H, J=8.8 Hz), 4.54-4.48 (m, 1H), 1.29 (d, 6H, J=6.0 Hz).

Step 2: Synthesis of 4-chloro-6-(4-isopropoxyphenyl)pyrrolo[2,1-f][1,2,4]triazine

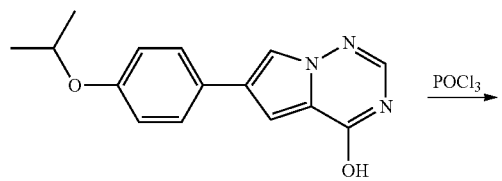

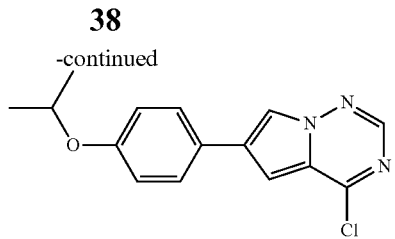

A solution of 6-(4-isopropoxyphenyl)pyrrolo[2,1-f][1,2,4]triazin-4-ol (250 mg, 7.44 mmol) in POCl₃ (10 mL) was stirred at 80° C. for 5 hrs. After LCMS showed that the reaction was complete, the reaction mixture was evaporated to remove POCl₃, followed by addition of EtOAc (100 mL) at 0° C. and water. The aqueous layer was extracted with EtOAc (30 mL*3), then the combined organic layer was washed with brine, dried over Na₂SO₄, and concentrated to give the crude 4-chloro-6-(4-isopropoxyphenyl)pyrrolo[2,1-f][1,2,4]triazine (200 mg, yield: 74.6%). The compound was used in the next step without further purification.

Step 3: Synthesis of N-(4-bromophenyl)-4-chlorobenzenesulfonamide

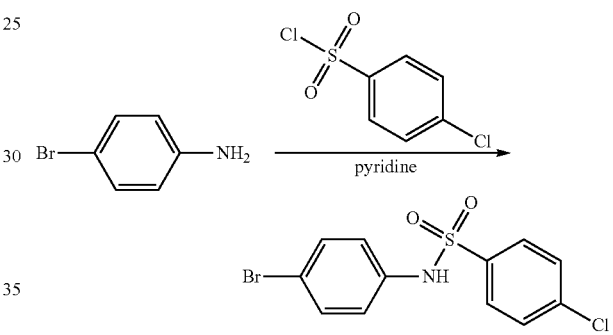

To the solution of 4-chloro-6-(4-isopropoxyphenyl)pyrrolo[2,1-f][1,2,4]triazine (6.00 g, 35.1 mmol) in pyridine (50 mL) was added 4-chlorobenzene-1-sulfonyl chloride (8.84 g, 42.1 mmol) at 0° C. After addition, the solution was stirred at 27° C. overnight. When the reaction was complete as indicated by TLC (PE:EtOAc=5:1) and LCMS, the solvent was concentrated in vacuo to give the crude product, which was purified by column chromatography on silica gel to afford N-(4-bromophenyl)-4-chlorobenzenesulfonamide (10.5 g, yield: 86.8%). ¹H-NMR (400 MHz, CDCl₃) δ ppm 7.67 (d, 2H, J=8.4 Hz), 7.41 (d, 2H, J=8.4 Hz), 7.36 (d, 2H, J=8.8 Hz), 6.94 (d, 2H, J=8.4 Hz), 6.74 (s, 1H).

Step 4: Synthesis of 4-chloro-N-(4-(4,4,5,5-tetramethyl-1,3,2-dioxaborolan-2-yl)phenyl)benzenesulfonamide

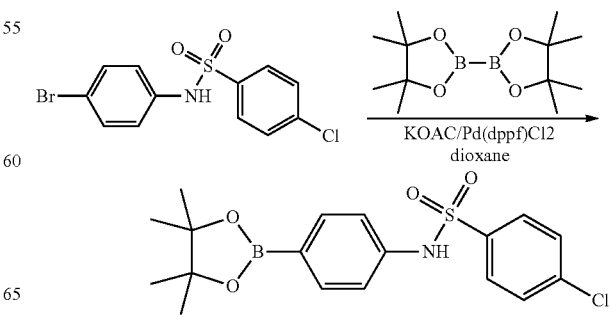

To a solution of N-(4-bromophenyl)-4-chlorobenzenesulfonamide (10.5 g, 30.4 mmol) in dioxane was added 4,4,4',4',5,5,5',5'-octamethyl-2,2'-bi(1,3,2-dioxaborolane (7.73 g, 30.4 mmol), KOAc (7.45 g, 76.0 mmol), and Pd(dppf)Cl$_2$ (1.5 g). The mixture was stirred at 110° C. under N$_2$ overnight. Once the reaction was complete as indicated by LCMS, the mixture was filtered and the filter cake was washed by EtOAC (10 mL*3). The combined filtrate was concentrated in vacuo to give the crude product which was purified by column chromatography on silica gel to afford 4-chloro-N-(4-(4,4,5,5-tetramethyl-1,3,2-dioxaborolan-2-yl)phenyl)benzenesulfonamide (9.50 g, yield: 79.2%) as an orange solid. $^1$H-NMR (400 MHz, CDCl$_3$) δ ppm 7.63 (t, 4H, J=9.2 Hz), 7.32 (d, 2H, J=8.4 Hz), 6.99 (d, 2H, J=8.4 Hz), 6.78 (s, 1H), 1.25 (s, 12H).

Step 5: Synthesis of 4-chloro-N-(4-(6-(4 isopropoxyphenyl)pyrrolo[2,1-f][1,2,4]triazin-4-yl)phenyl)benzenesulfonamide

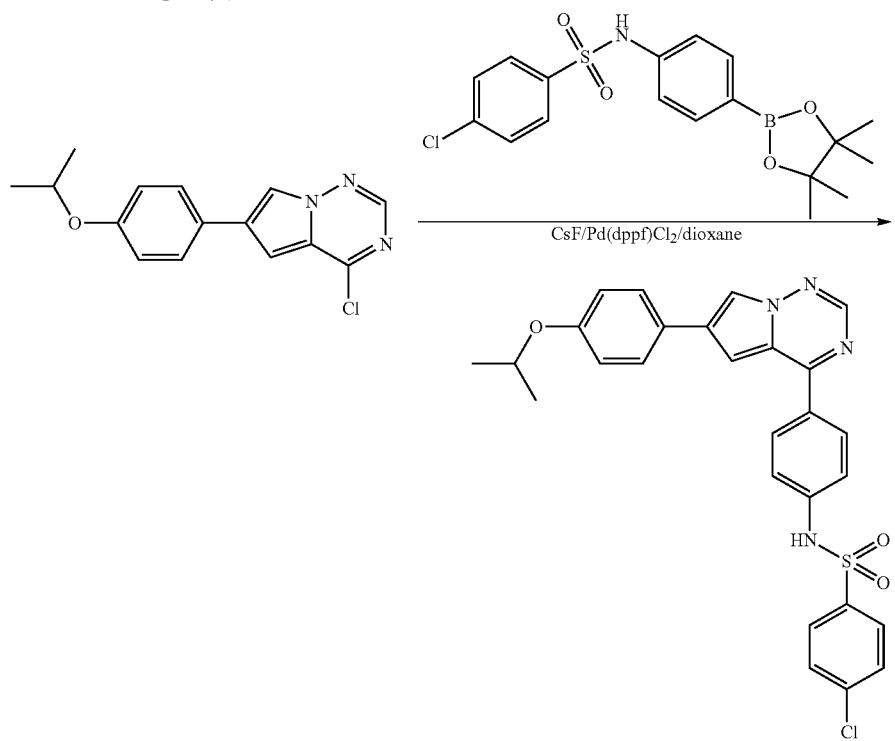

To a solution of 4-chloro-6-(4-isopropoxyphenyl)pyrrolo[2,1-f][1,2,4]triazine (70 mg, 0.242 mmol) in 1,4-dioxane (10 mL) was added CsF (74 mg, 0.484 mmol), 4-chloro-N-(4-(4,4,5,5-tetramethyl-1,3,2-dioxaborolan-2-yl)phenyl)benzenesulfonamide (95 mg, 0.242 mmol), and Pd(dppf)Cl$_2$ (10 mg). The reaction was stirred at 110° C. overnight under N$_2$. After LCMS showed that the reaction was complete, the reaction mixture was filtered and the solvents were evaporated to give the crude product, which was purified by preparative HPLC to give 4-chloro-N-(4-(6-(4-isopropoxyphenyl)pyrrolo[2,1-f][1,2,4]triazin-4-yl)phenyl)benzenesulfonamide (2.8 mg, yield: 2.2%) as a yellow solid.

LC-MS (mobile phase: from 75% [water+0.375% v/v TFA] and 25% [CH$_3$CN+0.188% v/v TFA], for 0.4 min, then changed to 100% [CH$_3$CN+0.188% v/v TFA] in 3.0 min, under this condition for 0.45 min, and changed to 75% [water+0.375% v/v TFA] and 25% [CH$_3$CN+0.188% v/v TFA] for 0.64 min. Flow rate=0.8 mL/min) 98.953% purity, retention time=3.375 min, MS Calcd.: 519.0. MS Found: 519.2 ([M+1]$^+$).

Synthetic Protocol 3

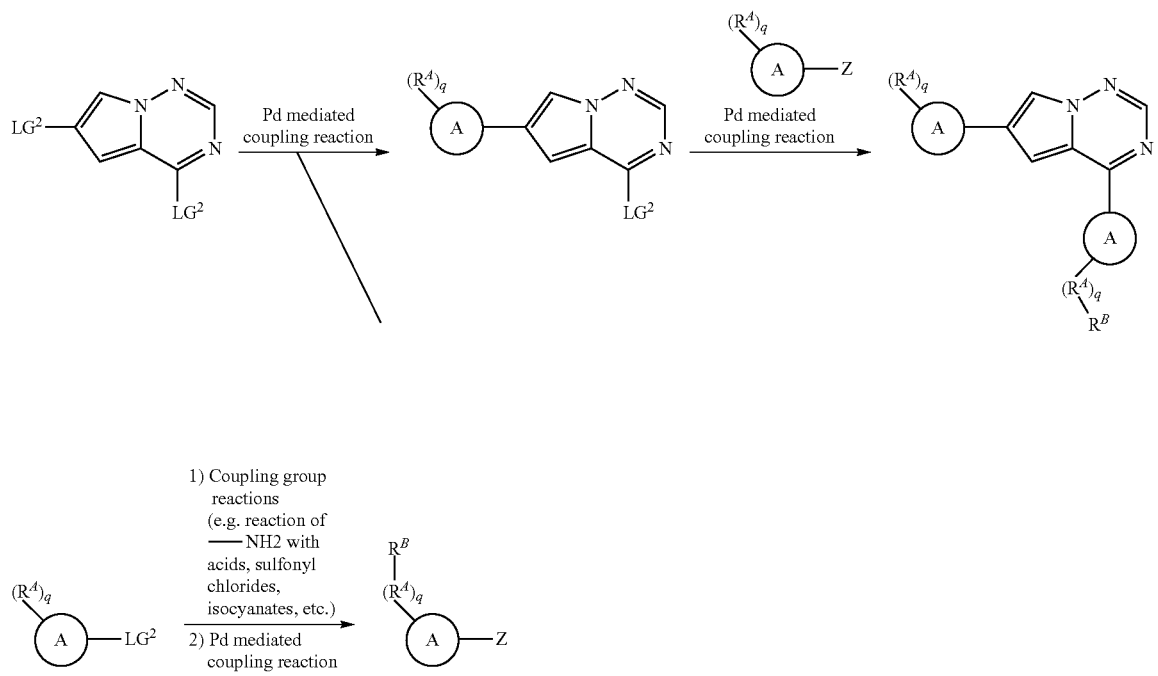

The pyrrolotriazinone (two leaving groups attached) can be selectively coupled (LG$^2$ can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide an intermediate with a new carbon-carbon bond. The boron, tin or zinc reagent can be formed by elaboration of a simpler reagent via reaction with groups such as carboxylic acids/acid chlorides, sulfonyl chlorides and isocyanates to form amides, sulfonamides and ureas, respectively, via well-established reaction protocols, followed by Pd-mediated coupling to modify the leaving group to a boron, tin or zinc group. The resulting pyrrolotriazine can be coupled (LG$^2$ can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide the product featuring new carbon-carbon bond. As shown below, Compound 64 was prepared using Synthetic Protocol 3.

Example 4: Synthesis of ethyl 4-(4-(4-((4-chlorophenyl)sulfonamido)phenyl)pyrrolo[2,1-f][1,2,4]triazin-6-yl)-3,6-dihydropyridine-1(2H)-carboxylate (Compound 64)

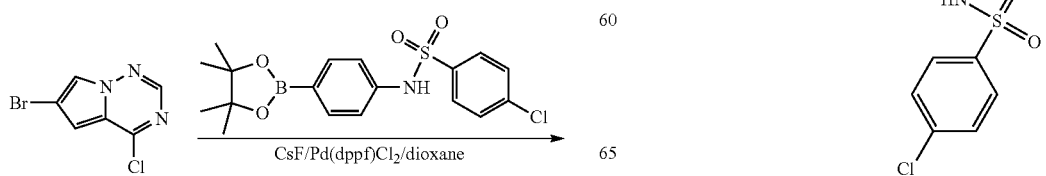

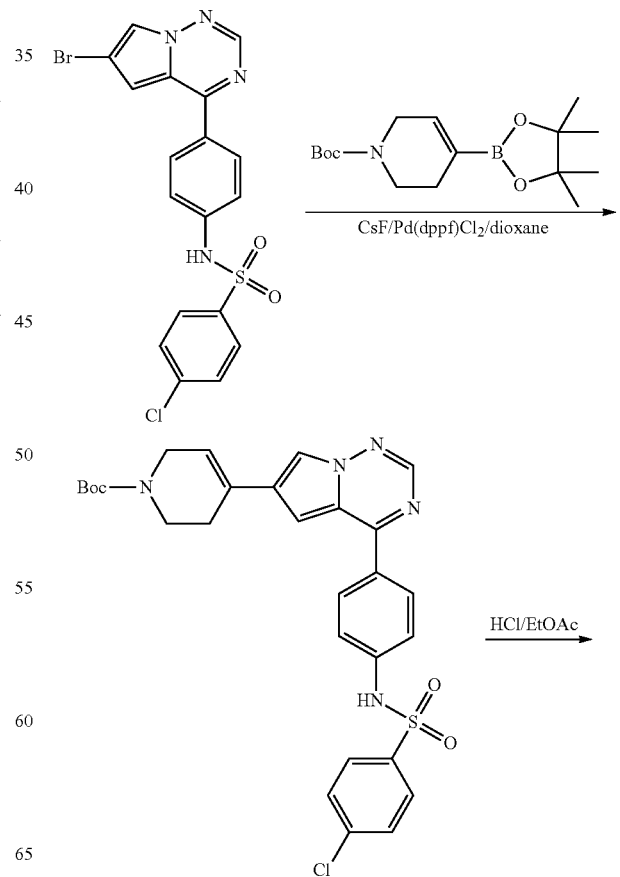

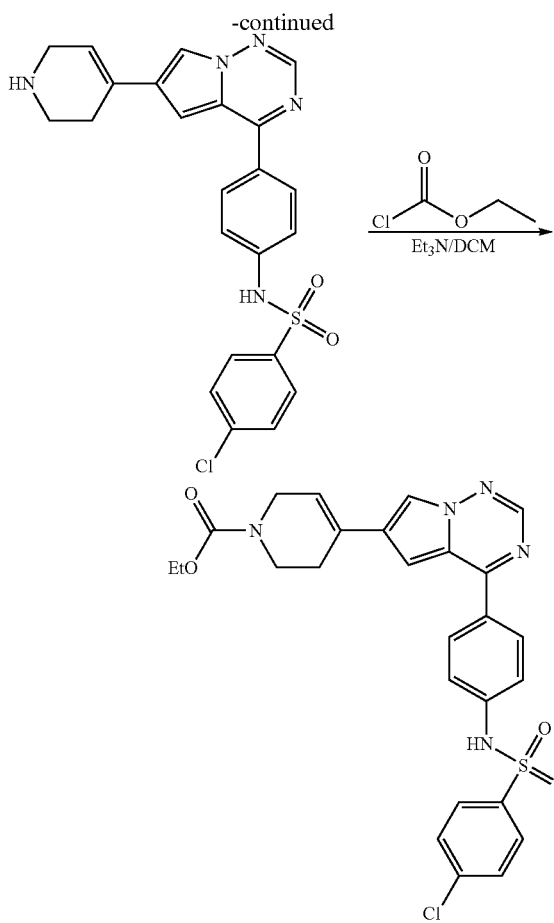

To a solution of 4-chloro-N-(4-(4,4,5,5-tetramethyl-1,3,2-dioxaborolan-2-yl)phenyl)benzenesulfonamide (1.50 g, 6.49 mmol) in dioxane (80 mL) was added 6-bromo-4-chloropyrrolo[2,1-f][1,2,4]triazine (2.55 g, 6.49 mmol), CsF (1.97 g, 2.98 mmol), and Pd(dppf)Cl$_2$ (200 mg). The reaction mixture was stirred at 100° C. under N$_2$ overnight. After LCMS showed the reaction was complete, the mixture was concentrated and the residue purified by column chromatography first on silica, then by acidic preparative HPLC and neutral preparative HPLC to obtain N-(4-(6-bromopyrrolo[2,1-f][1,2,4]triazin-4-yl)phenyl)-4-chlorobenzenesulfonamide (80.0 mg, yield: 2.7%) as a yellow solid. $^1$H-NMR (400 MHz, CD$_3$OD) δ ppm 8.44 (s, 1H), 8.05 (d, 1H, J=1.6 Hz), 8.00 (d, 2H, J=8.8 Hz), 7.84 (d, 2H, J=8.8 Hz), 7.53 (d, 2H, J=8.4 Hz), 7.34 (d, 2H, J=8.8 Hz), 7.19 (s, 1H).

Step 2: Synthesis of tert-butyl 4-(4-(4-((4-chlorophenyl)sulfonamido)phenyl)pyrrolo[2,1-f][1,2,4]triazin-6-yl)-3,6-dihydropyridine-1(2H)-carboxylate

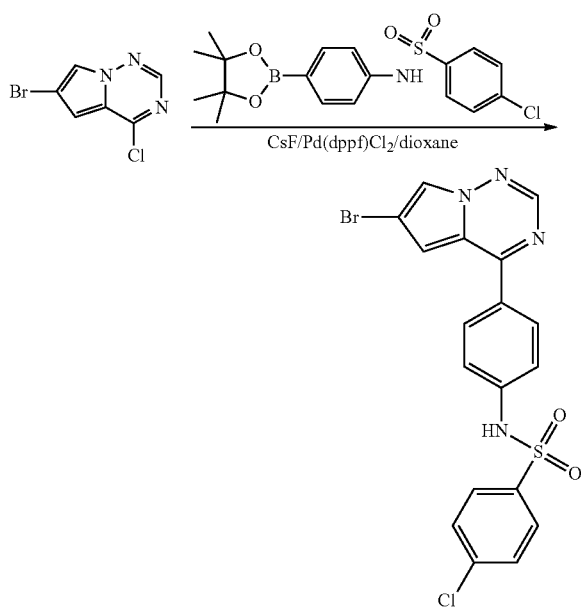

Step 1: Synthesis of N-(4-(6-bromopyrrolo[2,1-f][1,2,4]triazin-4-yl)phenyl)-4-chlorobenzenesulfonamide To a solution of N-(4-(6-bromopyrrolo[2,1-f][1,2,4]triazin-4-yl)phenyl)-4-chlorobenzenesulfonamide (60.0 mg, 0.130 mmol) in dioxane/H$_2$O (5:1, 10 mL) was added tert-butyl 4-(4,4,5,5-tetramethyl-1,3,2-dioxaborolan-2-yl)-5,6-dihydropyridine-1(2H)-carboxylate (48.2 mg, 0.156 mmol), CsF (69.2 mg, 0.260 mmol), and Pd(dppf)Cl$_2$ (20 mg). The reaction mixture was stirred at 90° C. under N$_2$ overnight. Once the LCMS indicated the reaction was complete, the mixture was concentrated and the residue purified by preparative TLC (PE:EtOAc=2:1) to afford tert-butyl 4-(4-(4-((4-chlorophenyl)sulfonamido)phenyl)pyrrolo[2,1- f][1,2,4]triazin-6-yl)-3,6-dihydropyridine-1(2H)-carboxylate (100 mg crude) as a yellow oil. ¹H-NMR (400 MHz, CD₃OD) δ ppm 8.34-8.31 (m, 1H), 7.99-7.97 (m, 2H), 7.85-7.82 (m, 2H), 7.53-7.51 (m, 2H), 7.34-7.32 (m, 2H), 7.14-7.07 (m, 1H), 6.42-6.05 (m, 2H), 4.10-4.06 (m, 2H), 3.70-3.62 (m, 2H), 2.51-2.40 (m, 2H), 1.48 (s, 9H).

Step 3: Synthesis of 4-chloro-N-(4-(6-(1,2,3,6-tetrahydropyridin-4-yl)pyrrolo[2,1-f][1,2,4]triazin-4-yl)phenyl)benzenesulfonamide

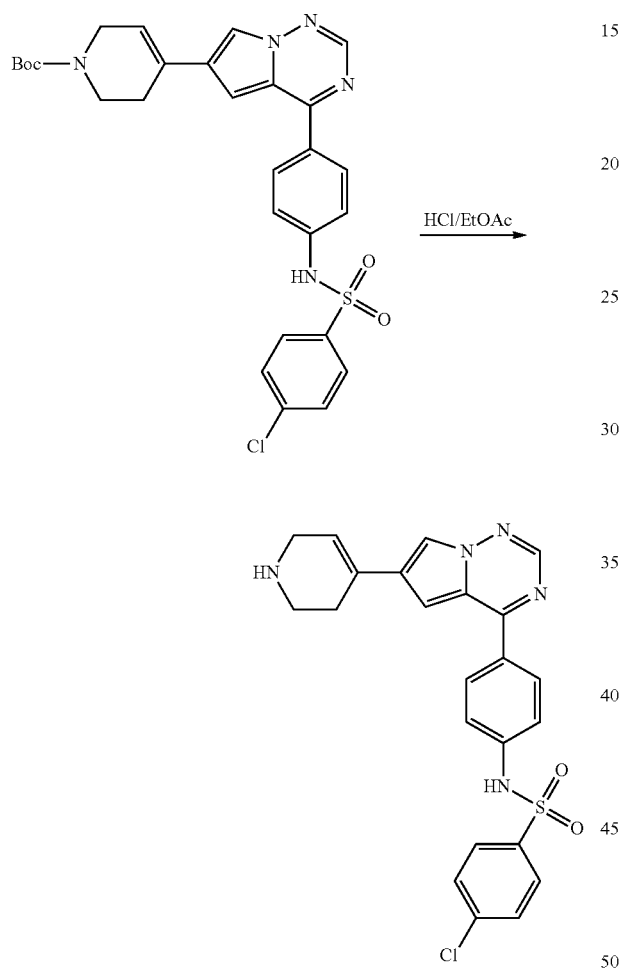

To a solution of tert-butyl 4-(4-(4-((4-chlorophenyl)sulfonamido)phenyl)pyrrolo[2,1-f][1,2,4]triazin-6-yl)-3,6-dihydropyridine-1(2H)-carboxylate (120 mg, 0.212 mmol) in EtOAc (10 mL) was added HCl/EtOAc (10 mL, 4 M) at 25° C. The reaction was stirred at 25° C. for 4 hrs. The solid was then filtered and concentrated to give crude 4-chloro-N-(4-(6-(1,2,3,6-tetrahydropyridin-4-yl)pyrrolo[2,1-f][1,2,4]triazin-4-yl)phenyl)benzenesulfonamide (120 mg crude) as a brown solid. ¹H-NMR (400 MHz, CD₃OD) δ ppm 8.48 (s, 1H), 8.45 (s, 1H), 7.92 (d, 2H, J=8.8 Hz), 7.79 (d, 2H, J=8.8 Hz), 7.48-7.45 (m, 3H), 7.35 (d, 2H, J=8.4 Hz), 6.40 (br.s, 1H), 3.82-3.80 (m, 2H), 3.41-3.39 (m, 2H), 2.80-2.75 (m, 2H).

Step 4: Synthesis of ethyl 4-(4-(4-((4-chlorophenyl)sulfonamido)phenyl)pyrrolo[2,1-f][1,2,4]triazin-6-yl)-3,6-dihydropyridine-1(2H)-carboxylate

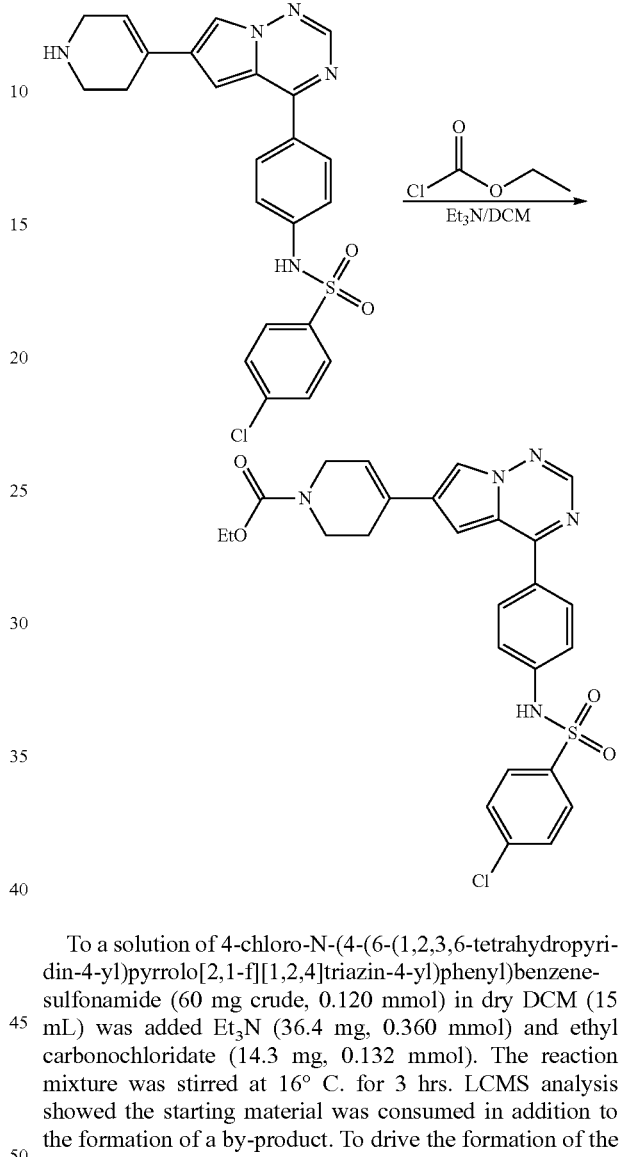

To a solution of 4-chloro-N-(4-(6-(1,2,3,6-tetrahydropyridin-4-yl)pyrrolo[2,1-f][1,2,4]triazin-4-yl)phenyl)benzenesulfonamide (60 mg crude, 0.120 mmol) in dry DCM (15 mL) was added Et₃N (36.4 mg, 0.360 mmol) and ethyl carbonochloridate (14.3 mg, 0.132 mmol). The reaction mixture was stirred at 16° C. for 3 hrs. LCMS analysis showed the starting material was consumed in addition to the formation of a by-product. To drive the formation of the by-product to the desired product, the solvent was removed in vacuo, followed by addition of a mixture of THF/MeOH/H₂O (2/1/1, 10 mL) and NaOH (10 mg), which was stirred at 16° C. overnight. Once LCMS and TLC showed the by-product had been fully converted to the product, the solvent was removed in vacuo and the residue was purified by acidic preparative HPLC to afford ethyl 4-(4-(4-((4-chlorophenyl)sulfonamido)phenyl)pyrrolo[2,1-f][1,2,4]triazin-6-yl)-3,6-dihydropyridine-1(2H)-carboxylate (40.0 mg, yield: 62.2%) as a yellow solid.

LC-MS (mobile phase: 90% [water+0.375% v/v TFA] and 10% [CH₃CN+0.188% v/v TFA] for 0.4 min, then changed to 100% [CH₃CN+0.188% v/v TFA] in 3.0 min, under this condition for 0.45 min, then changed to 90% [water+0.375% v/v TFA] and 10% [CH₃CN+0.188% v/v TFA] for 0.64 min. Flow rate is 0.8 mL/min) 96.226% purity, retention time=2.253, MS Calcd.: 538.0, MS Found: 538.1 ([M+1]⁺).

Synthetic Protocol 4

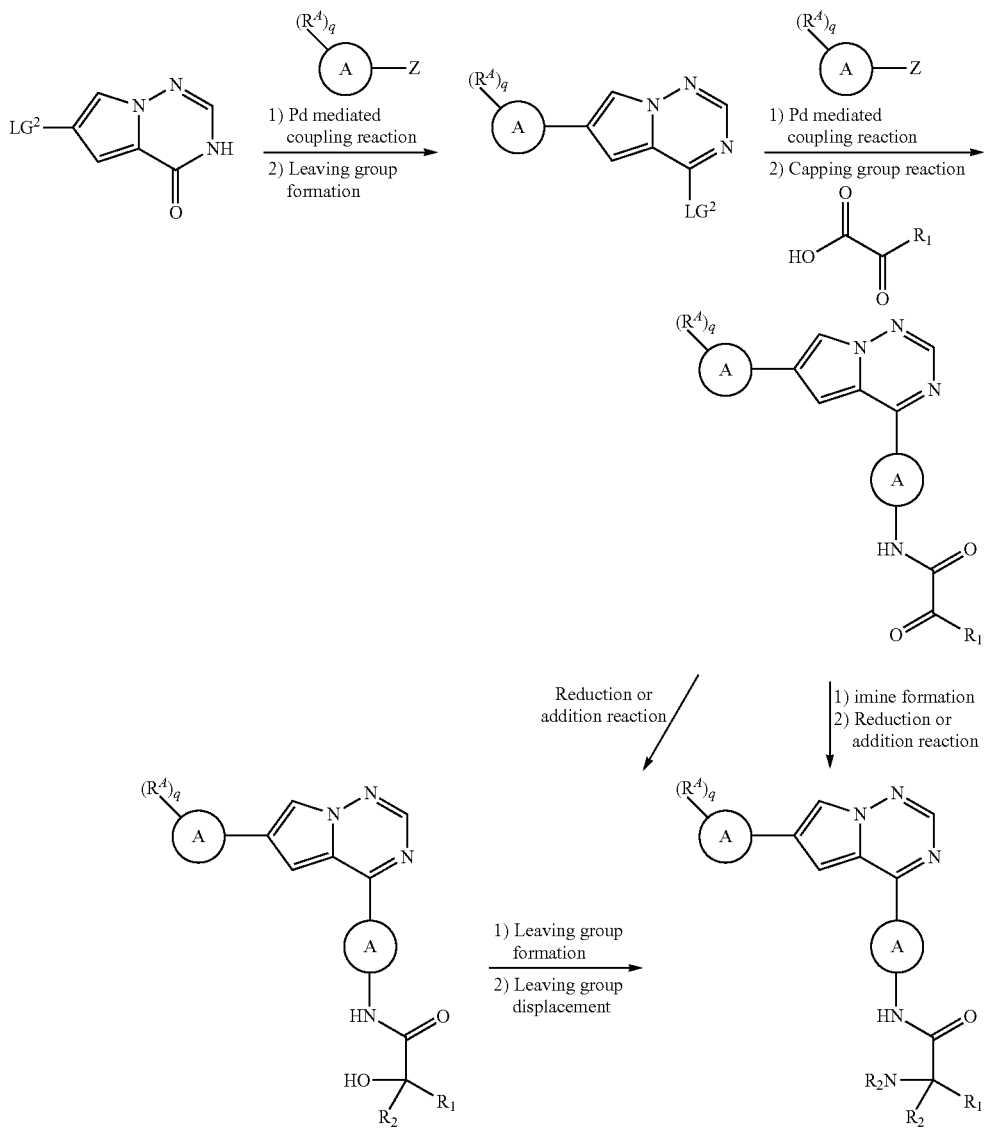

The pyrrolotriazinone can be coupled (LG² can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide an intermediate featuring a new carbon-carbon bond formed after subsequent installation of a leaving group (via POCl₃ or other similar reagents). The resulting pyrrolotriazine can be coupled through a similar process (LG² can be, e.g., Cl, Br, or I) to a boron, tin or zinc aryl, heteroaryl, alkenyl, or alkyl reagent via a palladium-mediated coupling reaction, e.g., Suzuki, Stille, or Negishi coupling, to provide an intermediate with a new carbon-carbon bond. This resulting di-substituted pyrrolotriazine can be further functionalized via an amide bond formation procedure. The resulting keto-amides can be elaborated to form alcohols (via reduction and addition reactions) and amines (via displacement of activated alcohols, reductions and additions to imines) to yield the products. As shown below, Compounds 31-34, 45-47, 49, 50, and 59 were prepared using Synthetic Protocol 4.

Example 5: Synthesis of 2-(4-chlorophenyl)-2-hydroxy-N-(4-(6-(1-methyl-1H-pyrazol-4-yl)pyrrolo[1,2-f][1,2,4]triazin-4-yl)phenyl)acetamide Compounds 32, 33, 34

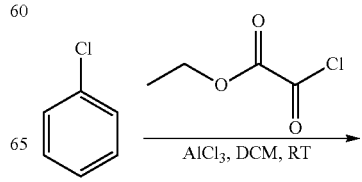

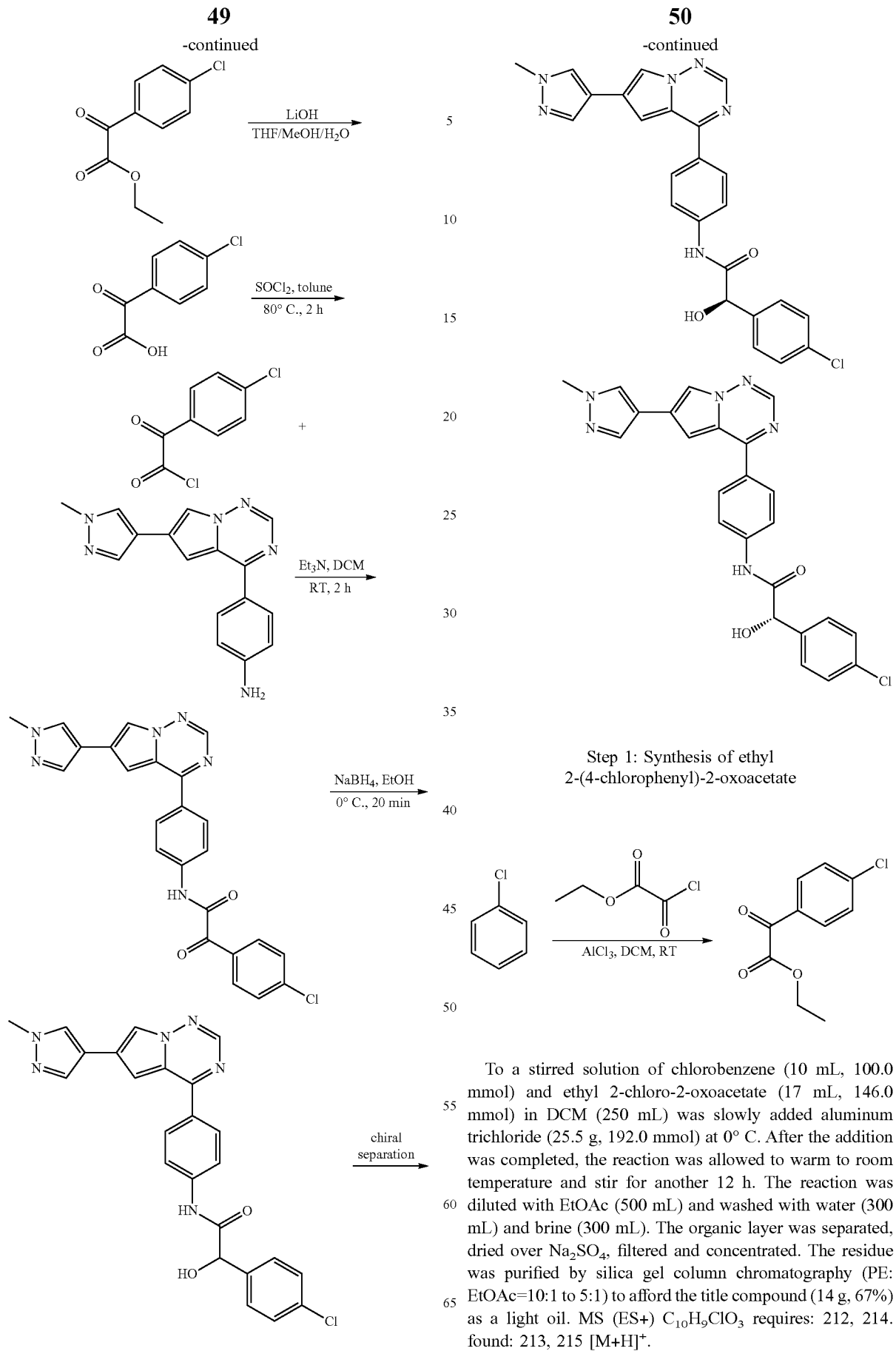

Step 1: Synthesis of ethyl 2-(4-chlorophenyl)-2-oxoacetate

To a stirred solution of chlorobenzene (10 mL, 100.0 mmol) and ethyl 2-chloro-2-oxoacetate (17 mL, 146.0 mmol) in DCM (250 mL) was slowly added aluminum trichloride (25.5 g, 192.0 mmol) at 0° C. After the addition was completed, the reaction was allowed to warm to room temperature and stir for another 12 h. The reaction was diluted with EtOAc (500 mL) and washed with water (300 mL) and brine (300 mL). The organic layer was separated, dried over $Na_2SO_4$, filtered and concentrated. The residue was purified by silica gel column chromatography (PE:EtOAc=10:1 to 5:1) to afford the title compound (14 g, 67%) as a light oil. MS (ES+) $C_{10}H_9ClO_3$ requires: 212, 214. found: 213, 215 $[M+H]^+$.

Step 2: Synthesis of 2-(4-chlorophenyl)-2-oxoacetic acid

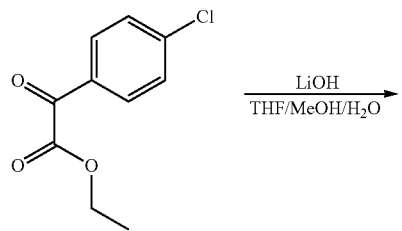

A mixture of ethyl 2-(4-chlorophenyl)-2-oxoacetate (4.0 g, 18.9 mmol) and lithium hydroxide (1.98 g, 47.1 mmol) in THF:MeOH:H₂O (76 mL, v/v/v=10:6:3) was stirred at 25° C. for 3 h. The mixture was neutralized with conc. HCl to pH=2-3. The formed white precipitate was collected via filtration, washed with water three times and dried under vacuum to afford the title compound (3.0 g, 86%) as a white solid. MS (ES+) $C_8H_5ClO_3$ requires: 184, 186. found: 185, 187 $[M+H]^+$.

Step 3: Synthesis of 2-(4-chlorophenyl)-2-oxoacetyl chloride

A mixture of 2-(4-chlorophenyl)-2-oxoacetic acid (1.0 g, 5.44 mmol) and thionyl chloride (1.4 g, 12.0 mmol) in toluene (10 mL) was heated at 80° C. for 3 h. After the reaction was complete, the mixture was concentrated under reduced pressure to give the title compound as a yellow oil (crude, 1.11 g, 100%), which was used directly into the next step without further purification.

Step 4: Synthesis of 2-(4-chlorophenyl)-N-(4-(6-(1-methyl-1H-pyrazol-4-yl)pyrrolo[1,2-f][1,2,4]triazin-4-yl)phenyl)-2-oxoacetamide

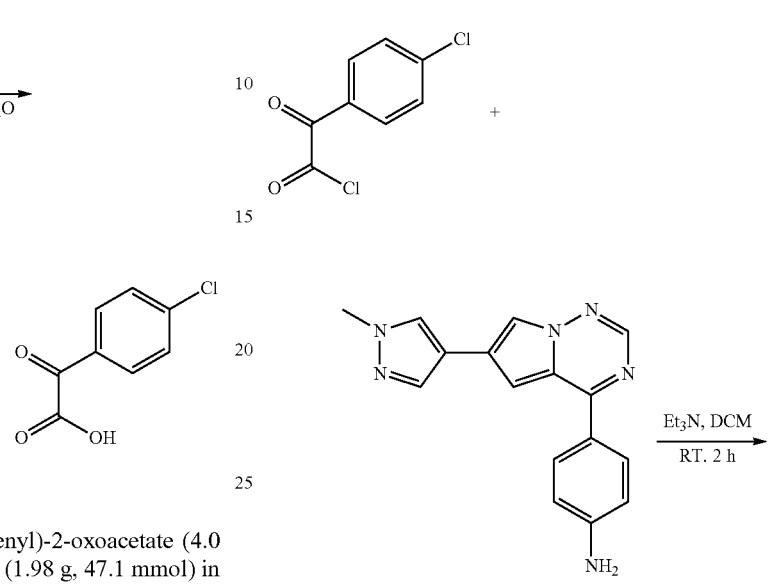

To a stirred solution of 2-(4-chlorophenyl)-2-oxoacetyl chloride (1.11 g, 5.44 mmol) and 4-(6-(1-methyl-1H-pyrazol-4-yl)pyrrolo[1,2-f][1,2,4]triazin-4-yl)benzenamine (1.58 mL, 5.44 mmol) in DCM (30 mL) was added triethylamine (1.65 g, 16.3 mmol). After stirring at 25° C. for 2 h, the reaction mixture was diluted with DCM (200 mL) and washed with water (200 mL) and brine (200 mL). The organic layer was dried over Na₂SO₄, filtered, and concentrated. The residue was purified by silica gel column chromatography (DCM:EtOAc=10:1) to afford the title compound (800 mg, 32%) as a yellow solid. MS (ES+) $C_{24}H_{17}ClN_6O_2$ requires: 456, 458. found: 457, 459 $[M+H]^+$.

Step 5: Synthesis of 2-(4-chlorophenyl)-2-hydroxy-N-(4-(6-(1-methyl-1H-pyrazol-4-yl)pyrrolo[1,2-f][1,2,4]triazin-4-yl)phenyl)acetamide

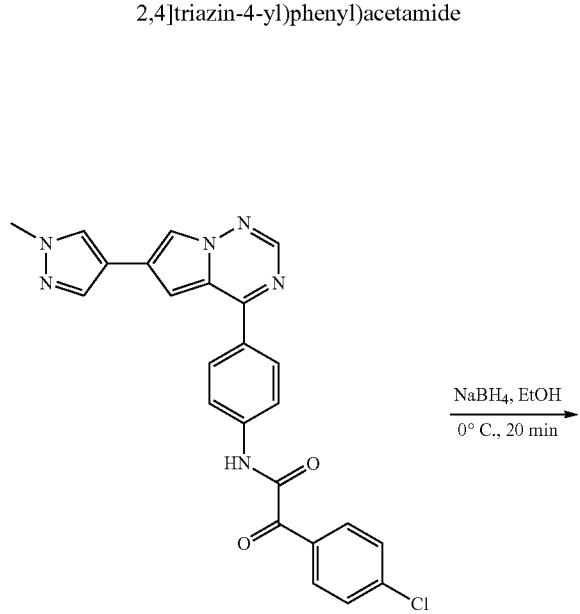

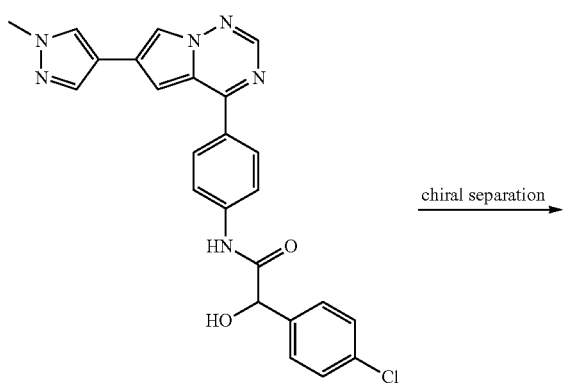

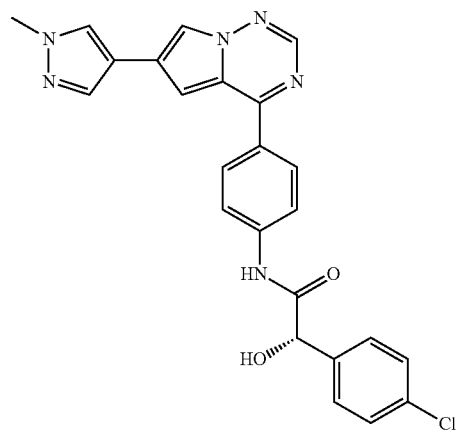

A mixture of 22-(4-chlorophenyl)-N-(4-(6-(1-methyl-1H-pyrazol-4-yl)pyrrolo[1,2-f][1,2,4]triazin-4-yl)phenyl)-2-oxoacetamide (140 mg, 0.31 mmol) and sodium borohydride (30 mg, 0.8 mmol) in ethanol (6 mL) was stirred at 25° C. for 1 h. After the reaction was complete, the mixture was concentrated and the residue purified by silica gel column chromatography (DCM:MeOH=20:1) to afford 2-(4-chlorophenyl)-2-hydroxy-N-(4-(6-(1-methyl-1H-pyrazol-4-yl)pyrrolo[1,2-f][1,2,4]triazin-4-yl)phenyl)acetamide (racemate, 150 mg, 75%) as a yellow solid. MS (ES+) $C_{24}H_{19}ClN_6O_2$ requires: 458, 460. found: 459, 461 [M+H]$^+$. The above racemic product was purified by chiral-HPLC to afford the single isomers (single enantiomer, first peak, 50 mg, 83%) as a yellow solid. MS (ES+) $C_{24}H_{19}ClN_6O_2$ requires: 458. found: 459, 461 [M+H]+.

Example 6: Synthesis of 2-(4-chlorophenyl)-2-(dimethylamino)-N-(4-(6-(1-methyl-1H-pyrazol-4-yl)pyrrolo[1,2-f][1,2,4]triazin-4-yl)phenyl)acetamide
Compound 59

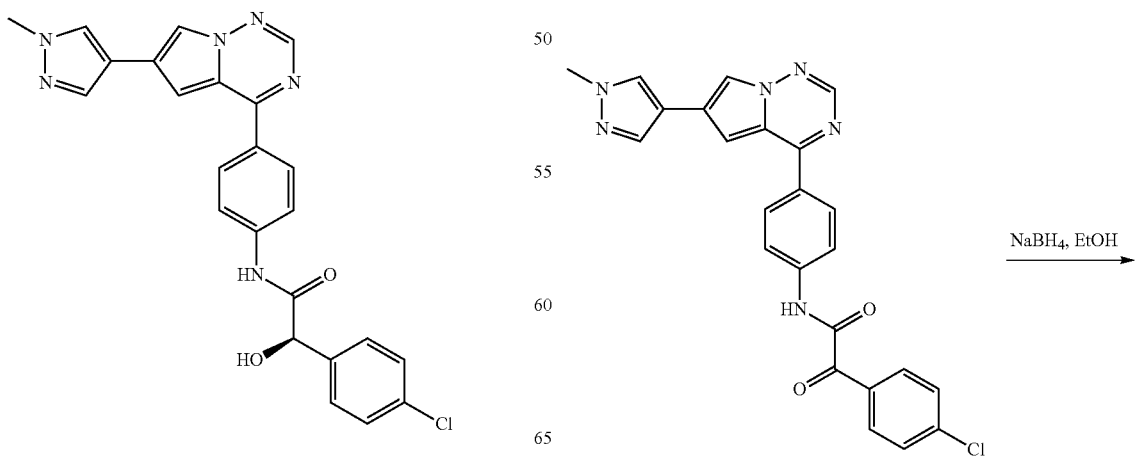

56

Step 1: Synthesis of 2-(4-chlorophenyl)-2-hydroxy-N-(4-(6-(1-methyl-1H-pyrazol-4-yl)pyrrolo[1,2-f][1,2,4]triazin-4-yl)phenyl)acetamide

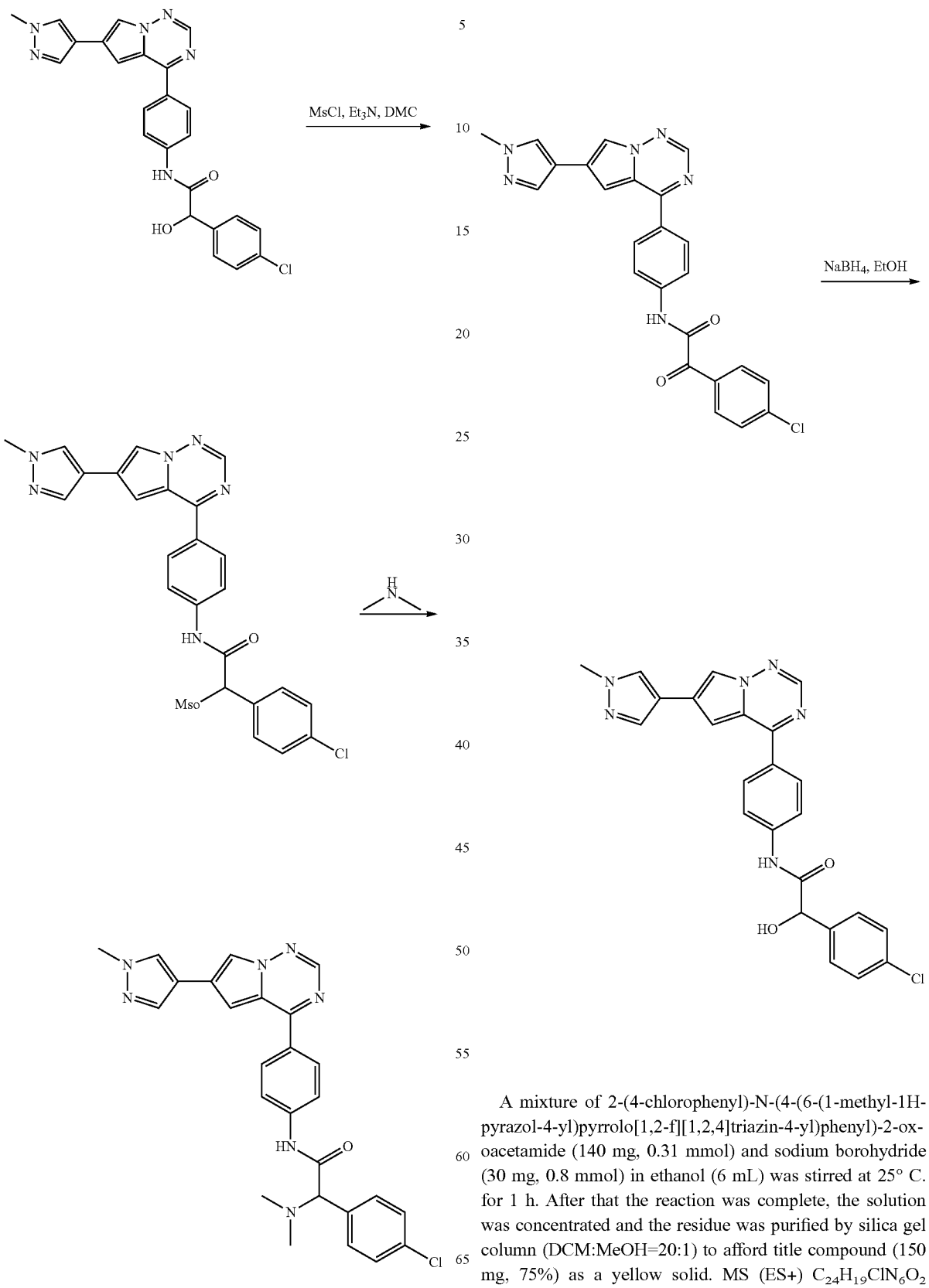

A mixture of 2-(4-chlorophenyl)-N-(4-(6-(1-methyl-1H-pyrazol-4-yl)pyrrolo[1,2-f][1,2,4]triazin-4-yl)phenyl)-2-oxoacetamide (140 mg, 0.31 mmol) and sodium borohydride (30 mg, 0.8 mmol) in ethanol (6 mL) was stirred at 25° C. for 1 h. After that the reaction was complete, the solution was concentrated and the residue was purified by silica gel column (DCM:MeOH=20:1) to afford title compound (150 mg, 75%) as a yellow solid. MS (ES+) $C_{24}H_{19}ClN_6O_2$ requires: 458, 460. found: 459, 461 $[M+H]^+$.

Step 2: Synthesis of 1-(4-chlorophenyl)-2-(4-(6-(1-methyl-1H-pyrazol-4-yl)pyrrolo[1,2-f][1,2,4]triazin-4-yl)phenylamino)-2-oxoethyl methanesulfonate

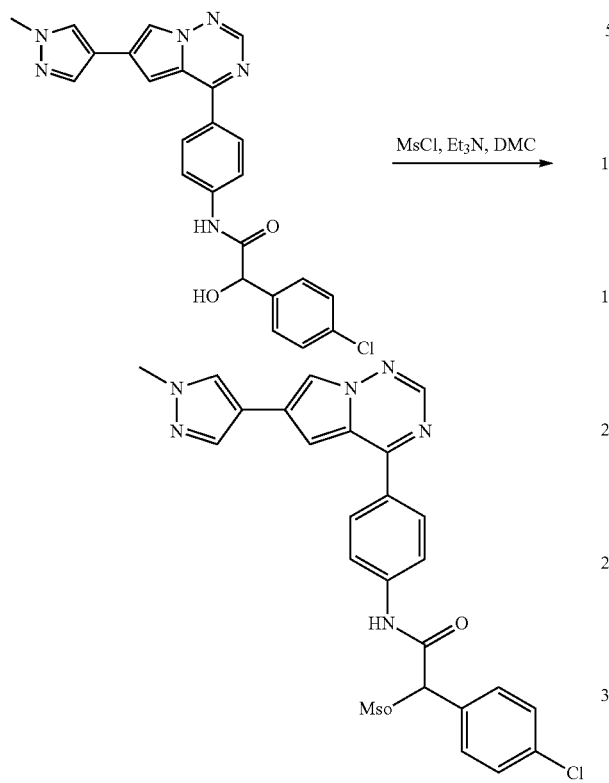

To a solution of 2-(4-chlorophenyl)-2-hydroxy-N-(4-(6-(1-methyl-1H-pyrazol-4-yl)pyrrolo[1,2-f][1,2,4]triazin-4-yl)phenyl)acetamide (80 mg, 0.17 mmol) and triethylamine (52 mg, 0.51 mmol) in DCM (30 mL) was added MsCl (40 mg, 0.34 mmol) at room temperature. The resultant mixture was stirred at room temperature for 1 h. After the reaction was complete, the mixture was washed with water and brine and the organic layer dried over $Na_2SO_4$ and concentrated to give the crude product (94 mg, crude) as a colorless oil, which was used for next step without further purification.

Step 3: Synthesis of 2-(4-chlorophenyl)-2-(dimethylamino)-N-(4-(6-(1-methyl-1H-pyrazol-4-yl)pyrrolo[1,2-f][1,2,4]triazin-4-yl)phenyl)acetamide

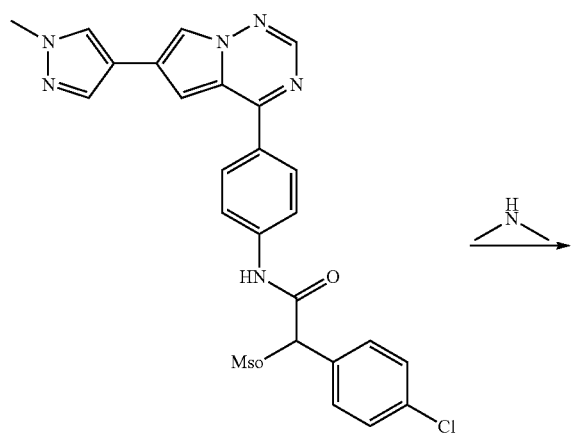

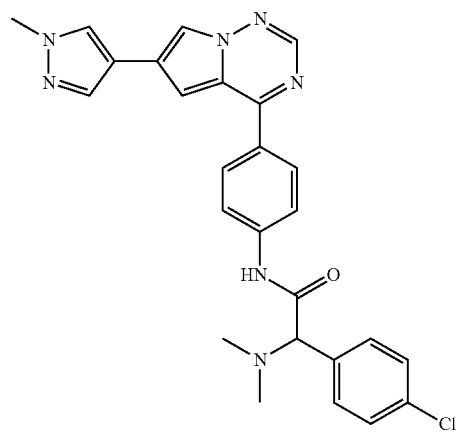

A solution of 1-(4-chlorophenyl)-2-(4-(6-(1-methyl-1H-pyrazol-4-yl)pyrrolo[1,2-f][1,2,4]triazin-4-yl)phenylamino)-2-oxoethyl methanesulfonate (94 mg, 0.17 mmol), dimethylamine (2 N in THF, 0.27 mL, 0.54 mmol) and triethylamine (85 mg, 0.85 mmol) in acetone (10 mL) was stirred at 60° C. for 12 h. Once LCMS showed the reaction was complete, the solvents were removed under reduced pressure and the residue was purified by preparative HPLC to afford 2-(4-chlorophenyl)-2-(dimethylamino)-N-(4-(6-(1-methyl-1H-pyrazol-4-yl)pyrrolo[1,2-f][1,2,4]triazin-4-yl)phenyl)acetamide (49 mg, 59%) as a yellow solid, MS (ES+) C26H24ClN7O requires: 485, 487. found 486, 488 $[M+H]^+$.

Example 7: Synthesis of 2-(4-chlorophenyl)-2-hydroxy-N-(4-(6-(1-methyl-1H-pyrazol-4-yl)pyrrolo[1,2-f][1,2,4]triazin-4-yl)phenyl)propanamide (Compound 49 and Compound 50)

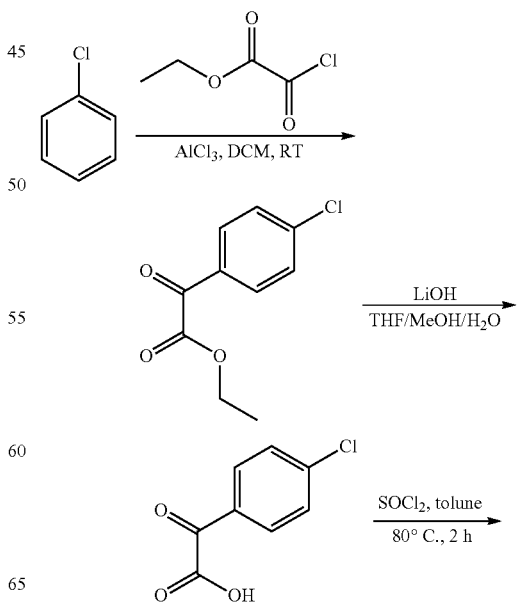

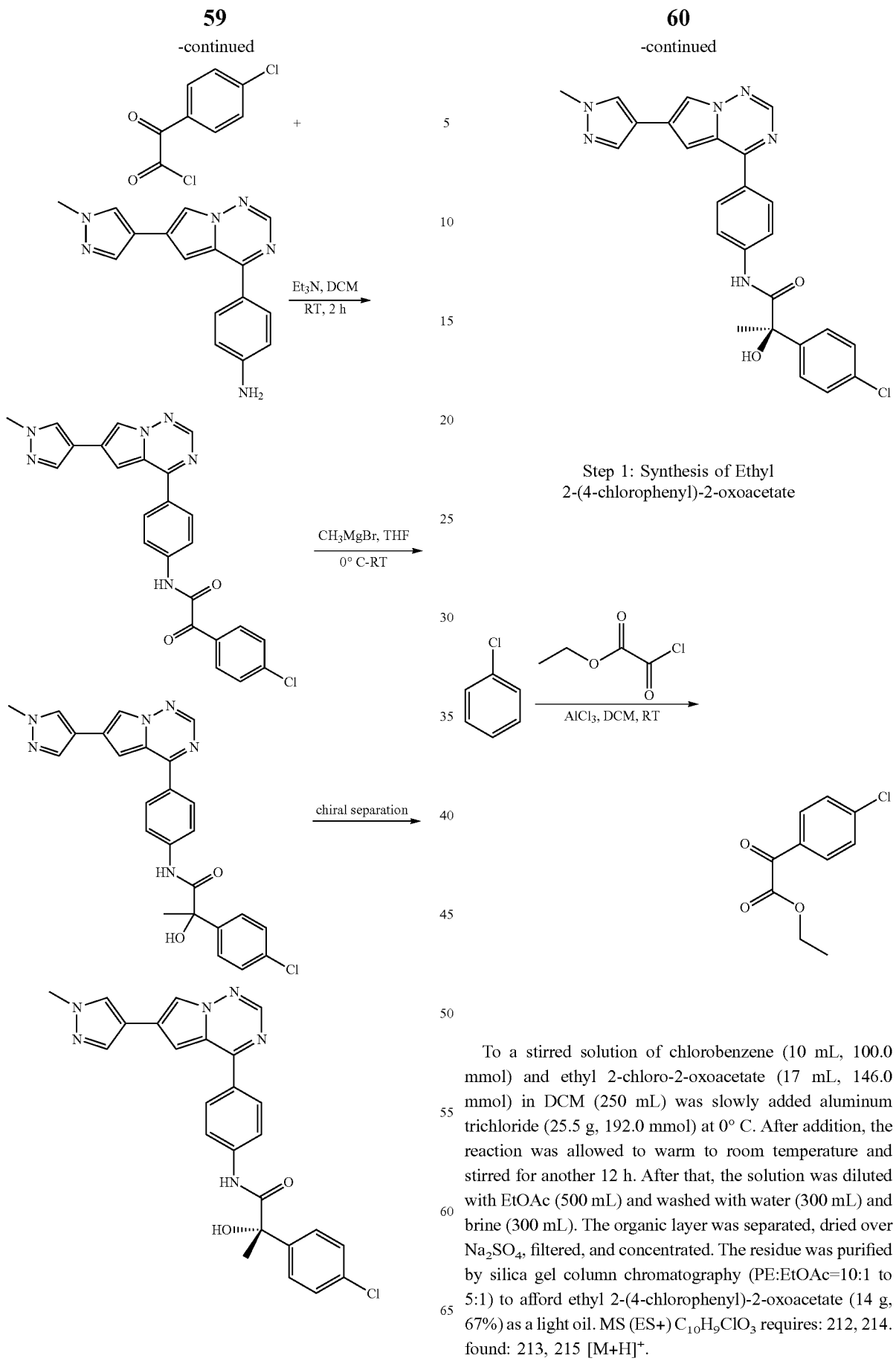

Step 1: Synthesis of Ethyl 2-(4-chlorophenyl)-2-oxoacetate

To a stirred solution of chlorobenzene (10 mL, 100.0 mmol) and ethyl 2-chloro-2-oxoacetate (17 mL, 146.0 mmol) in DCM (250 mL) was slowly added aluminum trichloride (25.5 g, 192.0 mmol) at 0° C. After addition, the reaction was allowed to warm to room temperature and stirred for another 12 h. After that, the solution was diluted with EtOAc (500 mL) and washed with water (300 mL) and brine (300 mL). The organic layer was separated, dried over $Na_2SO_4$, filtered, and concentrated. The residue was purified by silica gel column chromatography (PE:EtOAc=10:1 to 5:1) to afford ethyl 2-(4-chlorophenyl)-2-oxoacetate (14 g, 67%) as a light oil. MS (ES+) $C_{10}H_9ClO_3$ requires: 212, 214. found: 213, 215 $[M+H]^+$.

Step 2: Synthesis of 2-(4-chlorophenyl)-2-oxoacetic acid

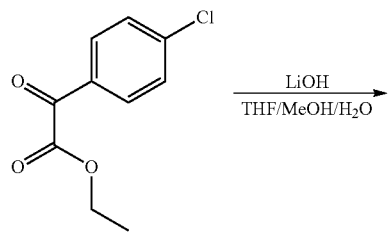

A mixture of ethyl 2-(4-chlorophenyl)-2-oxoacetate (4.0 g, 18.9 mmol) and lithium hydroxide (1.98 g, 47.1 mmol) in THF:MeOH:H₂O (76 mL, v/v/v=10:6:3) was stirred at 25° C. for 3 h. The mixture was neutralized with conc. HCl to pH=2-3, and the white precipitate was collected via filtration, washed with water three times and dried under vacuum to afford 2-(4-chlorophenyl)-2-oxoacetic acid (3.0 g, 86%) as a white solid. MS (ES+) $C_8H_5ClO_3$ requires: 184, 186. found: 185, 187 [M+H]⁺.

Step 3: Synthesis of 2-(4-chlorophenyl)-2-oxoacetyl chloride

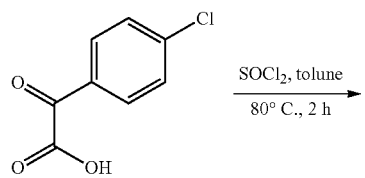

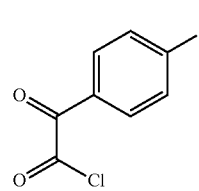

A mixture of 2-(4-chlorophenyl)-2-oxoacetic acid (1.0 g, 5.44 mmol) and thionyl chloride (1.4 g, 12.0 mmol) in toluene (10 mL) was heated at 80° C. for 3 h. After that the reaction was complete, the solution was concentrated under reduced pressure to give 2-(4-chlorophenyl)-2-oxoacetyl chloride as a yellow oil (1.11 g, crude), which was used directly into next step without further purification.

Step 4: Synthesis of 2-(4-chlorophenyl)-N-(4-(6-(1-methyl-1H-pyrazol-4-yl)pyrrolo[1,2-f][1,2,4]triazin-4-yl)phenyl)-2-oxoacetamide

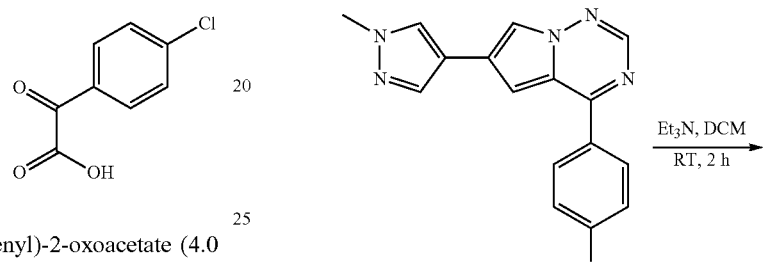

To a stirred solution of 2-(4-chlorophenyl)-2-oxoacetyl chloride (1.11 g, 5.44 mmol) and 4-(6-(1-methyl-1H-pyrazol-4-yl)pyrrolo[1,2-f][1,2,4]triazin-4-yl)benzenamine (1.58 mL, 5.44 mmol) in DCM (30 mL) was added triethylamine (1.65 g, 16.3 mmol) at room temperature. The solution was stirred at 25° C. for 2 h, followed by dilution of the mixture with DCM (200 mL) and washing with water (200 mL) and brine (200 mL). The organic layer was then dried over Na₂SO₄, filtered, and concentrated. The residue was purified by silica gel column chromatography (DCM:EtOAc=10:1) to afford 2-(4-chlorophenyl)-N-(4-(6-(1-methyl-1H-pyrazol-4-yl)pyrrolo[1,2-f][1,2,4]triazin-4-yl)phenyl)-2-oxoacetamide (800 mg, 32%) as a yellow solid. MS (ES+) $C_{24}H_{17}ClN_6O_2$ requires: 456, 458. found: 457, 459 [M+H]⁺.

Step 5: Synthesis of 2-(4-chlorophenyl)-2-hydroxy-N-(4-(6-(1-methyl-1H-pyrazol-4-yl)pyrrolo[1,2-f][1,2,4]triazin-4-yl)phenyl)propanamide

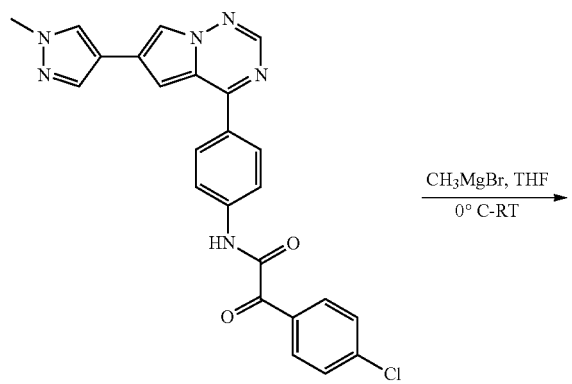

CH₃MgBr, THF
0° C-RT
→

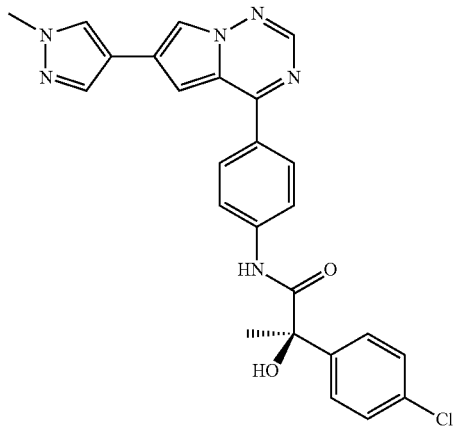

chiral separation
→

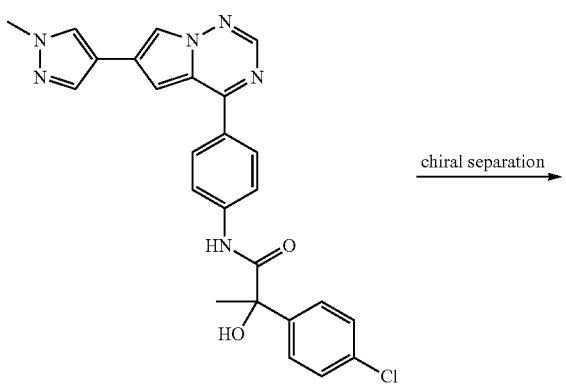

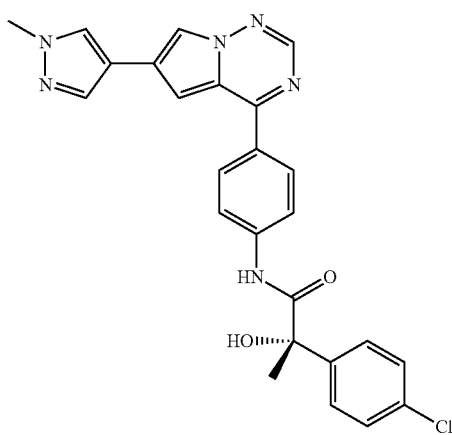

To a solution of 2-(4-chlorophenyl)-N-(4-(6-(1-methyl-1H-pyrazol-4-yl)pyrrolo[1,2-f][1,2,4]triazin-4-yl)phenyl)-2-oxoacetamide (200 mg, 0.44 mmol) in THF (20 mL) was dropwise added MeMgBr (3 M in ethyl ether, 0.19 mL, 0.57 mmol) at 0° C. The reaction mixture was warmed to room temperature and stirred for 1 h. After that, the reaction was quenched with saturated aqueous ammonium chloride and extracted with EtOAc. The combined organic layers were dried over Na₂SO₄, filtered, and concentrated in vacuo. The residue was purified by silica gel column (DCM:MeOH=20:1) to give 2-(4-chlorophenyl)-2-hydroxy-N-(4-(6-(1-methyl-1H-pyrazol-4-yl)pyrrolo[1,2-f][1,2,4]triazin-4-yl)phenyl)propanamide (120 mg, yield 56%) as a yellow solid. MS (ES+) C₂₅H₂₁ClN₆O₂ requires: 472. found 473 [M+H]⁺. The above racemic product 2-(4-chlorophenyl)-2-hydroxy-N-(4-(6-(1-methyl-1H-pyrazol-4-yl)pyrrolo[1,2-f][1,2,4]triazin-4-yl)phenyl)propanamide was purified by chiral HPLC to afford the isomers (single enantiomer, first peak, 50 mg, 43%) as a yellow solid. MS (ES+) C₂₅H₂₁ClN₆O₂ requires: 472. found 473 [M+H]⁺.

Example 8: Synthesis of 2-amino-2-(4-chlorophenyl)-N-(4-(6-(1-methyl-1H-pyrazol-4-yl)pyrrolo[1,2-f][1,2,4]triazin-4-yl)phenyl)acetamide
(Compound 31)

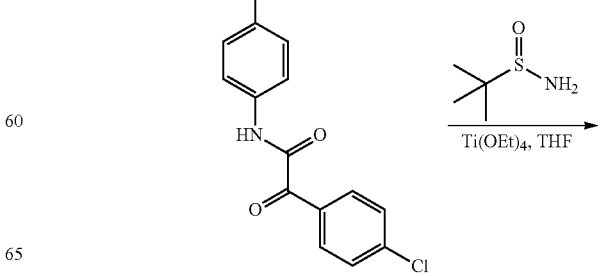

Ti(OEt)₄, THF
→

65
-continued

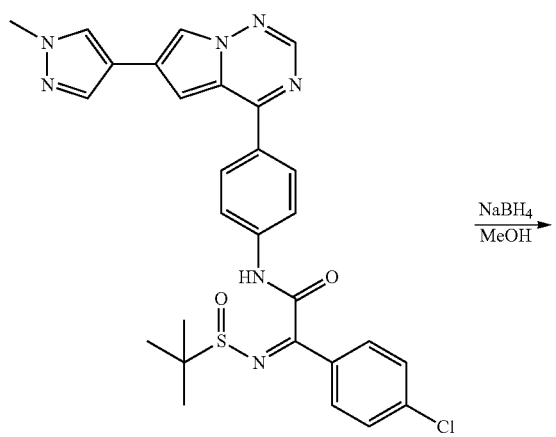

66

Step 1: Synthesis of 2-(tert-butylsulfinylimino)-2-(4-chlorophenyl)-N-(4-(6-(1-methyl-1H-pyrazol-4-yl)pyrrolo[1,2-f][1,2,4]triazin-4-yl)phenyl)acetamide

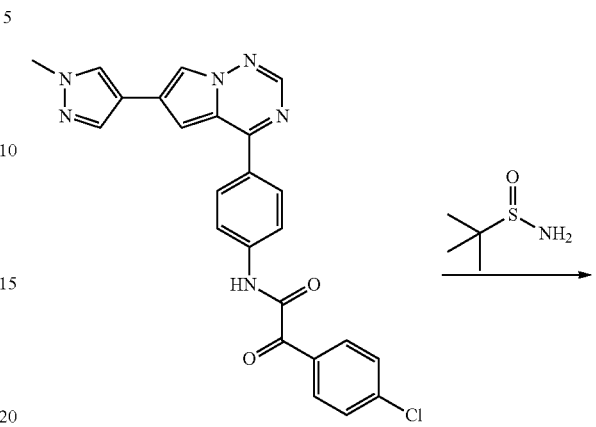

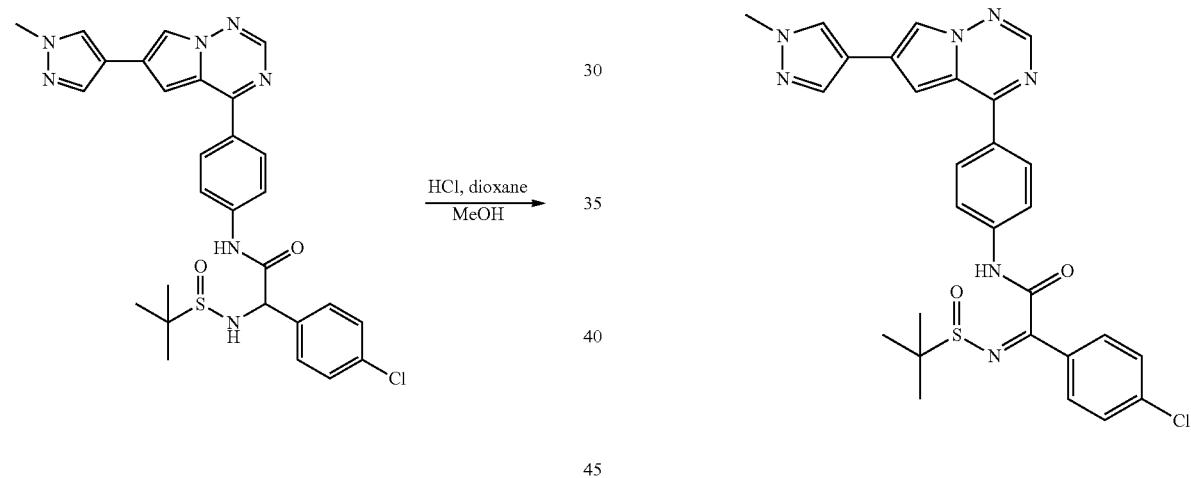

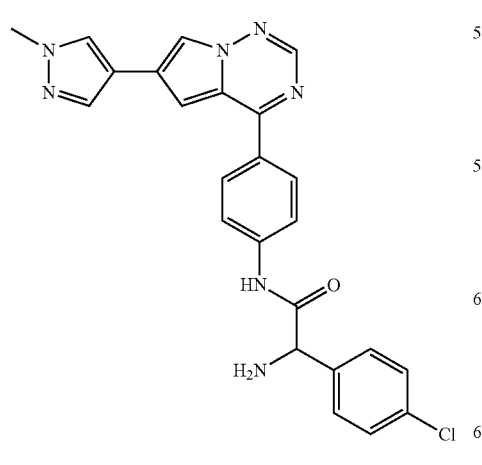

A mixture of 2-(4-chlorophenyl)-N-(4-(6-(1-methyl-1H-pyrazol-4-yl)pyrrolo[1,2-f][1,2,4]triazin-4-yl)phenyl)-2-oxoacetamide (300 mg, 0.6 mmol), 2-methylpropane-2-sulfinamide (88 mg, 0.72 mmol), tetraisopropyl titanate(IV) (860 mg, 3.0 mmol) in THF (20 mL) was stirred at 80° C. for 20 h under $N_2$. The mixture was then concentrated and the residue was diluted with MeOH/DCM (200 mL, v/v=1:3), then filtered through celite. The filtrate was purified by silica gel column chromatography (DCM:MeOH=10:1) to afford the title compound 2-(tert-butylsulfinylimino)-2-(4-chlorophenyl)-N-(4-(6-(1-methyl-1H-pyrazol-4-yl)pyrrolo[1,2-f][1,2,4]triazin-4-yl)phenyl)acetamide (280 mg, 83%) as a yellow solid. MS (ES+) $C_{28}H_{26}ClN_7O_2S$ requires: 559. found: 560, 562$[M+H]^+$.

Step 2: Synthesis of 2-(4-chlorophenyl)-2-imino-N-(4-(6-(1-methyl-1H-pyrazol-4-yl)pyrrolo[1,2-f][1,2,4]triazin-4-yl)phenyl)acetamide

Step 3: Synthesis of 2-amino-2-(4-chlorophenyl)-N-(4-(6-(1-methyl-1H-pyrazol-4-yl)pyrrolo[1,2-f][1,2,4]triazin-4-yl)phenyl)acetamide

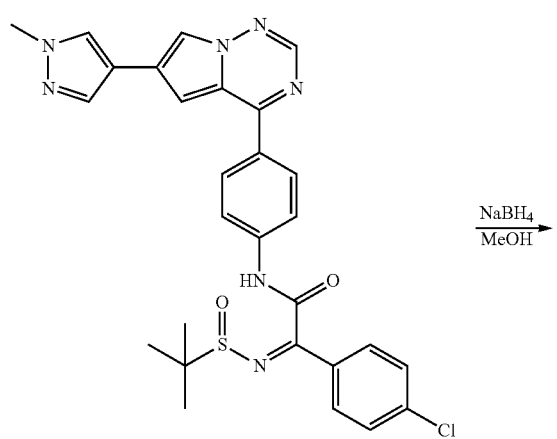

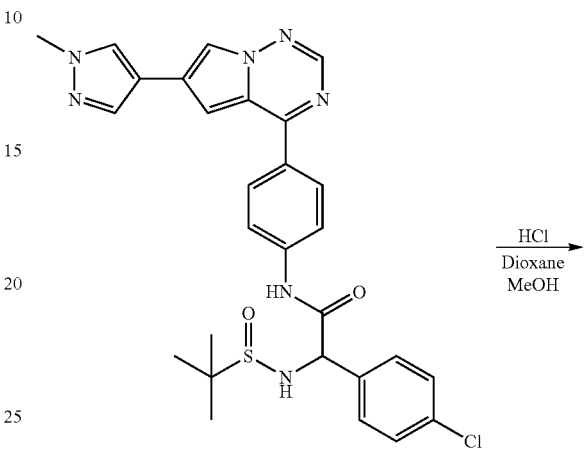

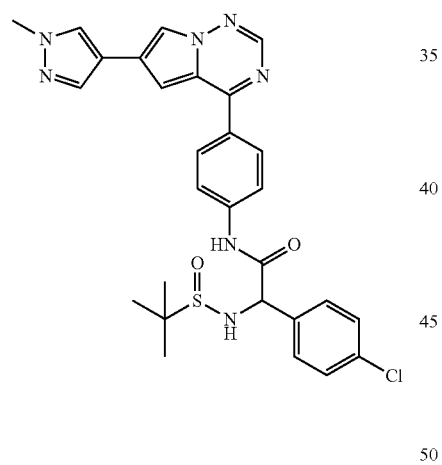

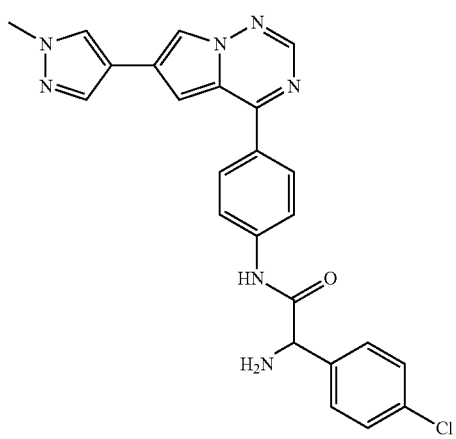

To a solution of 2-(tert-butylsulfinylimino)-2-(4-chlorophenyl)-N-(4-(6-(1-methyl-1H-pyrazol-4-yl)pyrrolo[1,2-f][1,2,4]triazin-4-yl)phenyl)acetamide (280 mg, 0.5 mmol) in 15 mL MeOH was added sodium borohydride (60 mg, 1.6 mmol) at 0° C., and the solution was allowed to stirred at room temperature for 3 h. The reaction solution was quenched by sat. NH$_4$Cl. aq (20 mL), extracted with EtOAc (20 mL×3), and the combined organic phase was concentrated under vacuo to afford the title product 2-(4-chlorophenyl)-2-imino-N-(4-(6-(1-methyl-1H-pyrazol-4-yl)pyrrolo[1,2-f][1,2,4]triazin-4-yl)phenyl)acetamide (290 mg, crude) as a yellow foam which was used in the next step directly without further purification. MS (ES+) C$_{28}$H$_{28}$ClN$_7$O$_2$S requires: 561. found: 562, 564 [M+H]$^+$.

To a solution of 2-(4-chlorophenyl)-2-imino-N-(4-(6-(1-methyl-1H-pyrazol-4-yl)pyrrolo[1,2-f][1,2,4]triazin-4-yl)phenyl)acetamide (290 mg, 0.5 mmol) in MeOH (6 mL) was added HCl/dioxane (4M, 1 mL) dropwise. The reaction was stirred at 25° C. for 12 h. The solution was then concentrated under vacuo and the residue purified by preparative HPLC to obtain 2-amino-2-(4-chlorophenyl)-N-(4-(6-(1-methyl-1H-pyrazol-4-yl)pyrrolo[1,2-f][1,2,4]triazin-4-yl)phenyl)acetamide (6.6 mg, 3%) as a white solid. MS (ES+) C$_{24}$H$_{20}$ClN$_7$O requires: 457. found: 458 [M+H]$^+$.

69
Example 9: Synthesis of (S)-2-amino-2-(4-chlorophenyl)-N-(4-(6-(1-methyl-1H-pyrazol-4-yl)pyrrolo[1,2-f][1,2,4]triazin-4-yl)phenyl)propanamide (Compounds 45-47)
70
-continued
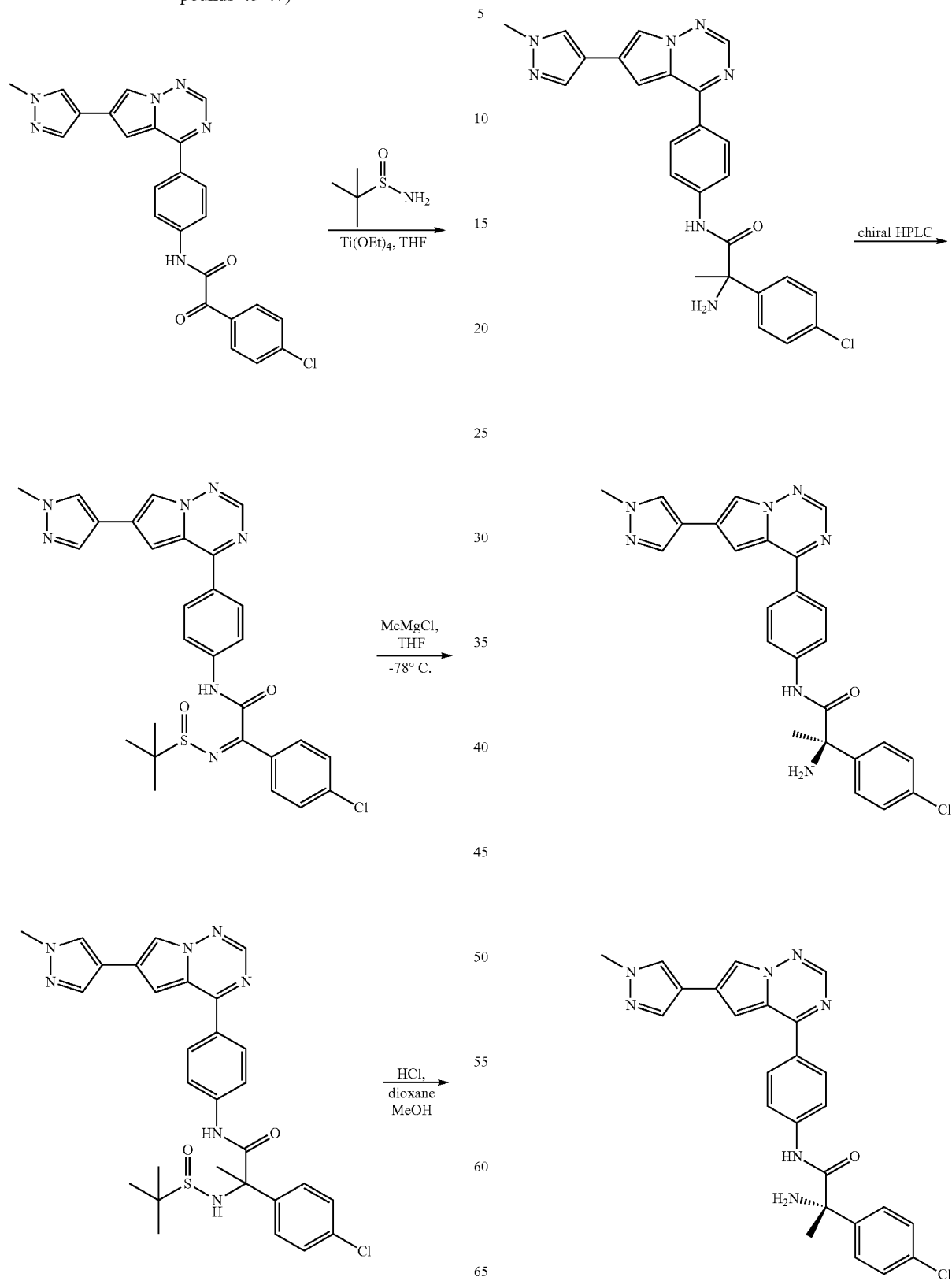

Step 1: Synthesis of 2-(tert-butylsulfinylimino)-2-(4-chlorophenyl)-N-(4-(6-(1-methyl-1H-pyrazol-4-yl)pyrrolo[1,2-f][1,2,4]triazin-4-yl)phenyl)acetamide Step 2: Synthesis of 2-(4-chlorophenyl)-2-(1,1-dimethylethylsulfinamido)-N-(4-(6-(1 methyl-1H-pyrazol-4-yl)pyrrolo[1,2-f][1,2,4]triazin-4-yl)phenyl)propanamide

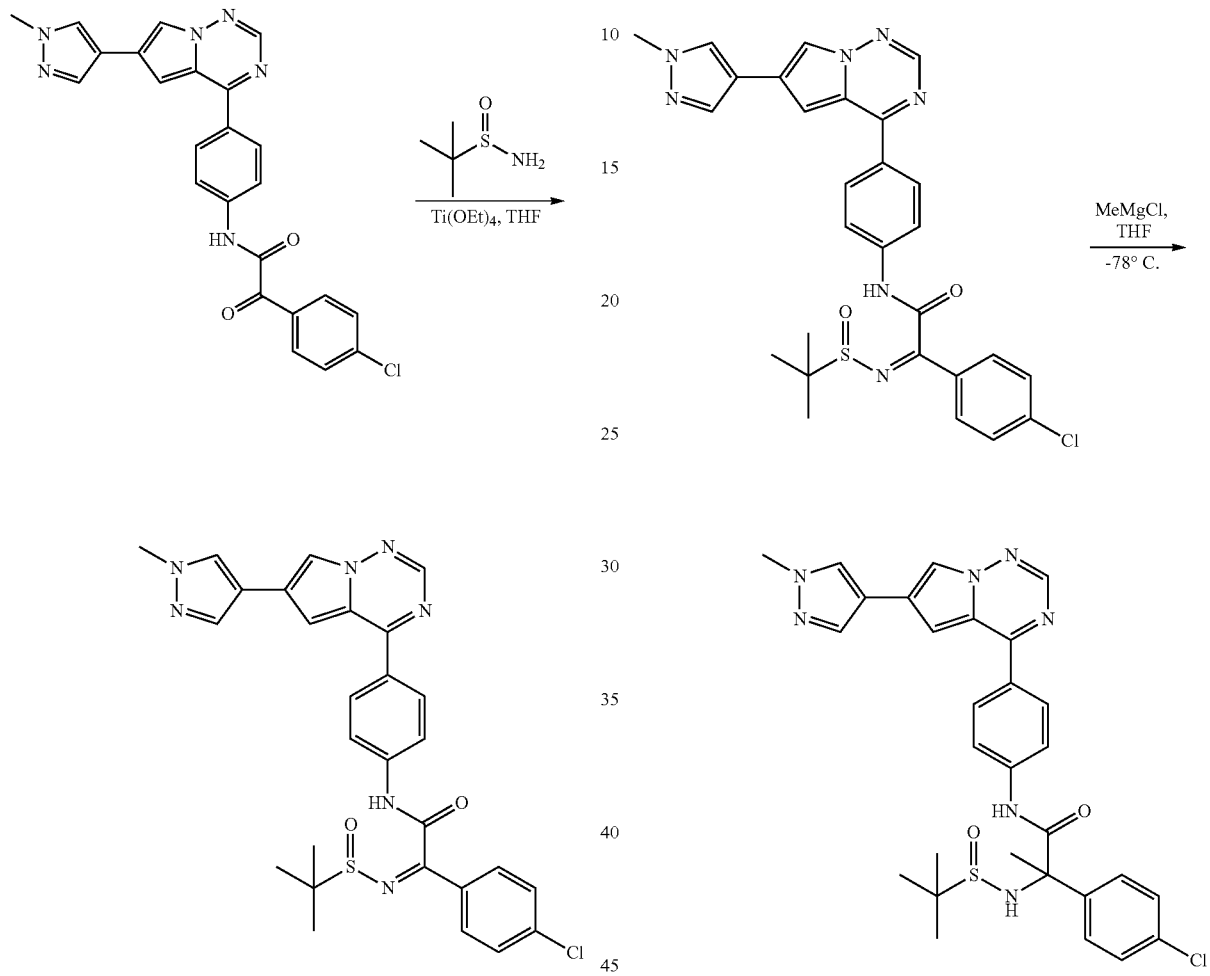

A mixture of 2-(4-chlorophenyl)-N-(4-(6-(1-methyl-1H-pyrazol-4-yl)pyrrolo[1,2-f][1,2,4]triazin-4-yl)phenyl)-2-oxoacetamide (350 mg, 0.78 mmol), 2-methylpropane-2-sulfinamide (120 mg, 1.0 mmol), and tetraethyl titanate (IV) (910 mg, 4.0 mmol) in THF (30 mL) was stirred at 80° C. for 2 days under $N_2$ The mixture was then concentrated, and the residue diluted with MeOH:DCM (200 mL, v/v=1:3) and filtered through celite. The filtrate was purified by silica gel column chromatography (DCM:MeOH=10:1) to afford the desired product 2-(tert-butylsulfinylimino)-2-(4-chlorophenyl)-N-(4-(6-(1-methyl-1H-pyrazol-4-yl)pyrrolo[1,2-f][1,2,4]triazin-4-yl)phenyl)acetamide (349 mg, 80%) as a yellow solid. MS (ES+) $C_{28}H_{26}ClN_7O_2S$ requires: 559. found: 560, 562[M+H]$^+$.

To a solution of 2-(tert-butylsulfinylimino)-2-(4-chlorophenyl)-N-(4-(6-(1-methyl-1H-pyrazol-4-yl)pyrrolo[1,2-f][1,2,4]triazin-4-yl)phenyl)acetamide (349 mg, 0.62 mmol) in THF (25 mL) at −78° C. under $N_2$ was added MeMgBr (3M in $Et_2O$, 1 mL) dropwise. The reaction mixture was stirred at −78° C. for 20 min, then warmed to 20° C. and allowed to stir for 12 h under $N_2$. After that, the reaction mixture was quenched by aqueous $NH_4Cl$ (50 mL), extracted with EtOAc (30 mL*3), and the combined organic layers were concentrated in vacuo. The residue was purified by silica gel column chromatography (DCM:MeOH=40:1) to afford the desired product 2-(4-chlorophenyl)-2-(1,1-dimethylethylsulfinamido)-N-(4-(6-(1-methyl-1H-pyrazol-4-yl)pyrrolo[1,2-f][1,2,4]triazin-4-yl)phenyl)propanamide (100 mg, 22%) as a yellow foam. MS (ES+) $C_{29}H_{30}ClN_7O_2S$ requires: 575. found 576, 578 [M+H]$^+$;

Step 3: Synthesis of 2-amino-2-(4-chlorophenyl)-N-(4-(6-(1-methyl-1H-pyrazol-4-yl)pyrrolo[1,2-f][1,2,4]triazin-4-yl)phenyl)propanamide

Step 4: Synthesis of (S)-2-amino-2-(4-chlorophenyl)-N-(4-(6-(1-methyl-1H-pyrazol-4-yl)pyrrolo[1,2-f][1,2,4]triazin-4-yl)phenyl)propanamide

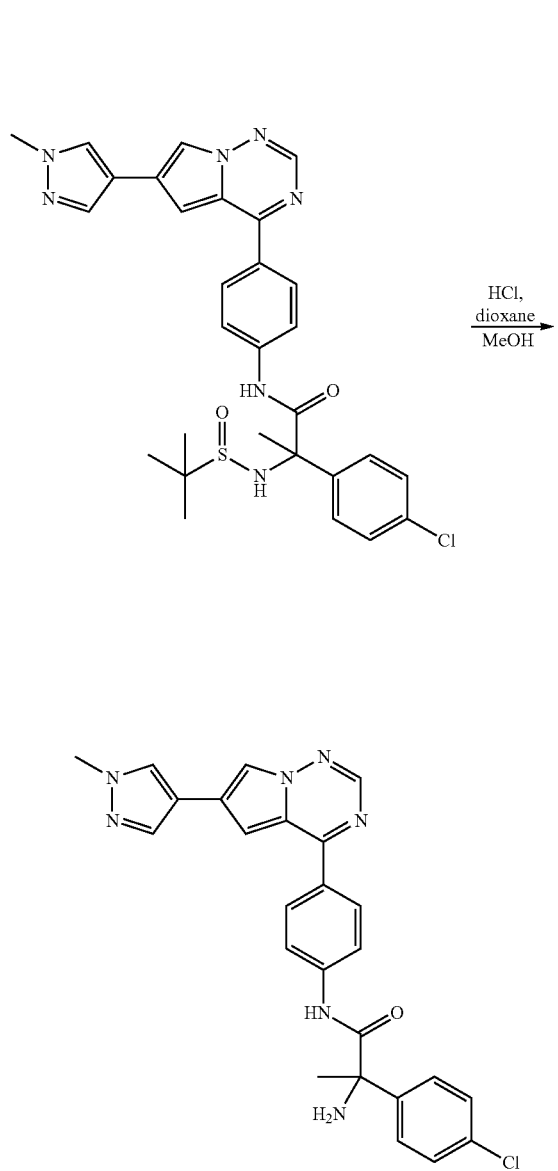

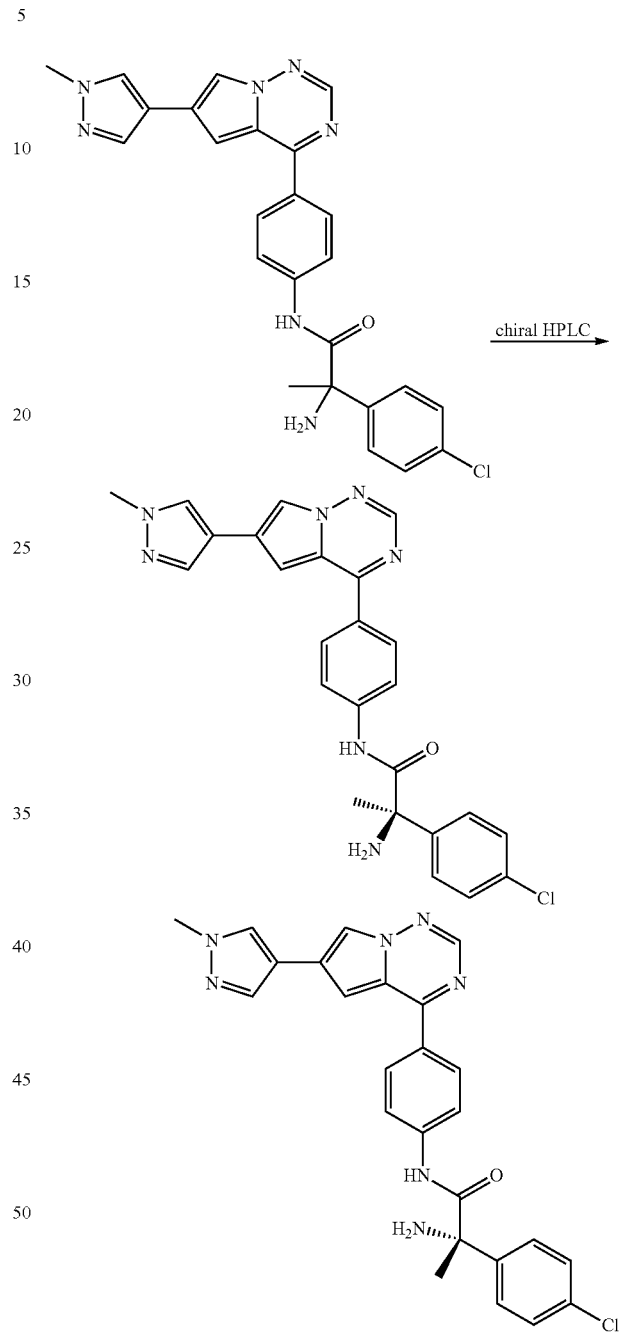

To a solution of 2-(4-chlorophenyl)-2-(1,1-dimethylethylsulfinamido)-N-(4-(6-(1-methyl-1H-pyrazol-4-yl)pyrrolo[1,2-f][1,2,4]triazin-4-yl)phenyl)propanamide (100 mg, 0.17 mmol) in MeOH (6 mL) was added HCl dioxane (4M, 1 mL) dropwise. The reaction solution was stirred at 25° C. for 12 h, then the solution was concentrated under vacuo and the residue was purified with preparative HPLC to obtain the desired 2-amino-2-(4-chlorophenyl)-N-(4-(6-(1-methyl-1H-pyrazol-4-yl)pyrrolo[1,2-f][1,2,4]triazin-4-yl)phenyl)propanamide (60 mg, 75%) as a white solid. MS (ES+) $C_{25}H_{22}ClN_7O$ requires: 471. found 472, 474 [M+H]$^+$ A mixture of racemic 2-amino-2-(4-chlorophenyl)-N-(4-(6-(1-methyl-1H-pyrazol-4-yl)pyrrolo[1,2-f][1,2,4]triazin-4-yl)phenyl)propanamide (60 mg) was separated by chiral-HPLC to afford (R)-2-amino-2-(4-chlorophenyl)-N-(4-(6-(1-methyl-1H-pyrazol-4-yl)pyrrolo[1,2-f][1,2,4]triazin-4-yl)phenyl)propanamide (16 mg, >99% ee) and (S)-2-amino-2-(4-chlorophenyl)-N-(4-(6-(1-methyl-1H-pyrazol-4-yl)pyrrolo[1,2-f][1,2,4]triazin-4-yl)phenyl)propanamide (18 mg, 98.3% ee).

Preparation of Common Intermediates

Example 10: Synthesis of 4-(6-(1-methyl-1H-pyrazol-4-yl)pyrrolo[2,1-f][1,2,4]triazin-4-yl)aniline hydrochloride

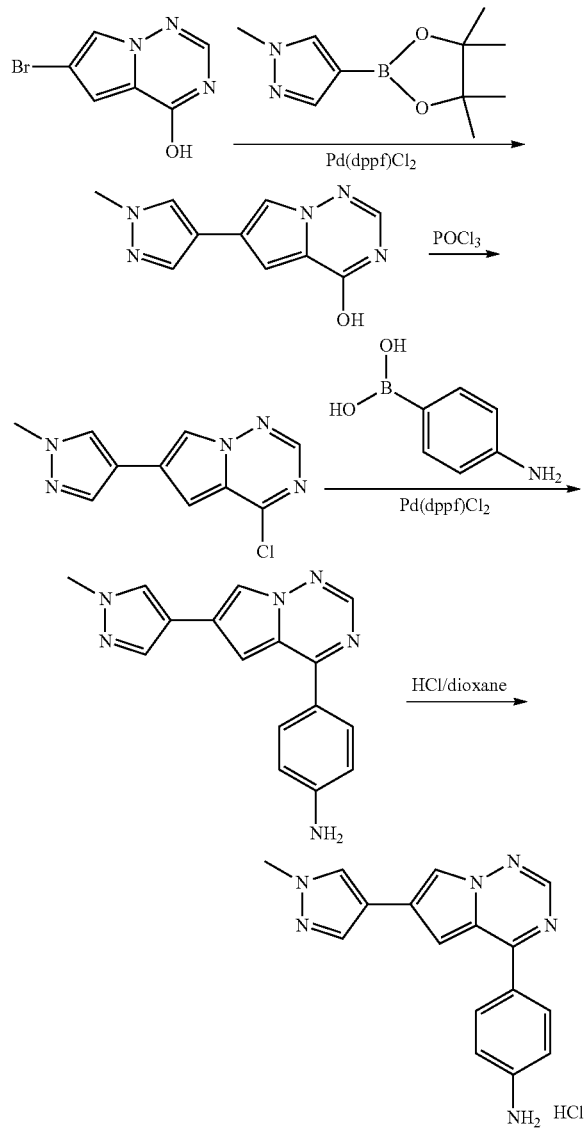

Step 1: Synthesis of 6-(1-methyl-1H-pyrazol-4-yl)pyrrolo[2,1-f][1,2,4]triazin-4-ol

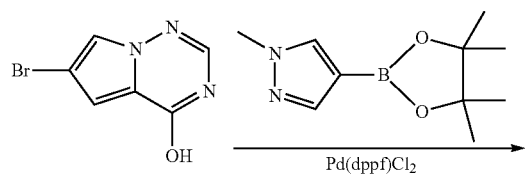

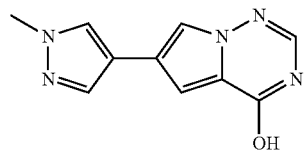

The suspension of 6-bromopyrrolo[2,1-f][1,2,4]triazin-4-ol (50.00 g, 233.62 mmol, 1.00 equiv), 1-methyl-4-(4,4,5,5-tetramethyl-1,3,2-dioxaborolan-2-yl)-1H-pyrazole (145.00 g, 696.91 mmol, 2.98 equiv) and Pd(PPh$_3$)$_4$ [Chemists, which one is it? (dppf)Cl$_2$ or PPh$_3$?] (3.00 g, 2.60 mmol, 0.01 equiv) in saturated aqueous K$_2$CO$_3$ (1000 mL) and DMF (1.00 L) was heated at 100° C. for 12 hr under N$_2$. After TLC indicated that the reaction was complete, the mixture was cooled and filtered, and the filtrate was acidified with 6 N HCl until the pH=8. The solid was filtered, and the filter cake was collected, washed with water, and dried to give 6-(1-methyl-1H-pyrazol-4-yl)pyrrolo[2,1-f][1,2,4]triazin-4-ol (35.0 g, 162.6 mmol, 69.6% yield) as a white solid. $^1$H-NMR (400 MHz, DMSO-d$_6$) δ ppm: 11.66 (s, 1H), 7.99 (s, 1H), 7.82 (s, 1H), 7.80 (s, 1H), 7.76 (s, 1H), 7.059-7.063 (d, J=8.8 Hz, 1H), 3.83 (s, 1H).

Step 2: Synthesis of 4-chloro-6-(1-methyl-1H-pyrazol-4-yl)pyrrolo[2,1-f][1,2,4]triazine

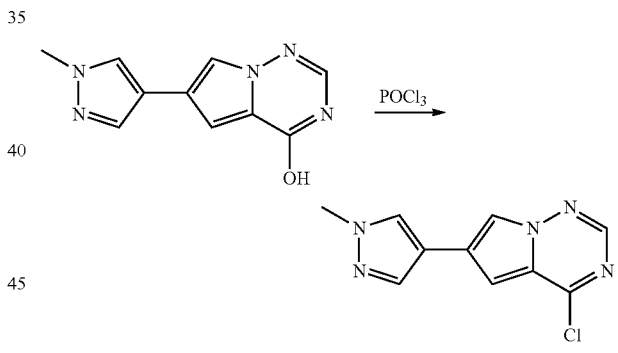

To a mixture of 6-(1-methyl-1H-pyrazol-4-yl)pyrrolo[2,1-f][1,2,4]triazin-4-ol (50.00 g, 232.33 mmol, 1.00 equiv) in POCl$_3$ (298.45 g, 1.95 mol, 8.38 equiv) was added DIPEA (70.00 g, 541.63 mmol, 2.33 equiv) dropwise at 20-25° C. over the course of 15 min. The mixture was stirred at 110° C. for 12 hr, after which TLC indicated that the reaction was complete. The excess POCl$_3$ was removed by evaporation and the crude was poured into ice water (1 L). The mixture was extracted with EtOAc (800 mL*2), then the organic phase was washed with brine (500 mL), dried over Na$_2$SO$_4$, and concentrated to give 4-chloro-6-(1-methyl-1H-pyrazol-4-yl)pyrrolo[2,1-f][1,2,4]triazine (41.0 g, 175.5 mmol, 75.5% yield) as a yellow solid. $^1$H-NMR (400 MHz, DMSO-d$_6$) δ ppm: 8.53 (s, 1H), 8.36 (s, 1H), 8.19 (s, 1H), 7.94 (s, 1H), 7.25 (s, 1H), 3.87 (s, 3H).

Step 3: Synthesis of 4-(6-(1-methyl-1H-pyrazol-4-yl)pyrrolo[2,1-f][1,2,4]triazin-4-yl)aniline

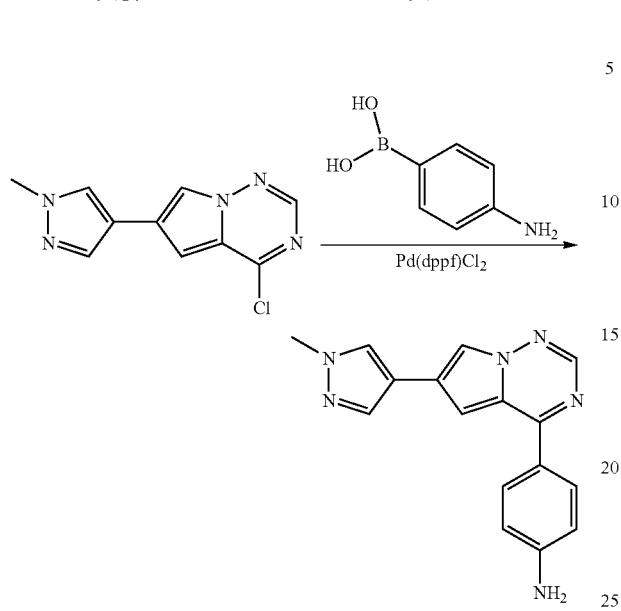

A suspension of 4-chloro-6-(1-methyl-1H-pyrazol-4-yl)pyrrolo[2,1-f][1,2,4]triazine (56.00 g, 239.66 mmol, 1.00 equiv), (4-aminophenyl)boronic acid (47.79 g, 275.61 mmol, 1.15 equiv), K$_2$CO$_3$ (66.25 g, 479.32 mmol, 2.00 equiv), and Pd(dppf)Cl$_2$·CH$_2$Cl$_2$ (5.60 g, 6.86 mmol, 0.03 equiv) in H$_2$O (300.00 mL) and 2-methyltetrahydrofuran (900.00 mL) was stirred at 70-75° C. for 3 hr under N$_2$. After TLC indicated that the reaction was complete, the mixture was filtered and the filtrate was extracted with EtOAc (800 mL*2). The combined organic phase was washed with brine (400 mL), dried over Na$_2$SO$_4$, and concentrated to give 4-(6-(1-methyl-1H-pyrazol-4-yl)pyrrolo[2,1-f][1,2,4]triazin-4-yl)aniline (36.0 g, 124.0 mmol, 51.7% yield) as a yellow solid. The crude was used in the next step without further purification. $^1$H-NMR (400 MHz, DMSO-d$_6$) δ ppm: 8.38 (s, 1H), 8.28 (s, 1H), 8.16 (s, 1H), 8.02-8.04 (d, J=8.4 Hz, 2H), 7.92 (s, 1H), 7.39 (s, 1H), 6.72-6.74 (d, J=8.4 Hz, 2H), 5.99 (s, 2H), 3.87 (s, 3H).

Step 4: Synthesis of 4-(6-(1-methyl-1H-pyrazol-4-yl)pyrrolo[2,1-f][1,2,4]triazin-4-yl)aniline hydrochloride

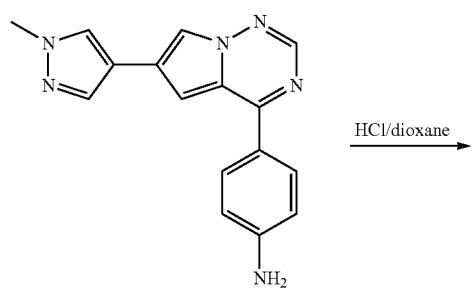

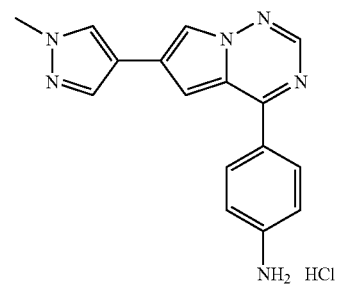

To a mixture of 4-(6-(1-methyl-1H-pyrazol-4-yl)pyrrolo[2,1-f][1,2,4]triazin-4-yl)aniline (26.00 g, 89.56 mmol, 1.00 equiv) in MeOH (50.00 mL) was added HCl/EtOAc (199.72 mmol, 2.23 equiv) dropwise at 20-25° C. for 15 min. A precipitate formed and was filtered, and the filter cake was washed with EtOAc (50 mL) and filtered again. The filter cake was collected to give 4-(6-(1-methyl-1H-pyrazol-4-yl)pyrrolo[2,1-f][1,2,4]triazin-4-yl)aniline hydrochloride (28.0 g, 85.7 mmol, 95.7% yield) as a red solid. $^1$H-NMR (400 MHz, DMSO-d$_6$) δ ppm: 8.74 (s, 1H), 8.54 (s, 1H), 8.28 (s, 1H), 8.10-8.12 (d, J=12 Hz, 2H), 8.02 (s, 1H), 7.86 (s, 1H), 7.00-7.03 (d, J=12 Hz, 2H), 5.03 (s, 24H), 3.88 (s, 3H).

Example 11: Synthesis of (4-cyanophenyl)-N-(4-(4,4,5,5-tetramethyl-1,3,2-dioxaborolan-2-yl)phenyl)methanesulfonamide Step 1: Synthesis of 2-methyl-1-(4-(4,4,5,5-tetramethyl-1,3,2-dioxaborolan-2-yl)-1H-pyrazol-1-yl)propan-2-ol

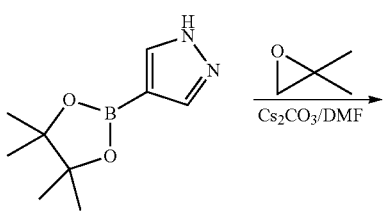

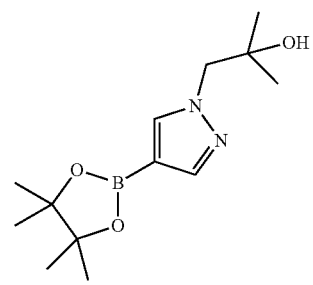

To the mixture of 4-(4,4,5,5-tetramethyl-1,3,2-dioxaborolan-2-yl)-1H-pyrazole (1.94 g, 10 mmol) and 2,2-dimethyloxirane (1.08 g, 15 mmol) in DMF (17 mL) was added Cs$_2$CO$_3$ (6.52 g, 20 mmol) at 25° C. The reaction was heated at 120° C. for 0.5 hr in a microwave reactor. After LCMS indicated the reaction was complete, the mixture was filtered and the filtrate was concentrated. The crude product was purified by flash silica gel chromatography to give 2-methyl-1-(4-(4,4,5,5-tetramethyl-1,3,2-dioxaborolan-2-yl)-1H-pyrazol-1-yl)propan-2-ol (1.82 g, yield: 68.4%) as a white solid. $^1$H-NMR (400 MHz, CDCl$_3$) δ ppm 7.83 (s, 1H), 7.71 (s, 1H), 4.08 (s, 2H), 1.25 (s, 6H), 1.16 (s, 12H).

Step 2: Synthesis of sodium (4-cyanophenyl)methanesulfonate

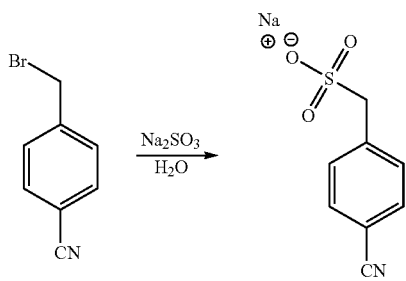

To a solution of 4-(bromomethyl)benzonitrile (1.96 g, 10 mmol) in water (8 mL) was added Na$_2$SO$_3$ (1.39 g, 11 mmol) at 0° C. The resultant mixture was stirred at room temperature for 12 h then concentrated to afford the title compound sodium (4-cyanophenyl)-methanesulfonate (2.19 g, crude) as a white solid. MS (ES+) NaC$_8$H$_6$NO$_3$S requires: 219. found: 196 [M−23].

Step 3: Synthesis of (4-cyanophenyl)methanesulfonyl chloride

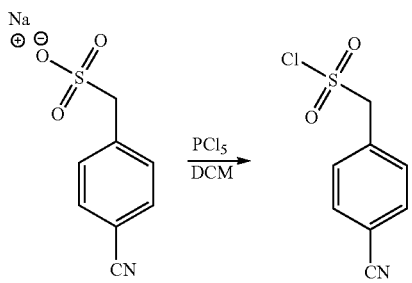

To a solution of sodium (4-cyanophenyl)methanesulfonate (440 mg, 2 mmol) in DCM (15 ml) was added PCl$_5$ (1.14 g, 5.5 mmol) at room temperature. The mixture was stirred at room temperature for 12 h, after which the mixture was quenched with water (10 mL) and extracted with DCM (10 ml*3). The organic layers were combined and concentrated to afford (4-cyanophenyl)methanesulfonyl chloride (440 mg, crude) as a yellow oil which was used in next step without further purification.

Step 4: Synthesis of (4-cyanophenyl)-N-(4-(4,4,5,5-tetramethyl-1,3,2-dioxaborolan-2-yl)phenyl)methanesulfonamide

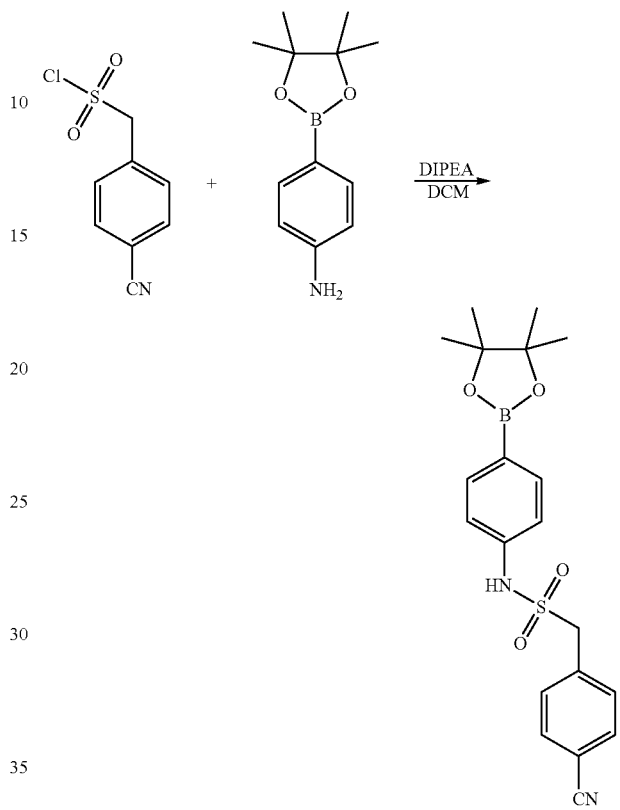

A mixture of (4-cyanophenyl)methanesulfonyl chloride (216 mg, 1 mmol), 4-(4,4,5,5-tetramethyl-1,3,2-dioxaborolan-2-yl)benzenamine (219 mg, 1 mmol) and DIPEA (400 mg, 3 mmol) in DCM (15 ml) was stirred at room temperature for 12 h, after which the mixture was diluted with DCM (50 mL) and washed with brine (50 mL). The organic layers were combined, dried over Na$_2$SO$_4$, and concentrated to give (4-cyanophenyl)-N-(4-(4,4,5,5-tetramethyl-1,3,2-dioxaborolan-2-yl)phenyl)methanesulfonamide (170 mg, 57%) as a brown oil. The material was used without further purification. MS (ES+) C$_{20}$H$_{23}$BN$_2$O$_4$S requires: 398. found: 399 [M+H]$^+$.

The synthetic protocols that can be used to prepare the compounds disclosed herein are indicated below. The NMR and LC MS data obtained for compounds disclosed herein are also shown below.

| Compound Number | Synthetic Method | 1H NMR | MS (M + 1) |
|---|---|---|---|
| 1 | 2 | | 369 |
| 2 | 2 | $^1$H-NMR (400 MHz, DMSO-d$_6$) δ ppm 10.25 (br. s., 1H), 8.52 (s, 1H), 8.42 (d, 1H, J = 1.6 Hz), 8.20-8.17 (m, 3H), 7.94 (s, 1H), 7.47-7.43 (m, 3H), 3.87 (s, 3H), 3.36 (heptet, 1H, J = 6.8 Hz), 1.28 (d, 6H, J = 6.8 Hz). | 397 |
| 3 | 1 | $^1$H-NMR (400 MHz, DMSO-d$_6$) δ ppm 10.62-10.61 (m, 1H), 8.53 (s, 1H), 8.44- | 409 |

| Compound Number | Synthetic Method | 1H NMR | MS (M + 1) |
|---|---|---|---|
| | | 8.42 (m, 1H), 8.21-8.19 (m, 3H), 7.95 (s, 1H), 7.89-7.87 (m, 2H), 7.48-7.46 (m, 1H), 7.39-7.33 (m, 4H),7.28-7.22 (m, 1H), 3.88 (s, 3H), 3.73 (s, 2H). | |
| 4 | 1 | ¹H-NMR (400 MHz, DMSO-d₆) δ ppm 10.62 (s, 1H), 8.56 (d, 1H, J = 1.2 Hz), 8.53 (s, 1H), 8.48 (dd, 1H, J = 4.8, 2.0 Hz), 8.44 (d, 1H, J = 1.6 Hz), 8.21 (d, 2H, J = 8.4 Hz), 8.20 (s, 1H), 7.96 (s, 1H), 7.87 (d, 2H, J = 8.8 Hz), 7.85(s, 1H), 7.79-7.77 (m, 1H), 7.48 (d, 1H, J = 1.6 Hz), 7.37 (dd, 1H, J = 7.6, 4.8 Hz), 3.87 (s, 3H), 3.80 (s, 2H). | 410 |
| 5 | 1 | ¹H-NMR (400 MHz, DMSO-d₆) δ ppm 10.65 (s, 1H), 8.54-8.52 (m, 2H), 8.44 (d, 1H, J = 1.6 Hz), 8.21 (d, 2H, J = 8.4 Hz), 8.20 (s, 1H), 7.96 (s, 1H), 7.88 (d, 2H, J = 8.8 Hz), 7.79-7.77 (m, 1H), 7.48 (d, 1H, J = 1.2 Hz), 7.43 (d, 1H, J = 8.0 Hz), 7.32-7.28 (m, 1H), 3.93 (s, 2H), 3.88 (s, 3H). | 410 |
| 6 | 1 | ¹H-NMR (400 MHz, CDCl₃) δ ppm 8.44 (s, 1H), 8.08 (d, 2H, J = 8.4 Hz), 7.96 (s, 1H, J = 1.2 Hz), 7.76 (s, 1H), 7.68 (d, 2H, J = 8.4 Hz), 7.69-7.67 (m, 1H), 7.64 (s, 1H), 7.50 (s, 1H), 7.44 (s, 1H), 7.06 (d, 1H, J = 1.6 Hz), 3.96 (s, 3H), 3.94 (s, 3H), 3.65 (s, 2H). | 413 |
| 7 | 1 | ¹H-NMR (400 MHz, DMSO-d₆) δ ppm 10.83 (s, 1H), 8.56 (s, 1H), 8.46 (d, 1H, J = 0.8 Hz), 8.27 (d, 2H, J = 8.4 Hz), 8.22 (s, 1H), 8.17 (s, 1H), 8.15 (s, 1H), 8.08-8.06 (m, 4H), 7.97 (s, 1H), 7.51 (d, 1H, J = 0.8 Hz), 3.889 (s, 3H). | 420 |
| 8 | 1 | ¹H-NMR (400 MHz, DMSO-d₆) δ ppm 10.51 (s, 1H), 8.52 (s, 1H), 8.42 (s, 1H), 8.20-8.18 (m, 3H), 7.94 (s, 1H), 7.85 (d, 2H, J = 8.8 Hz), 7.46 (d, 1H, J = 1.2 Hz), 7.24 (d, 2H, J = 8.0 Hz), 7.14 (d, 2H, J = 7.6 Hz), 3.86 (s, 3H), 3.65 (s, 2H), 2.27 (s, 3H) | 423 |
| 9 | 1 | ¹H-NMR (400 MHz, DMSO-d₆) δ ppm 9.05 (s, 1H), 8.50 (s, 1H), 8.40 (d, 1H, J = 1.2 Hz), 8.20 (s, 1H), 8.16 (d, 2H, J = 8.8 Hz), 7.95 (s, 1H), 7.68 (d, 2H, J = 8.8 Hz), 7.46 (d, 1H, J = 1.6 Hz), 7.37-7.24 (m, 5H), 6.82 (t, 1H, J = 6.0 Hz), 4.35 (d, 2H, J = 6.0 Hz), 3.88 (s, 3H) | 424 |
| 10 | 1 | ¹H-NMR (400 MHz, DMSO-d₆) δ ppm 10.32 (s, 1H), 8.51 (s, 1H), 8.41 (d, 1H, J = 1.2 Hz), 8.18 (s, 1H), 8.16 (d, 2H, J = 9.6 Hz), 7.98 (d, 2H, J = 8.8 Hz), 7.94 (s, 1H), 7.53 (d, 2H, J = 7.2 Hz), 7.44 (d, 1H, J = 1.2 Hz), 7.39-7.29 (m, 3H), 6.52 (d, 1H, J = 4.8 Hz), 5.17 (s, 1H), 3.86 (s, 3H). | 425 |
| 11 | 1 | ¹H-NMR (400 MHz, DMSO-d₆) δ ppm 10.56 (s, 1H), 8.53 (s, 1H), 8.43 (s, 1H), 8.22-8.19 (m, 3H), 7.95 (s, 1H), 7.86 (d, 2H, J = 8.8 Hz), 7.47 (s, 1H), 7.42-7.38 2(m, H), 7.20-7.15 (m, 2H), 3.88 (s, 3H), 3.73 (s, 2H) | 427 |
| 12 | 1 | ¹H-NMR (400 MHz, DMSO-d₆) δ ppm 10.67 (s, 1H), 8.56 (s, 1H), 8.45 (s, 1H), 8.26 (d, 2H, J = 8.4 Hz), 8.22 (s, 1H), 8.08-8.04 (m, 4H), 7.97 (s, 1H), 7.66 (d, 2H, J = 8.0 Hz), 7.51 (s, 1H), 3.89 (s, 3H). | 429 |
| 13 | 2 | ¹H-NMR (400 MHz, DMSO-d₆) δ ppm 8.48 (d, 1H, J = 2.8 Hz), 8.39 (s, 1H), 8.15 (s, 1H), 8.10 (d, 2H, J = 8.8 Hz), 7.91 (s, 1H), 7.86 (d, 2H, J = 7.2 Hz), 7.61-7.58 (m, 4H), 7.40 (d, 2H, J = 8.8 Hz), 7.33 (d, 2H, J = 8.8 Hz), 3.85 (s, 3H) | 431 |
| 14 | 2 | | 436 |
| 15 | 1 | ¹H-NMR (400 MHz, DMSO-d₆) δ ppm 10.41 (s, 1H), 8.52 (s, 1H), 8.42 (d, 1H, J = 1.2 Hz), 8.18 (s, 1H), 8.16 (d, 2H, J = 8.0 Hz), 7.96-7.93 (m, 3H), 7.50-7.38 (m, 5H), 4.91 (s, 1H), 3.86 (s, 3H), 3.39 (s, 3H). | 439 |
| 16 | 2 | | 443 |
| 17 | 1 | ¹H-NMR (400 MHz, CD₃OD) δ ppm 8.46 (s, 1H), 8.41 (s, 1H), 8.11 (d, 2H, J = 8.8 Hz), 8.06 (s, 1H), 7.92 (d, 2H, J = 5.6 Hz), 7.88 (s, 1H), 7.49 (s, 1H), 7.36 (s, 4H), 3.94 (s, 3H), 3.75 (s, 2H) | 443 |
| 18 | 1 | ¹H-NMR (400 MHz, DMSO) δ ppm 10.61 (s, 1H), 8.53 (s, 1H), 8.43 (s, 1H), 8.22-8.19 (m, 3H), 7.96 (s, 1H), 7.89-7.86 (m, 2H), 7.48-7.46 (m, 2H), 7.41-7.33 (m, 3H), 3.88 (s, 3H), 3.77 (s, 2H). | 443 |
| 19 | 1 | ¹H-NMR (400 MHz, DMSO-d₆) δ ppm 10.62 (s, 1H), 8.54 (s, 1H), 8.44 (s, 1H), 8.22 (s, 1H), 8.20 (s, 2H), 7.96 (s, 1H), 7.88 (s, 1H), 7.86 (s, 1H), 7.51-7.43 (m, 3H), 7.38-7.28 (m, 2H), 3.93 (s, 2H), 3.88 (s, 3H). | 443 |
| 20 | 1 | ¹H-NMR (400 MHz, DMSO-d₆) δ ppm 10.66 (s, 1H), 8.53 (s, 1H), 8.44 (d, 1H, J = 0.8 Hz), 8.39 (d, 1H, J = 2.0 Hz), 8.21 (d, 2H, J = 8.8 Hz), 8.20 (s, 1H), 7.95 (s, 1H), 7.86 (d, 2H, J = 8.8 Hz), 7.85 (d, 1H, J = 8.0 Hz), 7.52 (d, 1H, J = 8.0 Hz), 7.47 (d, 1H, J = 1.6 Hz), 3.88 (s, 3H), 3.83 (s, 2H). | 444 |
| 21 | 1 | ¹H-NMR (400 MHz, DMSO-d₆) δ ppm 9.19 (s, 1H), 9.00 (s, 1H), 8.53 (s, 1H), 8.42 (d, 1H, J = 1.6 Hz), 8.21-8.19 (m, 3H), 7.96 (s, 1H), 7.73 (d, 2H, J = 8.8 Hz), 7.53 (d, 2H, J = 9.2 Hz), 7.48 (d, 1H, J = 1.6 Hz), 7.36 (d, 2H, J = 9.2 Hz) | 444 |
| 22 | 2 | ¹H-NMR (500 MHz, DMSO-d₆) δ ppm 10.81 (s, 1H), 8.50 (s, 1H), 8.42 (d, 1H, J = 1.0 Hz), 8.18 (s, 1H), 8.11 (d, 2H, J = 8.5 Hz), 7.94 (s, 1H), 7.76 (d, 2H, J = 8.0 Hz), 7.42 (d, 1H, J = 1.5 Hz), 7.39 (d, 2H, J = 8.0 Hz), 7.33 (d, 2H, J = 8.5 Hz), 3.87 (s, 3H), 2.34 (s, 3H). | 445 |
| 23 | 1 | ¹H-NMR (400 MHz, DMSO-d₆) δ ppm 10.96 (s, 1H), 10.50 (s, 1H), 8.53 (s, 1H), 8.43 (d, 1H, J = 1.2 Hz), 8.21-8.19 (m, 3H), 7.95 (s, 1H), 7.90 (d, 2H, J = 8.8 Hz), 7.64 (d, 2H, J = 7.6 Hz), 7.47 (d, 1H, J = 1.2 Hz), 7.38 (d, 1H, J = 8.4 Hz), 7.31 (d, 1H, J = 2.4 Hz), 7.11-6.99 (m, 2H), 3.87 (s, 3H), 3.82 (s, 2H). | 448 |
| 24 | 2 | ¹H-NMR (400 MHz, DMSO-d₆) δ ppm 8.49 (s, 1H), 8.40 (d, 1H, J = 1.6 Hz), 8.15 (s, 1H), 8.10 (d, 2H, J = 8.8 Hz), 7.93-7.89 (m, 3H), 7.45-7.39 (m, 3H), 7.32 (d, 2H, J = 8.8 Hz), 3.84 (s, 3H) | 449 |
| 25 | 2 | | 455 |
| 26 | 2 | ¹H-NMR (400 MHz, DMSO-d₆) δ ppm 8.50 (s, 1H), 8.42 (s, 1H), 8.16 (s, 1H), 8.12-8.07 (m, 4H), 8.00 (d, 2H, J = 7.6 Hz), 7.91 (s, 1H), 7.40 (d, 1H), 7.34 (d, 2H, J = 7.6 Hz), 3.85 (s, 3H) | 456 |
| 27 | 1 | ¹H-NMR (400 MHz, DMSO-d₆) δ ppm 10.58 (s, 1H), 8.71 (s, 1H), 8.59 (s, 1H), 8.28 (d, 2H, J = 8.8 Hz), 8.05-7.98 (m, 2H), 7.88 (d, 2H, J = 8.8 Hz), 7.72 (s, 1H), 7.42 (d, 2H, J = 8.4 Hz), 7.38 (d, 2H, J = 8.8 Hz), 7.32-7.26 (m, 2H), 3.74 (s, 2H). | 457 |
| 28 | 1 | ¹H-NMR (400 MHz, CDCl₃) δ ppm 8.45 (s, 1H), 8.07 (d, 2H, J = 8.4 Hz), 7.98 (d, 1H, J = 1.6 Hz), 7.76 (s, 1H), 7.68 (d, 2H, J = 8.8 Hz), 7.64 (s, 1H), 7.39-7.33 (m, 5H), 7.07 (d, 1H, J = 1.6 Hz), 3.97 (s, 3H), 3.76 (q, 1H, J = 7.2 Hz), 1.61 (d, 3H, J = 6.8 Hz) | 457 |

| Compound Number | Synthetic Method | 1H NMR | MS (M + 1) |
|---|---|---|---|
| 29 | 1 | ¹H-NMR (400 MHz, DMSO-d₆) δ ppm 10.46 (s, 1H), 8.52 (s, 1H), 8.42 (s, 1H), 8.19-8.16 (m, 3H), 7.94 (s, 1H), 7.85 (d, 2H, J = 8.8 Hz), 7.45-7.39 (m, 5H), 3.90 (q, 4H, J = 7.2 Hz), 3.86 (s, 3H), 3.44 (d, 3H, J = 7.2 Hz). | 457 |
| 30 | 1 | ¹H-NMR (400 MHz, CDCl₃) δ ppm 8.44 (s, 1H), 8.07 (d, 2H, J = 8.8 Hz), 7.96 (d, 1H, J = 1.2 Hz), 7.75 (s, 1H), 7.66 (d, 2H, J = 8.4 Hz), 7.63 (s, 1H), 7.38-7.32 (m, 5H), 7.05 (d, 1H, J = 1.6 Hz), 3.96 (s, 3H), 3.73 (q, 1H, J = 7.2 Hz), 1.60 (d, 3H, J = 6.8 Hz). | 457 |
| 31 | 4 | ¹H-NMR (400 MHz, 6d-DMSO) δ ppm 8.53 (s, 1H), 8.43 (d, 1H, J = 1.2 Hz), 8.19 (d, 2H, J = 8.4 Hz), 8.19 (s, 1H), 7.95 (s, 1H), 7.89 (d, 2H, J = 8.4 Hz), 7.53 (d, 2H, J = 8.4 Hz), 7.46 (d, 1H, J = 1.2 Hz), 7.42 (d, 2H, J = 8.4 Hz), 4.63 (s, 1H), 3.87 (s, 3H). | 458 |
| 32 | 4 | ¹H-NMR (400 MHz, DMSO-d₆) δ ppm 10.37 (s, 1H), 8.53 (s, 1H), 8.44 (s, 1H), 8.20 (s, 1H), 8.18 (d, 2H, J = 8.4 Hz), 7.98 (d, 2H, J = 8.4 Hz), 7.95 (s, 1H), 7.57 (d, 2H, J = 8.4 Hz), 7.46 (s, 1H), 7.45 (d, 2H, J = 8.4 Hz), 6.66 (s, 1H), 5.21 (s, 1H), 3.87 (s, 3H). | 459 |
| 33 | 4 | ¹H-NMR (400 MHz, DMSO-d₆) δ ppm 8.54 (s, 1H), 8.44 (s, 1H), 8.20 (s, 1H), 8.19 (d, 2H, J = 6.8 Hz), 7.98 (d, 2H, J = 6.8 Hz), 7.96 (s, 1H), 7.57 (d, 2H, J = 6.8 Hz), 7.46 (s, 1H), 7.45 (d, 2H, J = 6.8 Hz), 5.21 (s, 2H), 3.88 (s, 3H). | 459 |
| 34 | 4 | ¹H-NMR (400 MHz, DMSO-d₆) δ ppmδ ppm 10.36 (s, 1H), 8.53 (s, 1H), 8.44 (s, 1H), 8.20 (s, 1H), 8.18 (d, 2H, J = 8.4 Hz), 7.98 (d, 2H, J = 8.4 Hz), 7.95 (s, 1H), 7.57 (d, 2H, J = 8.4 Hz), 7.46 (s, 1H), 7.45 (d, 2H, J = 8.4 Hz), 6.66 (s, 1H), 5.21 (s, 1H), 3.87 (s, 3H). | 459 |
| 35 | 2 | ¹H-NMR (400 MHz, DMSO-d₆) δ ppm 8.46 (s, 1H), 8.37 (s, 1H), 8.15 (s, 1H), 8.07 (d, 2H, J = 8.8 Hz), 7.91 (s, 1H), 7.76 (d, 2H, J = 8.8 Hz), 7.39 (s, 1H), 7.26 (d, 2H, J = 8.4 Hz), 7.06 (d, 2H, J = 8.8 Hz), 3.84 (s, 3H), 3.77 (s, 3H) | 461 |
| 36 | 2 | ¹H NMR (400 MHz, DMSO-d₆) δ ppm 10.93 (s, 1H), 8.50 (s, 1H), 8.41 (d, 1H, J = 1.2 Hz), 8.17 (s, 1H), 8.12 (d, 2H, J = 8.7 Hz), 7.93 (s, 1H), 7.85 (d, 2H, J = 8.6 Hz), 7.67 (d, 2H, J = 8.6 Hz), 7.41 (d, 1H, J = 1.3 Hz), 7.32 (d, 2H, J = 8.6 Hz), 3.86 (s, 3H) | 465 |
| 37 | 2 | ¹H-NMR (400 MHz, DMSO-d₆) δ ppm 8.49 (s, 1H), 8.40 (s, 1H), 8.15-8.11 (m, 3H), 7.91 (s, 1H), 7.85 (s, 1H), 7.80 (d, 1H, J = 7.6 Hz), 7.71 (d, 1H, J = 8.0 Hz), 7.63 (t, 1H, J = 8.0 Hz), 7.40 (s, 1H), 7.34 (d, 2H, J = 8.4 Hz), 3.84 (s, 3H) | 465 |
| 38 | 2 | ¹H-NMR (400 MHz, CD₃OD) δ ppm 8.36 (s, 1H), 8.22 (s, 1H), 8.19 (d, 1H, J = 7.2 Hz), 8.01 (s, 2H), 7.99 (s, 1H), 7.86 (s, 1H), 7.56 (d, 2H, J = 4.0 Hz), 7.50-7.48 (m, 1H), 7.37 (d, 2H, J = 8.8 Hz), 7.26 (s, 1H), 3.92 (s, 3H) | 465 |
| 39 | 1 | ¹H-NMR (400 MHz, DMSO-d₆) δ ppm 9.55 (s, 1H), 8.51 (s, 1H), 8.42 (s, 1H), 8.18-8.14 (m, 3H), 7.93 (s, 1H), 7.84 (d, 2H, J = 8.4 Hz), 7.43 (br. s, 5H), 3.86 (s, 3H), 1.52-1.50 (m, 2H), 1.17-1.15 (m, 2H). | 469 |
| 40 | 2 | ¹H NMR (500 MHz, DMSO-d₆) δ ppm 10.45 (s, 1H), 8.55 (s, 1H), 8.45 (s, 1H), 8.22-8.20 (m, 3H), 7.97 (s, 1H), 7.87 (d, 2H, J = 8.0 Hz), 7.54-7.46 (m, 3H), 7.39 (d, 2H, J = 8.5 Hz), 4.77 (s, 2H), 3.87 (s, 3H). | 470 |
| 41 | 1 | ¹H-NMR (400 MHz, DMSO-d₆) δ ppm 9.50 (s, 1H), 8.53 (s, 1H), 8.44 (d, 1H, J = 0.4 Hz), 8.20 (s, 1H), 8.16 (d, 2H, J = 8.4 Hz), 7.95 (s, 1H), 7.90 (d, 2H, J = 8.4 Hz), 7.46 (s, 1H), 7.44 (d, 2H, J = 8.4 Hz), 7.39 (d, 2H, J = 8.4 Hz), 3.88 (s, 3H), 1.60 (s, 6H). | 471 |
| 42 | 1 | ¹H-NMR (400 MHz, DMSO-d₆) δ ppm 10.54 (s, 1H), 8.53 (s, 1H), 8.43 (d, 1H, J = 1.2 Hz), 8.19 (s, 1H), 8.17 (d, 2H, J = 8.4 Hz), 7.95 (s, 1H), 7.86 (d, 2H, J = 8.8 Hz), 7.45-7.41 (m, 5H), 3.88 (s, 3H), 3.70-3.65 (m, 1H), 2.10-2.04 (m, 1H), 1.77-1.69 (m, 1H), 0.89 (t, 3H, J = 7.2 Hz). | 471 |
| 43 | 1 | ¹H-NMR (400 MHz, CDCl₃) δ ppm 8.45 (s, 1H), 8.08 (d, 2H, J = 8.4 Hz), 7.97 (d, 1H, J = 1.6 Hz), 7.76 (s, 1H), 7.69 (d, 2H, J = 8.8 Hz), 7.64 (s, 1H), 7.38-7.32 (m, 5H), 7.05 (d, 1H, J = 1.6 Hz), 3.96 (s, 3H), 3.41 (t, 1H, J = 7.6 Hz), 2.31-2.22 (m, 1H), 1.90-1.83 (m, 1H), 0.95 (t, 3H, J = 7.2 Hz). | 471 |
| 44 | 1 | ¹H-NMR (400 MHz, DMSO-d₆) δ ppm 10.55 (s, 1H), 8.53 (s, 1H), 8.44 (d, 1H, J = 0.8 Hz), 8.19 (s, 1H), 8.18 (d, 2H, J = 8.8 Hz), 7.95 (s, 1H), 7.87 (d, 2H, J = 8.8 Hz), 7.46-7.41 (m, 5H), 3.88 (s, 3H), 3.68 (dd, 1H, J = 7.6, 8.4 Hz), 2.09-2.06 (m, 1H), 1.75-1.71 (m, 1H), 0.89 (t, 3H, J = 7.2 Hz). | 471 |
| 45 | 4 | ¹H-NMR (400 MHz, CDCl₃) δ ppm 10.09 (s, 1H), 8.46 (s, 1H), 8.11 (d, 1H, J = 8.4 Hz), 7.97 (d, 1H, J = 1.6 Hz), 7.81 (d, 2H, J = 8.4 Hz), 7.76 (s, 1H), 7.64 (s, 1H), 7.53 (dd, 2H, J = 8.4, 2.0 Hz), 7.36 (dd, 2H, J = 8.4, 2.0 Hz), 7.07 (d, 1H, J = 1.6 Hz), 3.96 (s, 3H), 3.70-3.60 (m, 2H), 1.90 (s, 3H) | 472 |
| 46 | 4 | ¹H-NMR (400 MHz, CDCl₃) δ ppm 10.09 (s, 1H), 8.46 (s, 1H), 8.11 (d, 1H, J = 8.4 Hz), 7.97 (d, 1H, J = 1.6 Hz), 7.81 (d, 2H, J = 8.4 Hz), 7.76 (s, 1H), 7.64 (s, 1H), 7.53 (dd, 2H, J = 8.4, 2.0 Hz), 7.36 (dd, 2H, J = 8.4, 2.0 Hz), 7.07 (d, 1H, J = 1.6 Hz), 3.96 (s, 3H), 3.70-3.60 (m, 2H), 1.90 (s, 3H). | 472 |
| 47 | 4 | ¹H-NMR (400 MHz, CDCl₃) δ ppm 10.10 (s, 1H), 8.46 (s, 1H), 8.11 (d, 1H, J = 8.4 Hz), 7.97 (d, 1H, J = 1.6 Hz), 7.81 (d, 2H, J = 8.4 Hz), 7.76 (s, 1H), 7.64 (s, 1H), 7.53 (dd, 2H, J = 8.4, 2.0 Hz), 7.36 (dd, 2H, J = 8.4, 2.0 Hz), 7.07 (d, 1H, J = 1.6 Hz), 3.96 (s, 3H), 1.90 (s, 3H). | 472 |
| 48 | 1 | ¹H-NMR (400 MHz, DMSO) δ ppm 10.50 (s, 1H), 8.54 (s, 1H), 8.44 (d, 1H, J = 1.2 Hz), 8.19 (s, 1H), 8.18 (d, 2H, J = 7.6 Hz), 7.95 (d, 2H, J = 8.4 Hz), 7.95 (s, 1H), 7.55 (d, 2H, J = 8.4 Hz), 7.48 (d, 2H, J = 8.4 Hz), 7.46 (d, 1H, J = 1.2 Hz), 4.97 (s, 1H), 3.87 (s, 3H), 3.41 (s, 3H). | 473 |
| 49 | 4 | ¹H-NMR (400 MHz, DMSO-d₆) δ ppm 10.14 (s, 1H), 8.51 (s, 1H), 8.42 (s, 1H), 8.18 (s, 1H), 8.15 (d, 2H, J = 8.4 Hz), 8.00 (d, 2H, J = 8.4 Hz), 7.94 (s, 1H), 7.65 (d, 2H, J = 8.4 Hz), 7.43 (s, 1H), 7.42 (d, 2H, J = 8.4 Hz), 6.72 (s, 1H), 3.86 (s, 3H), 1.74 (s, 3H). | 473 |
| 50 | 4 | ¹H-NMR (400 MHz, DMSO-d₆) δ ppm 10.15 (s, 1H), 8.53 (s, 1H), 8.43 (d, 1H, J = 1.2 Hz), 8.20 (s, 1H), 8.16 (d, 2H, J = 8.8 Hz), 8.01 (d, 2H, J = 8.8 Hz), 7.95 (s, 1H), 7.66 (d, 2H, J = 8.8 Hz), 7.45 (s, | 473 |

| Compound Number | Synthetic Method | 1H NMR | MS (M + 1) |
|---|---|---|---|
| | | 1H), 7.44 (d, 2H, J = 8.8 Hz), 6.71 (br. s., 1H), 3.87 (s, 3H), 1.75 (s, 3H). | |
| 51 | 4 | ¹H-NMR (400 MHz, CDCl₃) δ ppm 8.85 (s, 1H), 8.43 (s, 1H), 8.07 (d, 1H, J = 8.4 Hz), 7.98-7.96 (m, 1H), 7.75 (d, 2H, J = 8.4 Hz), 7.74 (s, 1H), 7.63 (s, 1H), 7.62 (d, 2H, J = 8.4 Hz), 7.36 (d, 2H, J = 8.4 Hz), 7.05-7.04 (m, 1H), 3.96 (s, 3H), 3.61 (s, 1H), 1.94 (s, 3H). | 473 |
| 52 | 1 | ¹H-NMR (400 MHz, CDCl₃) δ ppm 8.75 (s, 1H), 8.46 (s, 1H), 8.12 (d, 2H, J = 8.4 Hz), 7.98 (d, 1H, J = 1.6 Hz), 7.80 (d, 2H, J = 9.2 Hz), 7.76 (s, 1H), 7.64 (s, 1H), 7.41 (q, 4H, J = 8.4 Hz), 7.07 (s, 1H), 4.77 (s, 1H), 3.97 (s, 3H), 3.49 (s, 3H). | 473 |
| 53 | 1 | ¹H-NMR (400 MHz, DMSO) δ ppm 10.49 (s, 1H), 8.54 (s, 1H), 8.44 (s, 1H), 8.19 (d, 2H, J = 8.4 Hz), 8.19 (s, 1H), 7.95 (d, 2H, J = 8.4 Hz), 7.95 (s, 1H), 7.55 (d, 2H, J = 8.4 Hz), 7.48 (d, 2H, J = 8.4 Hz), 7.46 (s, 1H), 4.97 (s, 1H), 3.88 (s, 3H), 3.41 (s, 3H). | 473 |
| 54 | 1 | ¹H-NMR (400 MHz, DMSO-d₆) δ ppm 10.62 (s, 1H), 8.52 (s, 1H), 8.42 (s, 1H), 8.21-8.19 (m, 3H), 7.94 (s, 1H), 7.85 (d, 2H, J = 8.4 Hz), 7.63 (s, 1H), 7.50-7.42 (m, 3H), 3.92 (s, 2H), 3.86 (s, 3H). | 478 |
| 55 | 3 | ¹H-NMR (400 MHz, CDCl₃) δ ppm 8.13 (s, 1H), 8.04 (d, 2H, J = 8.8 Hz), 7.86 (d, 1H, J = 1.6 Hz), 7.63-7.57 (m, 1H), 7.54-7.50 (m, 4H), 7.47-7.44 (m, 2H), 7.28-7.26 (m, 2H), 7.02 (t, 2H, J = 8.8 Hz), 5.34 (s, 1H) | 479 |
| 56 | 2 | ¹H-NMR (400 MHz, CD₃OD) δ ppm 8.39 (s, 1H), 8.25 (s, 1H), 7.98 (s, 1H), 7.88 (d, 2H, J = 8.8 Hz), 7.83 (s, 1H), 7.70 (t, 1H, J = 8.4 Hz), 7.58 (d, 2H, J = 8.8 Hz), 7.18-7.11 (m, 1H), 6.98 (br.s, 1H), 3.91 (s, 3H) | 483 |
| 57 | 2 | ¹H-NMR (400 MHz, CD₃OD) δ ppm 8.41 (s, 1H), 8.26 (s, 1H), 8.03 (s, 1H), 7.97 (d, 1H, J = 8.4 Hz), 7.89 (s, 1H), 7.85-7.83 (m, 3H), 7.76-7.71 (m, 1H), 7.56-7.53 (m, 2H),7.32 (s, 1H), 3.93 (s, 3H) | 483 |
| 58 | 1 | ¹H-NMR (400 MHz, CDCl₃) δ ppm 8.44 (s, 1H), 8.05 (d, 2H, J = 8.0 Hz), 7.96 (s, 1H), 7.82 (s, 1H), 7.76 (s, 1H), 7.71 (d, 2H, J = 8.4 Hz), 7.63 (s, 1H), 7.35-7.26 (m, 4H), 7.04 (s, 1H), 3.95 (s, 3H), 3.03 (d, 1H, J = 10.0 Hz), 2.51-2.46 (m, 1H), 1.13 (d, 3H, J = 6.0 Hz), 0.75 (d, 3H, J = 6.4 Hz). | 485 |
| 59 | 4 | ¹H-NMR (400 MHz, DMSO-d₆) δ ppm 10.50 (s, 1H), 8.53 (s, 1H), 8.44 (d, 1H, J = 1.2 Hz), 8.19-8.16 (m, 3H), 7.95 (s, 1H), 7.91 (d, 2H, J = 8.8 Hz), 7.56 (d, 2H, J = 8.4 Hz), 7.46 (d, 2H, J = 8.4 Hz), 7.45 (s, 1H), 3.99 (s, 1H), 3.88 (s, 3H), 2.24 (s, 6H). | 486 |
| 60 | 1 | ¹H-NMR (400 MHz, DMSO) δ ppm 10.60 (s, 1H), 8.53 (s, 1H), 8.47 (s, 1H), 8.23-8.20 (m, 3H), 7.97 (s, 1H), 7.87 (d, J = 8.4 Hz, 2H), 7.51 (d, J = 1.6 Hz, 1H), 7.43-7.38 (m, 4H), 4.78 (s, 1H), 4.04 (s, 2H), 3.74 (s, 2H), 1.10 (s, 6H). | 501 |
| 61 | 1 | ¹H-NMR (400 MHz, DMSO) δ ppm 10.77 (s, 1H), 8.65 (d, J = 1.2 Hz, 1H), 8.57 (s, 1H), 8.26 (d, J = 9.2 Hz, 2H), 7.91-7.86 (m, 4H), 7.66 (d, J = 1.2 Hz, 1H), 7.41 (s, 4H), 7.04 (d, J = 8.4 Hz, 2H), 3.77 (s, 2H), 1.33 (s, 9H) | 511 |
| 62 | 2 | ¹H-NMR (400 MHz, CD₃OD) δ ppm 8.39 (s, 1H), 8.35 (s, 1H), 8.05 (d, 2H, J = 8.8 Hz), 7.85 (d, 2H, J = 8.8 Hz), 7.70 (d, 2H, J = 8.8 Hz), 7.54 (d, 2H, J = 8.8 Hz), 7.38-7.36 (m, 3H), 6.96 (d, 2H, J = 8.8 Hz), | 519 |
| | | 4.67-4.61 (m, 1H), 1.33 (d, 6H, J = 6.0 Hz) | |
| 63 | 3 | ¹H-NMR (400 MHz, CD₃OD) δ ppm 8.42 (s, 1H), 8.30 (br.s, 1H), 7.99 (d, 2H, J = 8.8 Hz), 7.85 (d, 2H, J = 8.4 Hz), 7.53 (d, 2H, J = 8.4 Hz), 7.37 (d, 2H, J = 8.8 Hz), 7.31 (s, 1H), 6.40-6.38 (m, 1H), 4.22 (br.s, 2H), 3.82-3.74 (m, 2H), 2.64-2.56 (m, 2H), 2.51-2.43 (m, 2H), 1.17-1.11 (m, 3H) | 522 |
| 64 | 3 | ¹H-NMR (400 MHz, CD₃OD) δ ppm 8.39 (s, 1H), 8.17 (s, 1H), 8.00 (d, 2H, J = 8.0 Hz), 7.84 (d, 2H, J = 8.0 Hz), 7.53 (d, 2H, J = 8.8 Hz), 7.35 (d, 2H, J = 8.4 Hz), 7.21 (s, 1H), 6.34 (br.s, 1H), 4.17-4.14 (m, 4H), 3.70 (br.s, 2H), 2.58 (br.s, 2H), 1.28 (t, 3H, J = 7.2 Hz) | 538 |
| 65 | 2 | | 539 |
| 66 | 3 | ¹H-NMR (400 MHz, CDCl₃) δ ppm 8.06 (s, 1H), 7.97 (d, 2H, J = 8.4 Hz), 7.85 (d, 1H, J = 1.2 Hz), 7.56-7.42 (m, 7H), 7.38 (d, 2H, J = 7.2 Hz), 7.24 (d, 1H, J = 7.2 Hz), 7.19 (s, 1H), 5.30 (s, 1H), 4.30-4.15 (m, 4H), 2.45-2.23 (m, 2H) | 544 |

Biochemical Activity of Compounds

In order to assess the activity of chemical compounds against the relevant kinase of interest, the Caliper Life-Sciences electrophoretic mobility shift technology platform is used. Fluorescently labeled substrate peptide is incubated in the presence of kinase and ATP so that a reflective proportion of the peptide is phosphorylated. At the end of the reaction, the mix of phosphorylated (product) and non-phosphorylated (substrate) peptides are passed through the microfluidic system of the Caliper EZ Reader 2, under an applied potential difference. The presence of the phosphate group on the product peptide provides a difference in mass and charge between those of the substrate peptide, resulting in a separation of the substrate and product pools in the sample. As the pools pass a LEDS within the instrument, these pools are detected and resolved as separate peaks. The ratio between these peaks therefore reflects the activity of the chemical matter at that concentration in that well, under those conditions.

Kit D816V assay at Km: In each well of a 384-well plate, 0.04 ng/ul (0.5 nM) of D816V Kit (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLYWSFPAKKK-NH2) and 15 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings:—1.9 psi, upstream voltage—700, downstream voltage—3000, post sample sip 35s). Data was normalized to 0% and 100% inhibition controls and the IC50 or EC50 calculated using a 4-parameter fit using GraphPad Prism.

Cellular Activity of Compounds

HMC1.2 Autophosphorylation Assay:

10,000 HMC1.2 cells were incubated in 22 ul culture media (phenol-red free IMDM, no serum) in each well of a 384-well plate and serum starved overnight in a tissue culture incubator (5% CO₂, 37° C.). A 10-point dose concentration series of compound (25 uM-95.4 pM) were then added to the cells in a volume of 3.1 ul to each well (0.25% DMSO final concentration). After 90 minutes, 6 ul of 5× AlphaLISA Lysis Buffer (Perkin Elmer) supplemented with a protease and phosphatase inhibitor cocktail (Cell Signaling Technologies) was added to each well and shaken at 450 rpm for 15 minutes at 4° C. 10 ul of phospho-Y719 c-Kit and total c-Kit antibodies (15 nM final concentration, Cell Signaling Technologies) and 50 ug/ml AlphaLISA rabbit acceptor beads (Perkin Elmer) were added to each well and shaken at 300 rpm at room temperature for 2 hours. 10 ul of 100 ug/ml streptavidin donor beads (Perkin Elmer) were added to each well, blocked from light with aluminum adhesive and shaken at 300 rpm at room temperature for 2 hours. Fluorescence signal was obtained on Envision (Perkin Elmer) by AlphaScreen 384 well HTS protocol. Data was normalized to 0% and 100% inhibition controls and the IC50 was calculated using Four Parameter Logistic IC50 curve fitting.

The Table below shows the activity of compounds in a Mast cell leukemia cell line, HMC 1.2. This cell line contains Kit mutated at positions V560G and D816V resulting in constitutive activation of the kinase. The following compounds were tested in an assay to measure direct inhibition of Kit D816V kinase activity by assaying Kit autophosphorylation at tyrosine 719 on the Kit protein.

In the Table below, for KIT D816V activity, the following designations are used: <1.00 nM=A; 1.01-10.0 nM=B; 10.01-100.0 nM=C; >100 nM=D; and ND=not determined. For cellular activity, the following designations are used: <10 nM=A; 10.01-100 nM=B; 100.01-1000 nM=C; 1000-10000 nM=D, >10000.01 nM=E; and ND=not determined.

| Compound Number | Biochemical Activity D816V IC50 (nM) | Cellular Activity IC50 (nM) |
|---|---|---|
| 1 | B | D |
| 2 | C | E |
| 3 | B | B |
| 4 | B | D |
| 5 | C | D |
| 6 | C | D |
| 7 | C | ND |
| 8 | B | B |
| 9 | C | C |
| 10 | A | ND |
| 11 | B | B |
| 12 | D | ND |
| 13 | B | C |
| 14 | B | C |
| 15 | B | ND |
| 16 | B | C |
| 17 | B | B |
| 18 | B | C |
| 19 | B | C |
| 20 | B | B |
| 21 | D | ND |
| 22 | B | B |
| 23 | B | B |
| 24 | B | C |
| 25 | C | D |
| 26 | B | D |
| 27 | C | D |
| 28 | B | A |
| 29 | B | A |
| 30 | C | C |
| 31 | B | A |
| 32 | A | A |
| 33 | B | A |
| 34 | B | B |
| 35 | B | C |
| 36 | A | B |
| 37 | C | C |
| 38 | C | D |
| 39 | C | C |
| 40 | A | B |
| 41 | A | B |
| 42 | B | A |
| 43 | B | B |
| 44 | C | C |
| 45 | B | A |
| 46 | B | A |
| 47 | B | A |
| 48 | A | A |
| 49 | B | A |
| 50 | C | C |
| 51 | B | B |
| 52 | B | B |
| 53 | C | C |
| 54 | B | A |
| 55 | D | D |
| 56 | B | C |
| 57 | C | D |
| 58 | C | B |
| 59 | B | B |
| 60 | B | B |
| 61 | C | D |
| 62 | C | D |
| 63 | A | B |
| 64 | B | B |
| 65 | C | C |
| 66 | D | D |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound of Formula I:

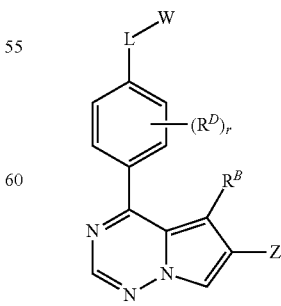

or a pharmaceutically acceptable salt thereof, wherein:

W is selected from hydrogen and

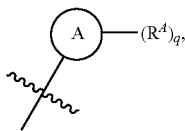

wherein Ring A is selected from monocyclic or bicyclic aryl, monocyclic or bicyclic heteroaryl, cycloalkyl, and heterocyclyl;

Z is selected from $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic or bicyclic heterocyclylalkyl, wherein each of $C_1$-$C_6$ alkyl, cycloalkyl, monocyclic or bicyclic aryl, monocyclic or bicyclic aralkyl, monocyclic or bicyclic heteroaryl, monocyclic or bicyclic heterocyclyl, and monocyclic and bicyclic heterocyclylalkyl is independently substituted with 0-5 occurrences of $R^C$;

L is selected from —N($R^1$)—C(O)—, —N($R^1$)C(O)N($R^1$)—, —N($R^1$)C(O)N($R^1$)—($C_1$-$C_6$ alkylene)-, N($R^1$)—($C_1$-$C_6$ alkylene)-, —N($R^1$)—C(O)—($C_1$-$C_6$ alkylene)-, —N($R^1$)—S(O)$_2$ and —N($R^1$)—S(O)$_2$—($C_1$-$C_6$ alkylene)-, wherein each $C_1$-$C_6$ alkylene is independently substituted with 0-5 occurrences of $R^2$;

each $R^A$ is independently selected from $C_1$-$C_6$ alkyl, $C_1$-$C_6$ alkoxy, halo, $C_1$-$C_6$ haloalkyl, $C_1$-$C_6$ hydroxyalkyl, $C_1$-$C_6$ heteroalkyl, —N($R^1$)($R^1$), cyano, and —O$R^1$;

each $R^B$ is independently selected from hydrogen, $C_1$-$C_6$ alkyl, $C_3$-$C_6$ cycloalkyl, hydroxyl, halo, $C_1$-$C_6$ alkoxy, $C_1$-$C_6$ haloalkyl, —N($R^1$)($R^1$), and cyano;

each $R^C$ is independently selected from $C_1$-$C_6$ alkyl, $C_2$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, monocyclic or bicyclic aryl, monocyclic or bicyclic aryloxy, monocyclic or bicyclic aralkyl, monocyclic or bicyclic heterocyclyl, monocyclic or bicyclic heterocyclylalkyl, nitro, cyano, —C(O)$R^1$, —OC(O)$R^1$, —C(O)O$R^1$, —S$R^1$, —S(O)$_2$$R^1$, —S(O)$_2$—N($R^1$)($R^1$), —($C_1$-$C_6$ alkylene)-S(O)$_2$—N($R^1$)($R^1$), —N($R^1$)($R^1$), —C(O)—N($R^1$)($R^1$), —N($R^1$)($R^1$)—C(O)$R^1$, ($C_1$-$C_6$ alkylene)-N($R^1$)—C(O)$R^1$, —N$R^1$S(O)$_2$$R^1$, —P(O)($R^1$)($R^1$), and —O$R^1$, wherein each of $C_1$-$C_6$ heteroalkyl, $C_1$-$C_6$ haloalkyl, $C_1$-$C_6$ haloalkoxy, $C_1$-$C_6$ alkyl, $C_1$-$C_6$ alkynyl, cycloalkyl, monocyclic or bicyclic aryl, monocyclic or bicyclic aryloxy, monocyclic or bicyclic aralkyl, monocyclic or bicyclic heterocyclyl, and monocyclic or bicyclic heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^D$ is independently selected from halo, $C_1$-$C_6$ alkyl, $C_3$-$C_6$ cycloalkyl, hydroxyl, halo, $C_1$-$C_6$ alkoxy, $C_1$-$C_6$ haloalkyl, —N($R^2$)($R^2$), and cyano;

each $R^1$ is independently selected from hydrogen, hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, $C_1$-$C_6$ thioalkyl, —NR"R", cycloalkyl, cycloalkylalkyl, heterocyclyl, and heterocyclylalkyl, wherein each of $C_1$-$C_6$ alkyl, cycloalkyl, and heterocyclyl is independently substituted with 0-5 occurrences of $R^b$; or 2 $R^1$ together with the atom(s) to which they are attached form a cycloalkyl or heterocyclyl ring;

each $R^2$ is independently selected from hydroxyl, $C_1$-$C_6$ alkyl, $C_1$-$C_6$ alkoxyl, —NR'R'; or 2 $R^2$ together with the atom(s) to which they are attached form a cycloalkyl or heterocyclyl ring;

each $R^a$ and $R^b$ is independently selected from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein cycloalkyl is substituted with 0-5 occurrences of R';

each R' is independently selected from hydrogen, $C_1$-$C_6$ alkyl, $C_1$-$C_6$ alkoxyl, $C_1$-$C_6$ heteroalkyl, halo, hydroxyl, $C_1$-$C_6$ haloalkyl, $C_1$-$C_6$ hydroxyalkyl, cycloalkyl, and cyano; or 2 R' together with the atom(s) to which they are attached form a cycloalkyl or heterocyclyl ring;

each R" is hydrogen, $C_1$-$C_6$ alkyl, —C(O)—$C_1$-$C_6$ alkyl, —C(O)—NR'R'R, or —C(S)—NR'R'; and each q and r is independently 0, 1, 2, 3, or 4.

2. The compound of claim 1, or a pharmaceutically acceptable salt thereof, wherein the compound is a compound of Formula II:

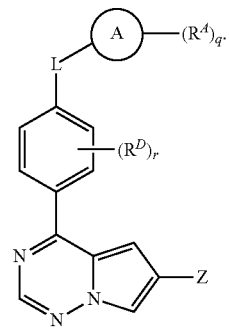

wherein Z, L, Ring A, $R^A$, $R^D$, q, and r are as defined in claim 1.

3. The compound of claim 1, or a pharmaceutically acceptable salt thereof, wherein the compound is a compound of Formula III:

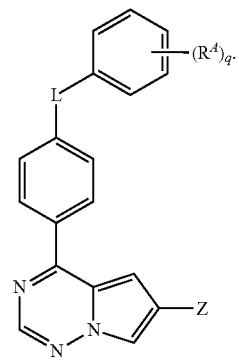

wherein Z, L, $R^A$, and q are as defined in claim 1.

4. The compound of any one of claims 1 to 3, or a pharmaceutically acceptable salt thereof, wherein L is —N($R^1$)—C(O)—($C_1$-$C_6$ alkylene)-.

5. The compound of claim 1 or 2, or a pharmaceutically acceptable salt thereof, wherein Ring A is monocyclic or bicyclic aryl.

6. The compound of claim 1 or a pharmaceutically acceptable salt thereof, wherein Z is monocyclic or bicyclic aryl, each independently substituted with 0-5 occurrences of $R^C$.

7. The compound of claim 1, or a pharmaceutically acceptable salt thereof, wherein Z is monocyclic or bicyclic heteroaryl, each independently substituted with 0-5 occurrences of $R^C$.

8. The compound of claim 1, or a pharmaceutically acceptable salt thereof, wherein Z is pyrazolyl substituted with 0-5 occurrences of $R^C$.

9. The compound of claim 1, or a pharmaceutically acceptable salt thereof, wherein each $R^A$ is independently selected from $C_1$-$C_6$ alkyl, $C_1$-$C_6$ alkoxy, halo, —N($R^1$)($R^1$), and cyano.

10. The compound of claim 1, or a pharmaceutically acceptable salt thereof, wherein each $R^C$ is independently selected from $C_1$-$C_6$ alkyl, halo, $C_1$-$C_6$ hydroxyalkyl, —C(O)$R^1$, —OC(O)$R^1$, —C(O)O$R^1$, —S$R^1$, —S(O)$_2R^1$, —S(O)$_2$—N($R^1$)($R^1$), —N($R^1$)($R^1$), —C(O)—N($R^1$)($R^1$), —N$R^1$S(O)$_2R^1$, and —O$R^1$, wherein each $C_1$-$C_6$ alkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$.

11. The compound of claim 1, or a pharmaceutically acceptable salt thereof, wherein each $R^1$ is independently selected from hydrogen, hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, and —NR"R", wherein each $C_1$-$C_6$ alkyl is independently substituted with 0-5 occurrences of $R^b$; or 2 $R^1$ together with the atom(s) to which they are attached form a cycloalkyl or heterocyclyl ring.

12. A pharmaceutical composition comprising a pharmaceutically acceptable carrier and a compound of claim 1, or a pharmaceutically acceptable salt thereof.

13. A method of treating mastocytosis, the method comprising administering to a patient in need thereof a therapeutically effective amount of a compound of claim 1 or a pharmaceutically acceptable salt thereof.

14. A method of treating gastrointestinal stromal tumor (GIST), the method comprising administering to a patient in need thereof a therapeutically effective amount of a compound of claim 1 or a pharmaceutically acceptable salt thereof.

15. A method of treating acute myeloid leukemia, the method comprising administering to a patient in need thereof a therapeutically effective amount of a compound of claim 1 or a pharmaceutically acceptable salt thereof.

16. The compound of claim 1, or a pharmaceutically acceptable salt thereof, wherein the compound is selected from:

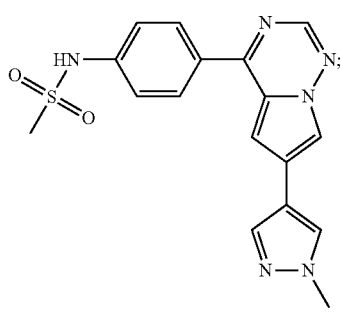

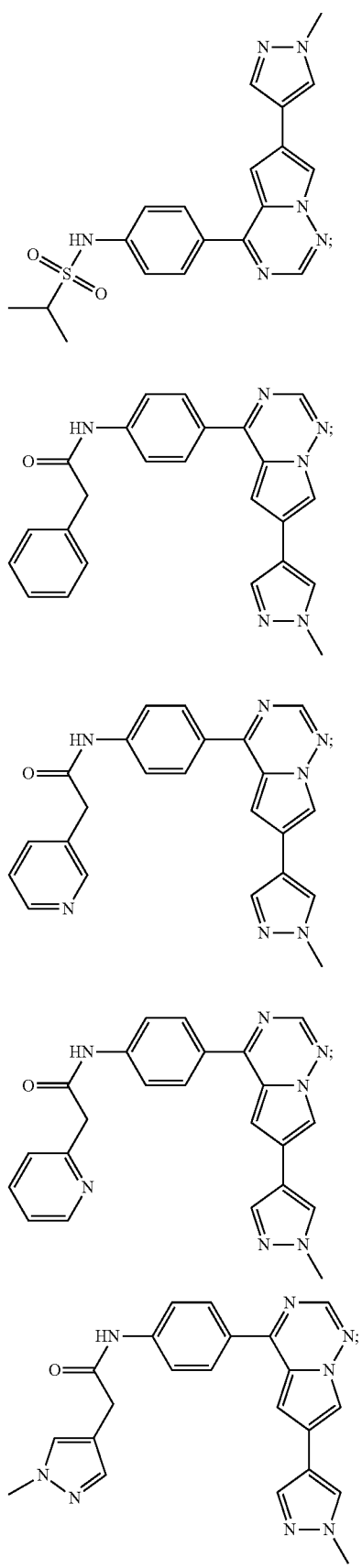

93
-continued
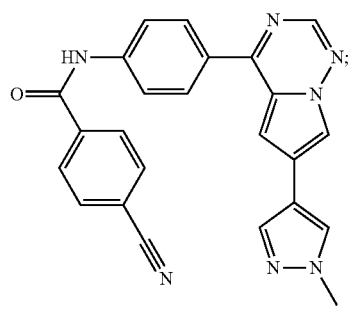
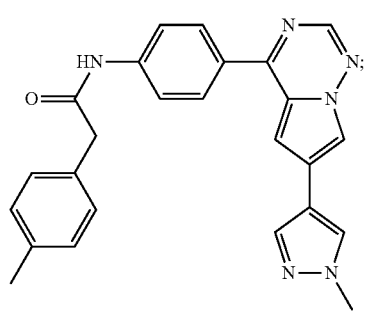
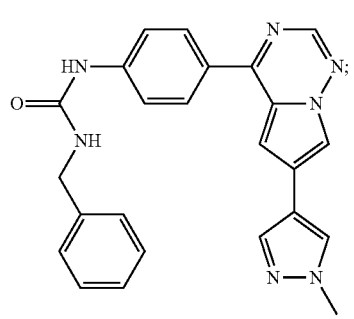
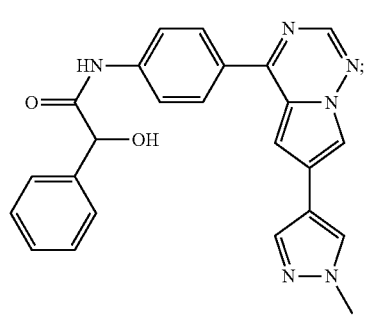
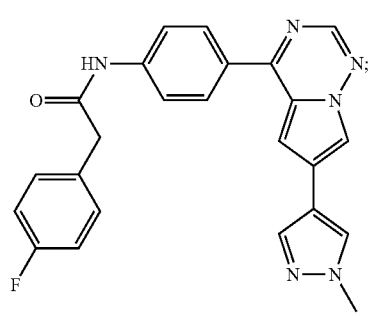
94
-continued
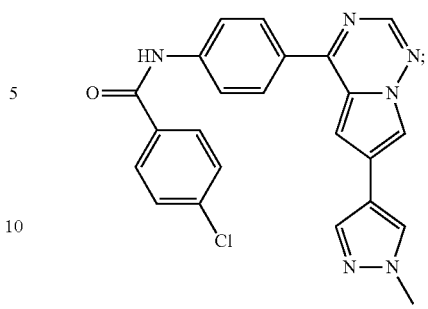
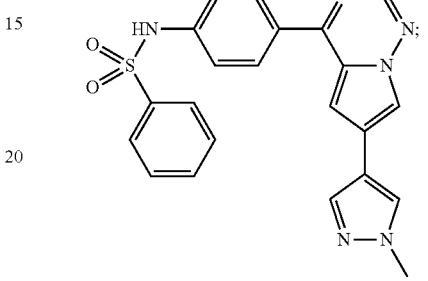
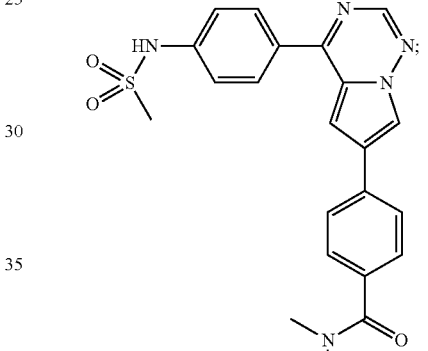
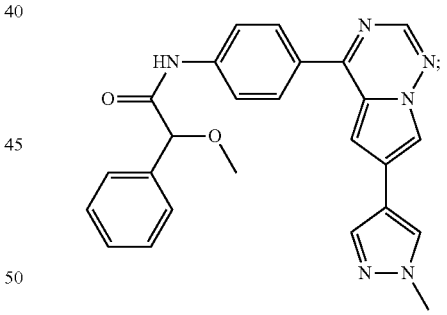
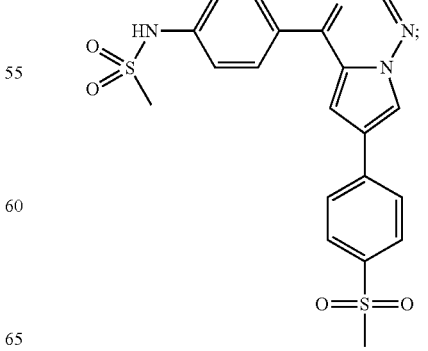

-continued
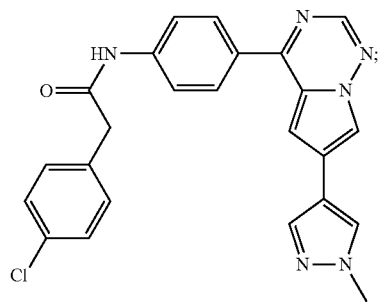
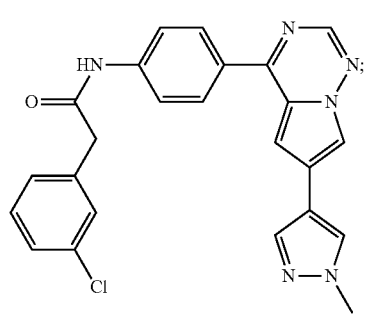
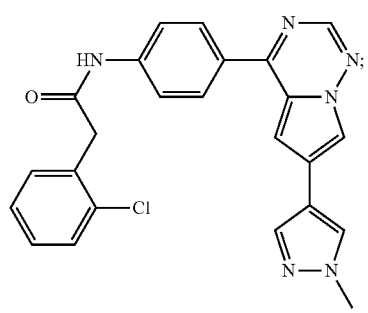
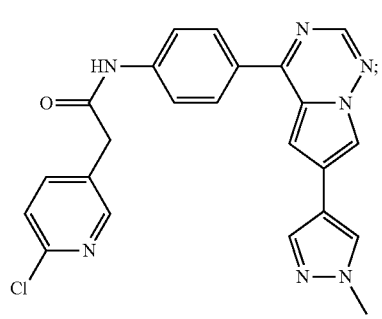
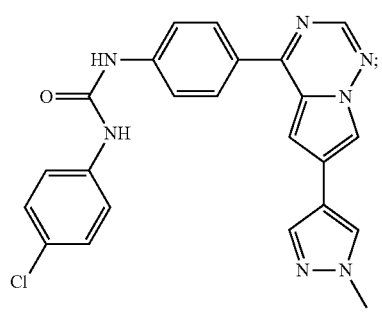
-continued
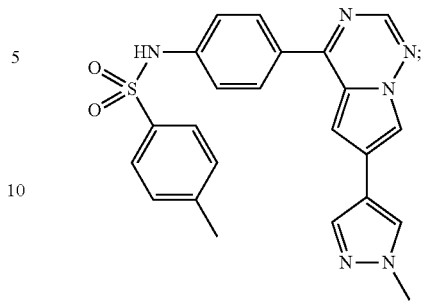
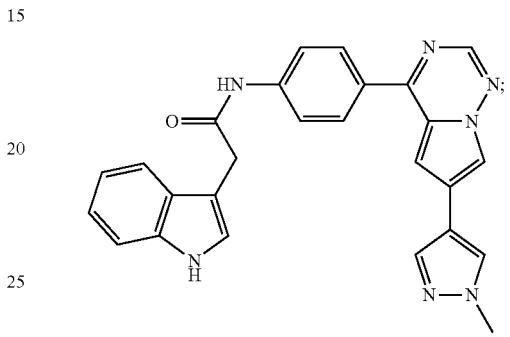
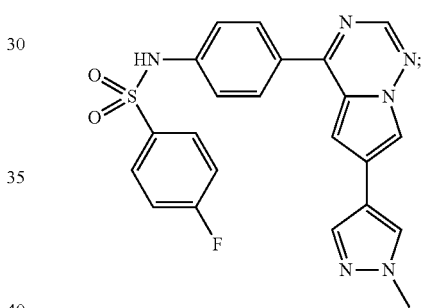
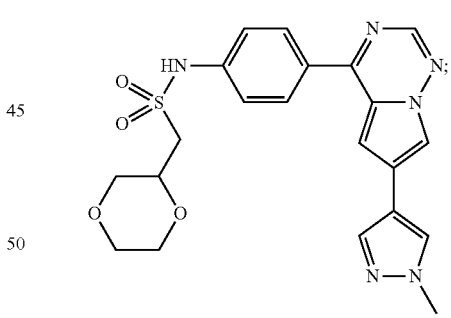
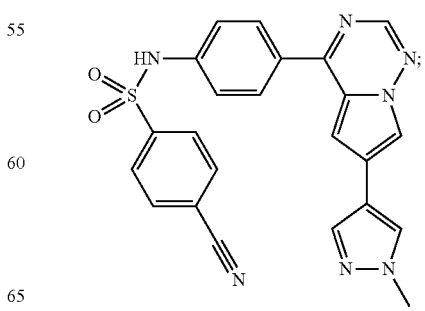

97
-continued
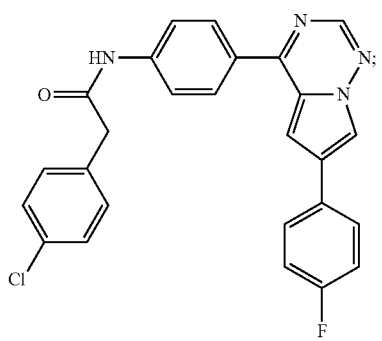
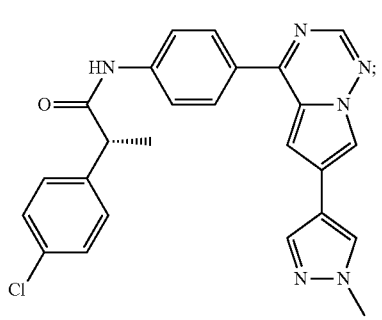
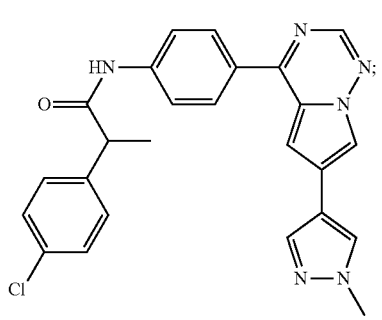
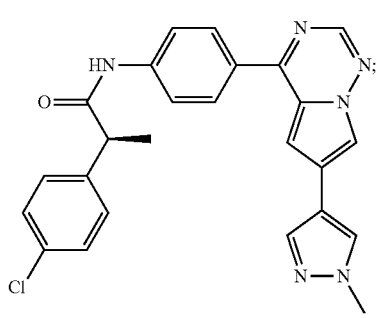
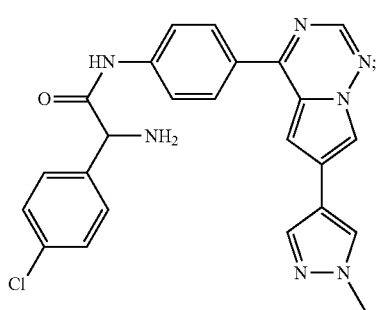
98
-continued
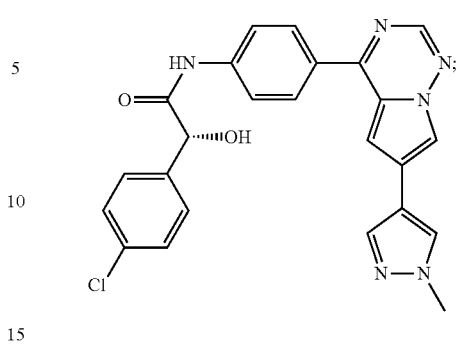
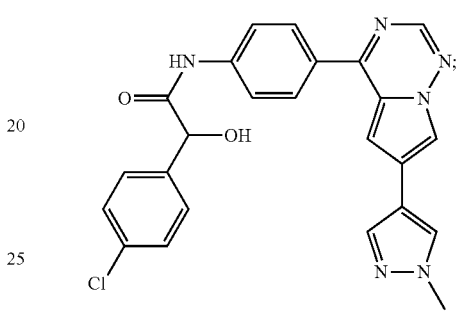
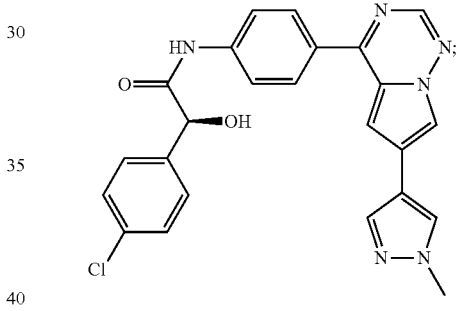
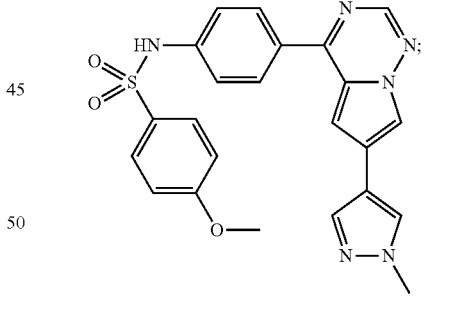
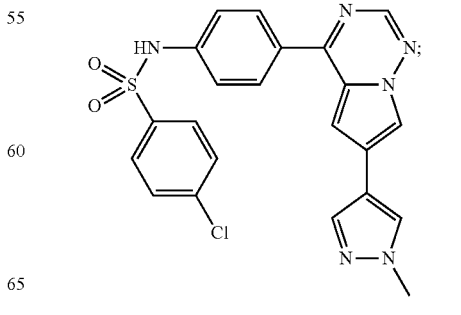

99
-continued
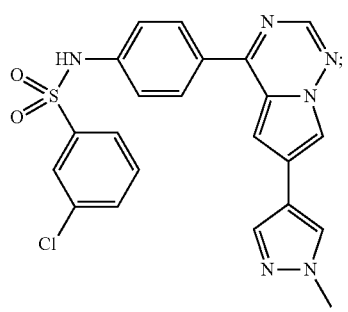
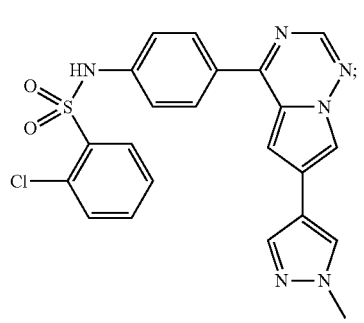
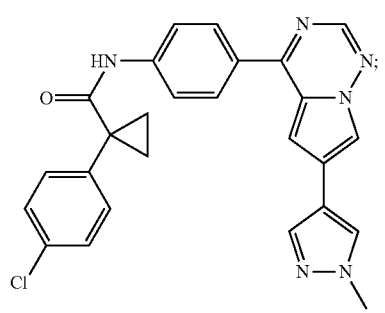
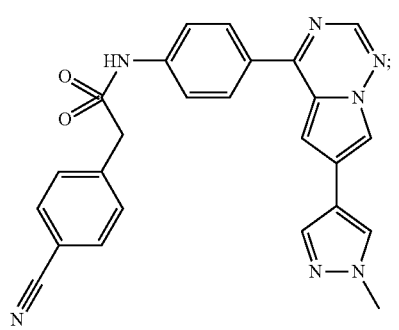
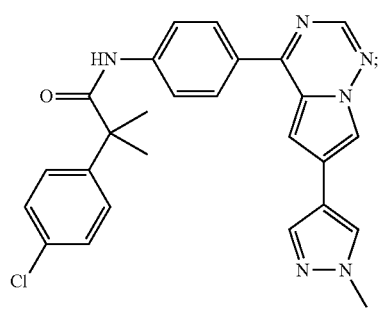
100
-continued
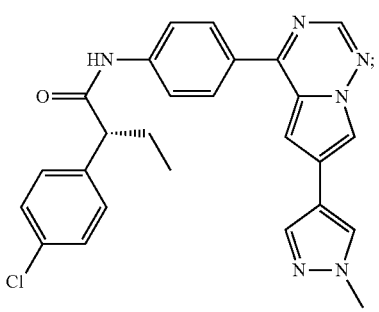
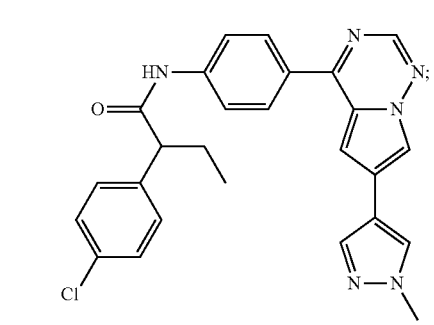
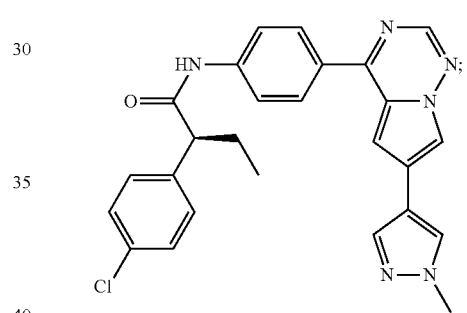
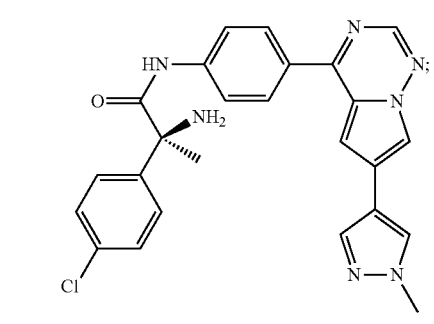
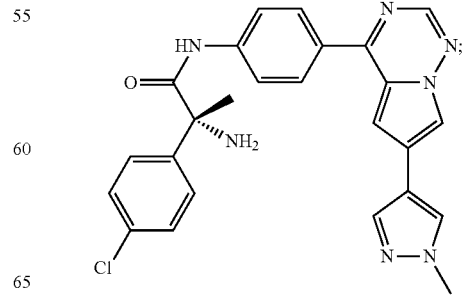

101
-continued
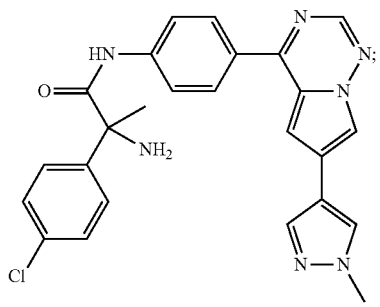
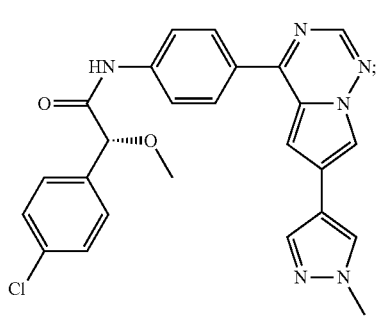
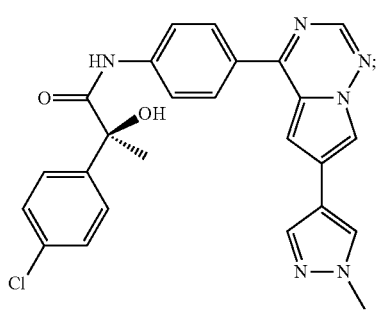
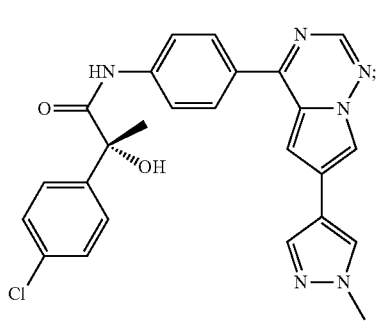
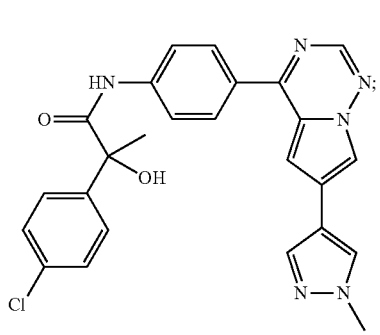
102
-continued
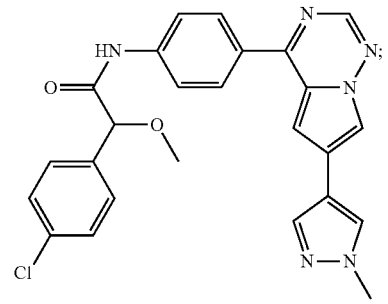
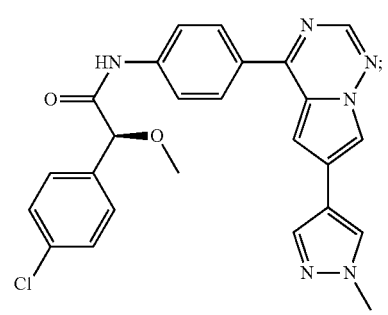
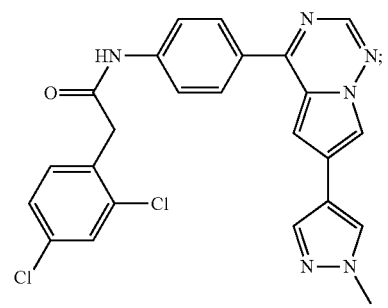
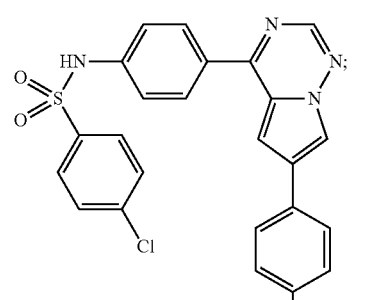
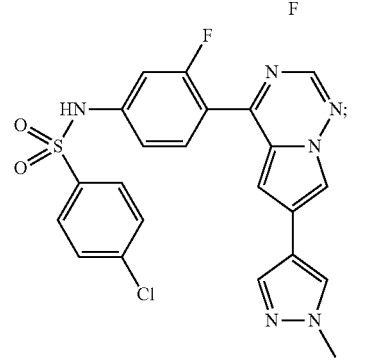

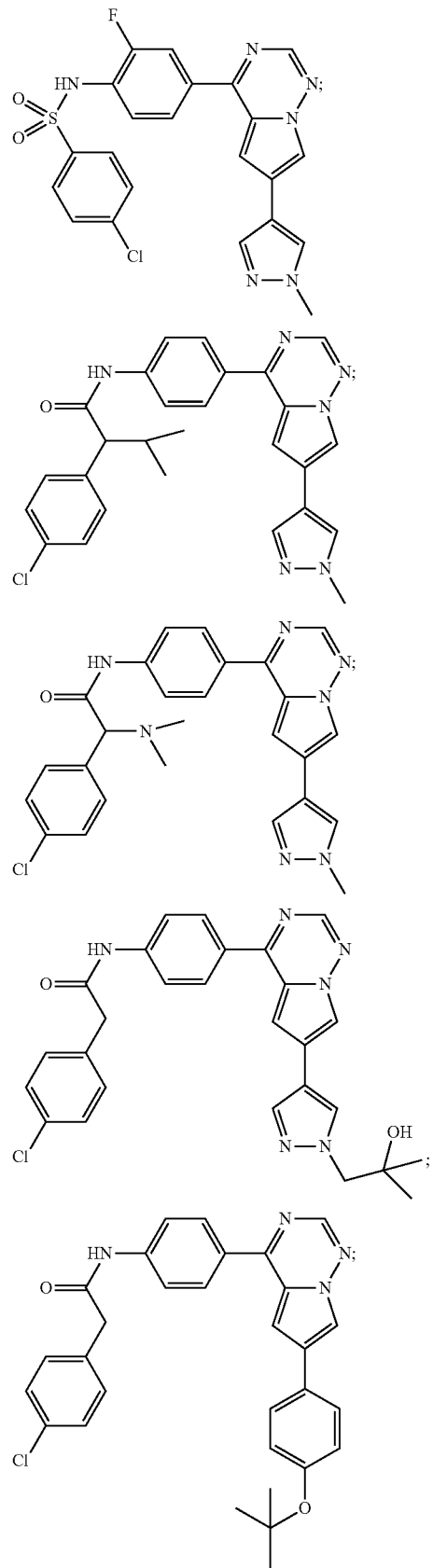
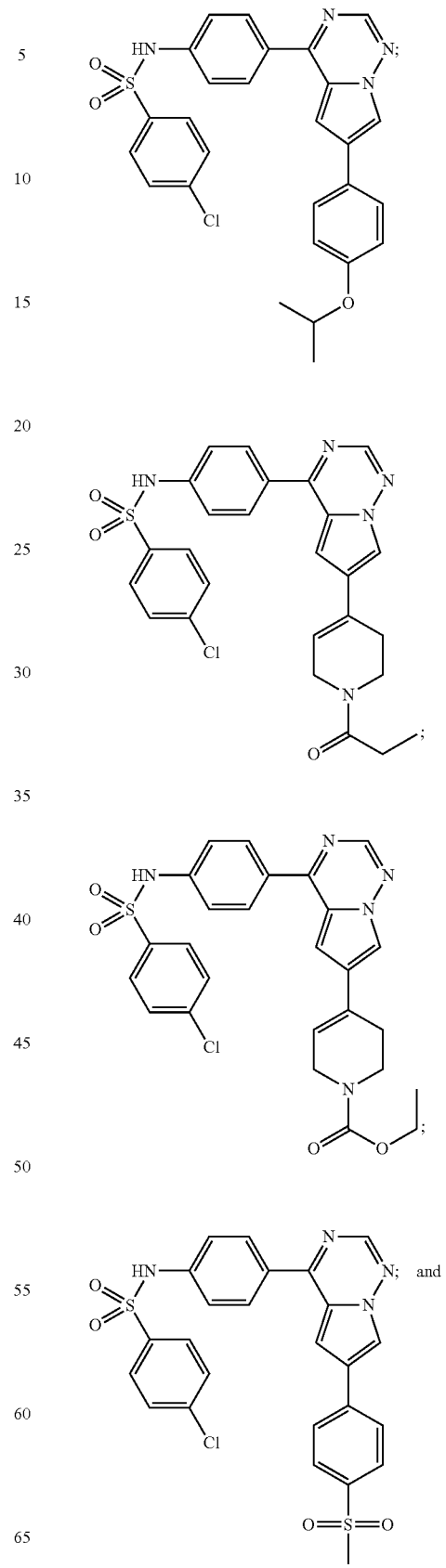

-continued

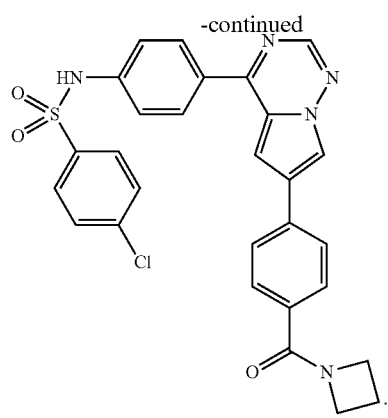

17. The compound of claim 16 which is

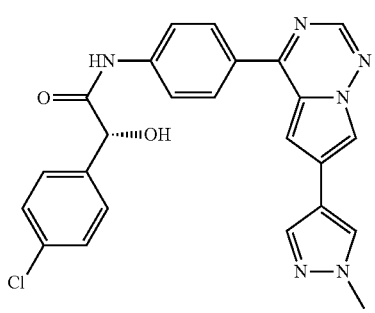 [SMILES: Cn1cc(-c2cc3c(-c4ccc(NC(=O)[C@H](O)c5ccc(Cl)cc5)cc4)ncnn3c2)cn1]

or a pharmaceutically acceptable salt thereof.

18. The method of claim 13, wherein the mastocytosis is systemic mastocytosis (SM) or cutaneous mastocytosis (CM).

19. The method of claim 18, wherein the systemic mastocytosis (SM) is selected from indolent (ISM), smoldering (SSM), aggressive (ASM), SM with associated hematologic non-mast cell lineage disease (SM-AHNMD), and mast cell leukemia (MCL).

20. The method of claim 19, wherein the systemic mastocytosis (SM) is aggressive (ASM).

21. The method of claim 19, wherein the systemic mastocytosis (SM) is SM with associated hematologic non-mast cell disease (SM-AHNMD).

22. The method of claim 19, wherein the systemic mastocytosis (SM) is mast cell leukemia (MCL).

23. The method of claim 14, wherein the patient has a D842V mutation in PDGFRα in Exon 18.

24. The method of claim 14, wherein the patient is refractory to treatment with imatinib, sunitinib, and/or regorafenib.

25. The method of claim 14, wherein the patient has unrespectable GIST.

26. The method of any one of claim 13, 14, or 15, wherein the patient has a mutation in Exon 17 in KIT.

27. The method of claim 26, wherein the patient has a D816 mutation in KIT in Exon 17.

28. The method of claim 27, wherein the D816 mutation is D816V.

29. The compound of claim 16 which is

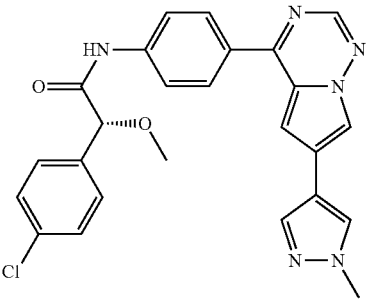

or a pharmaceutically acceptable salt thereof.

30. The compound of claim 16 which is

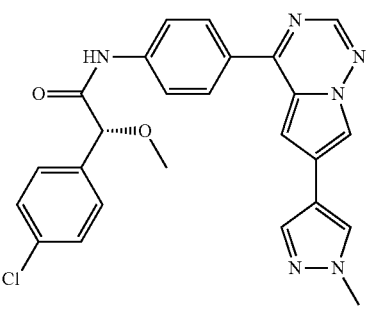

or a pharmaceutically acceptable salt thereof.

31. The compound of claim 16 which is

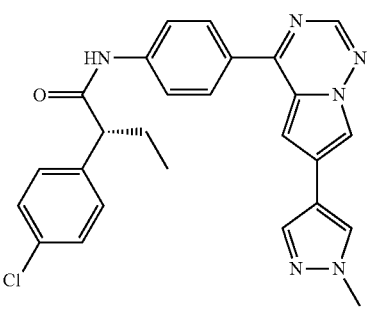 [SMILES: CC[C@@H](C(=O)Nc1ccc(-c2ncnn3cc(-c4cnn(C)c4)cc23)cc1)c1ccc(Cl)cc1]

or a pharmaceutically acceptable salt thereof.

32. The compound of claim 16 which is

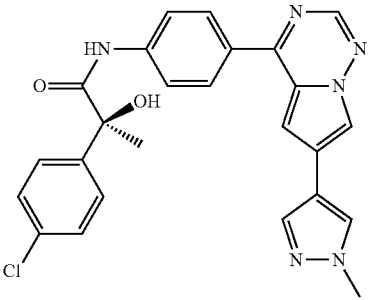 [SMILES: Cn1cc(-c2cc3c(-c4ccc(NC(=O)[C@@](C)(O)c5ccc(Cl)cc5)cc4)ncnn3c2)cn1]

or a pharmaceutically acceptable salt thereof.

33. The compound of claim 16 which is

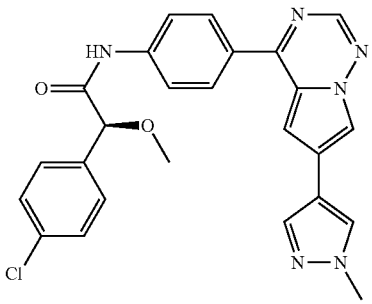 [SMILES: CO[C@H](C(=O)Nc1ccc(-c2ncnn3cc(-c4cnn(C)c4)cc23)cc1)c1ccc(Cl)cc1]

or a pharmaceutically acceptable salt thereof.

34. The compound of claim 16 which is

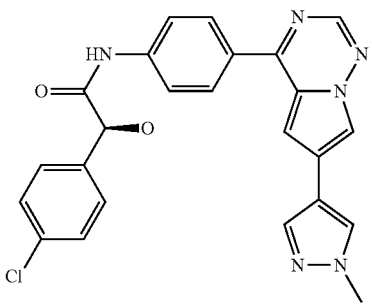 [SMILES: Cn1cc(-c2cc3c(-c4ccc(NC(=O)[C@@H](O)c5ccc(Cl)cc5)cc4)ncnn3c2)cn1]

or a pharmaceutically acceptable salt thereof.

35. A method of treating mastocytosis, the method comprising administering to a patient in need thereof a therapeutically effective amount of a compound of any of claim 17 or 29-34, or a pharmaceutically acceptable salt thereof.

36. A method of treating gastrointestinal stromal tumor (GIST), the method comprising administering to a patient in need thereof a therapeutically effective amount of a compound of any of claim 17 or 29-34, or a pharmaceutically acceptable salt thereof.

37. A method of treating acute myeloid leukemia, the method comprising administering to a patient in need thereof a therapeutically effective amount of a compound of any of claim 17 or 29-34, or a pharmaceutically acceptable salt thereof.

38. The method of claim 35, wherein the mastocytosis is systemic mastocytosis (SM) or cutaneous mastocytosis (CM).

39. The method of claim 38, wherein the systemic mastocytosis (SM) is selected from indolent (ISM), smoldering (SSM), aggressive (ASM), SM with associated hematologic non-mast cell lineage disease (SM-AHNMD), and mast cell leukemia (MCL).

40. The method of claim 39, wherein the systemic mastocytosis (SM) is aggressive (ASM).

41. The method of claim 39, wherein the systemic mastocytosis (SM) is SM with associated hematologic non-mast cell disease (SM-AHNMD).

42. The method of claim 39, wherein the systemic mastocytosis (SM) is mast cell leukemia (MCL).

43. The method of claim 36, wherein the patient has a D842V mutation in PDGFRα in Exon 18.

44. The method of claim 36, wherein the patient is refractory to treatment with imatinib, sunitinib, and/or regorafenib.

45. The method of claim 36, wherein the patient has unresectable GIST.

46. The method of claim 35, wherein the patient has a mutation in Exon 17 in KIT.

47. The method of claim 46, wherein the patient has a D816 mutation in KIT in Exon 17.

48. The method of claim 47, wherein the D816 mutation is D816V.

49. The method of claim 36, wherein the patient has a mutation in Exon 17 in KIT.

50. The method of claim 49, wherein the patient has a D816 mutation in KIT in Exon 17.

51. The method of claim 50, wherein the D816 mutation is D816V.

52. The method of claim 37, wherein the patient has a mutation in Exon 17 in KIT.

53. The method of claim 52, wherein the patient has a D816 mutation in KIT in Exon 17.

54. The method of claim 53, wherein the D816 mutation is D816V.

* * * * *

UNITED STATES PATENT AND TRADEMARK OFFICE
CERTIFICATE OF CORRECTION

PATENT NO. : 10,000,496 B2
APPLICATION NO. : 15/217503
DATED : June 19, 2018
INVENTOR(S) : Brian L. Hodous et al.

Page 1 of 1

It is certified that error appears in the above-identified patent and that said Letters Patent is hereby corrected as shown below:

In the Claims

Claim 25, Column 105, Line 60, "unrespectable GIST" should read -- unresectable GIST --.

Claim 30, Column 106, Lines 20-30:

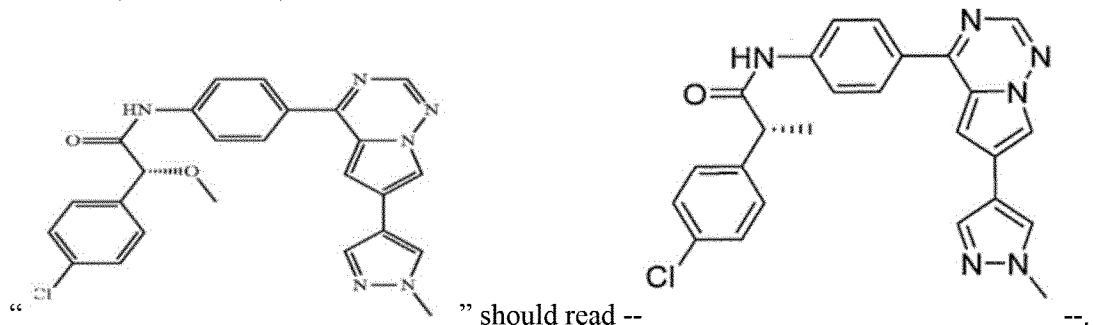
" should read --                    --.

Claim 34, Column 107, Lines 20-30:

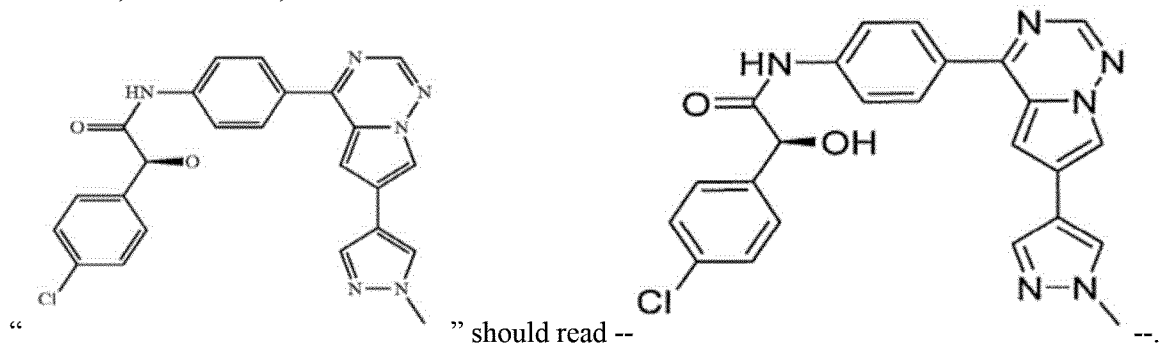
" should read --                    --.

Signed and Sealed this
Eighteenth Day of September, 2018

Andrei Iancu
*Director of the United States Patent and Trademark Office*